(12) United States Patent
Boyd et al.

(10) Patent No.: US 7,279,478 B2
(45) Date of Patent: Oct. 9, 2007

(54) CATHEPSIN CYSTEINE PROTEASE INHIBITORS

(75) Inventors: Michael Boyd, Montreal (CA); Marc Gagnon, Montreal (CA); Cheuk Lau, Ile Bizard (CA); Christophe Mellon, Montreal (CA); John Scheigetz, Dollard des Ormeaux (CA)

(73) Assignee: Merck Frosst Canada & Co., Quebec (CA)

( * ) Notice: Subject to any disclaimer, the term of this patent is extended or adjusted under 35 U.S.C. 154(b) by 248 days.

(21) Appl. No.: 10/525,264

(22) PCT Filed: Sep. 3, 2003

(86) PCT No.: PCT/CA03/01346

§ 371 (c)(1),
(2), (4) Date: Feb. 22, 2005

(87) PCT Pub. No.: WO2004/022526

PCT Pub. Date: Mar. 18, 2004

(65) Prior Publication Data

US 2006/0122268 A1 Jun. 8, 2006

Related U.S. Application Data

(60) Provisional application No. 60/408,064, filed on Sep. 4, 2002.

(51) Int. Cl.
| | | |
|---|---|---|
| A61K 31/5375 | (2006.01) | |
| A61K 31/4965 | (2006.01) | |
| A61K 31/505 | (2006.01) | |
| A61K 31/47 | (2006.01) | |
| A61K 31/44 | (2006.01) | |
| A61K 31/41 | (2006.01) | |
| A61K 31/4164 | (2006.01) | |
| A61K 31/277 | (2006.01) | |
| C07D 265/30 | (2006.01) | |
| C07D 239/26 | (2006.01) | |
| C07D 241/12 | (2006.01) | |
| C07D 215/04 | (2006.01) | |
| C07D 213/06 | (2006.01) | |
| C07D 255/03 | (2006.01) | |

(52) U.S. Cl. .............. 514/238.8; 514/252.12; 514/252.1; 514/256; 514/311; 514/357; 514/381; 514/399; 514/521; 544/170; 544/335; 544/392; 546/152; 546/330; 558/410

(58) Field of Classification Search ............... 544/381, 544/170, 335, 392; 546/79, 195, 152, 330; 548/241, 427, 252, 342.5; 558/410; 514/238.8, 514/252.12, 252.1, 256, 311, 357, 381, 399, 514/521

See application file for complete search history.

(56) References Cited

U.S. PATENT DOCUMENTS 7,012,075 B2 * 3/2006 Prasit et al. ........... 514/252.13

FOREIGN PATENT DOCUMENTS

| WO | WO 94/14811 | 7/1994 |
| WO | WO 00/49007 | 8/2000 |
| WO | WO 00 49008 | 8/2000 |
| WO | WO 00/55125 | 9/2000 |
| WO | WO 01/49288 | 7/2001 |
| WO | WO 02/069901 | 9/2002 |
| WO | WO 02/098850 | 12/2002 |

OTHER PUBLICATIONS

Obach R.S., Drug-drug interactions; An important negative attribute in drugs. Drugs of Today, 39(5), 301-38, (2003).*

Oya, Shunichi, et al., Database Accession No. 124:4081, Nuclear Medicine and Biology, vol. 22, No. 6, pp. 749-757, 1995.

Database Accession No. BRN 2447392 & Yuki Gosei Kagaku Kyokaishi, vol. 30, pp. 68, 74, 1972.

Database Accession No. Reaction ID 1403344, 1403367 & Suzue, S.; Irikura, T.—Chem. Pharm. Bull., vol. 16, No. 8, pp. 1417-1432, 1968.

Database Accession No. Reaction ID 227583 & Cook, et al.—Chem. Soc., pp. 3227, 3229, 1949.

* cited by examiner

*Primary Examiner*—Rebecca Anderson
*Assistant Examiner*—Karen Cheng
(74) *Attorney, Agent, or Firm*—Nicole M. Beeler; David A. Muthard

(57) ABSTRACT

This invention relates to class of compounds which are cysteine protease inhibitors, including but not limited to, inhibitors of cathepsins K, L, S and B. These compounds are useful for treating diseases in which inhibition of bone resorption is indicated, such as osteoporosis. They have the following structure: Formula (I)

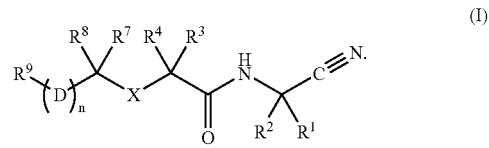

13 Claims, No Drawings

CATHEPSIN CYSTEINE PROTEASE INHIBITORS

CROSS REFERENCE TO RELATED APPLICATION

This application is a §371 National Stage Application of PCT/CA03/01346, filed on Sep. 03, 2003, which claims priority from U.S. Provisional Application Ser. No. 60/408,064, filed on Sep. 04, 2002.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, *Biochem J* 192:365-368; Delaisse, J. et al., 1984, *Biochem Biophys Res Commun:*441-447; Delaisse, J. M. et al.,1987, *Bone* 8:305-313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, F, H, L, K, S, W, and Z have been cloned. Cathepsin K (which is also known by the abbreviation cat K) is also known as cathepsin O and cathepsin O2. See PCT Application WO 96/13523, Khepri Pharmaceuticals, Inc., published May 9, 1996, which is hereby incorporated by reference in its entirety. Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immunbe responses, including, but not limited to, rejection of organ transplants or tissue grafts. Increased Cathepsin B levels and redistribution of the enzyme are found in tumors, suggesting a role in tumor invasion and matastasis. In addition, aberrant Cathpsin B activity is implicated in such disease states as rheumatoid arthritis, osteoarthritis, pneumocystisis carinii, acute pancreatitis, inflammatory airway disease and bone and joint disorders.

Cysteine protease inhibitors such as E-64 (trans-epoxysuccinyl-L-leucylamide-(4-guanidino) butane) are known to be effective in inhibiting bone resorption. See Delaisse, J. M. et al., 1987, *Bone* 8:305-313, whichis hereby incorporated by reference in its entirety. Recently, cathepsin K was cloned and found specifically expressed in osteoclasts See Tezuka, K. et al., 1994, *J Biol Chem* 269:1106-1109; Shi, G. P. et al., 1995, *FEBS Lett* 357:129-134; Bromme, D. and Okamoto, K., 1995, *Biol Chem Hoppe Seyler* 376:379-384; Bromme, D. et al., 1996, *J Biol Chzem* 271:2126-2132; Drake, F. H. et al., 1996, *J Biol Chem* 271:12511-12516, whichare hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to result in inactive protein. See Gelb, B. D. et al., 1996, *Science* 273:1236-1238; Johnson, M. R. et aL, 1996, *Genome Res* 6:1050-1055, which are hereby incorporated by reference in their entirety. Therefore, it appears that cathepsin K is involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, *J Biol Chem* 272:13955-13960; Littlewood-Evans, A. et al., 1997, *Bone* 20:81-86, whichare hereby incorporated by reference in their entirety. Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively. See Bromme, D. et al., 1996, *J Biol Chem* 271: 2126-2132; Bossard, M. J. et al., 1996, *J Biol Chem* 271: 12517-12524, which are hereby incorporated by reference in their entirety. Cathepsin K is active at a broad pH range with significant activity between pH 4-8, thus allowing for good catalytic activity in the resorption lacunae of osteoclasts where the pH is about 4-5.

Human type I collagen, the major collagen in bone is a good substrate for cathepsin K. See Kafienah, W., et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al., 1997, *Nat Struct Biol* 4: 109-11, whichare hereby incorporated by reference in their entirety. Also, selective peptide based inhibitors of cathepsin K have been developed See Bromme, D., et al., 1996, *Biochem J* 315:85-89; Thompson, S. K., et al., 1997, *Proc Natl Acad Sci USA* 94:14249-14254, which are hereby incorporated by reference in their entirety. Accordingly, inhibitors of Cathepsin K can reduce bone resorption. Such inhibitors would be useful in treating disorders involving bone resorption, such as osteoporosis.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

I.

DETAILED DESCRIPTION OF THE INVENTION

The present invention relates to compounds of the following chemical formula:

wherein $R^1$ is hydrogen, $C_{1-6}$ alkyl or $C_{1-6}$ alkenyl wherein said alkyl and alkenyl groups are optionally substituted with halo;

$R^2$ is hydrogen, $C_{1-6}$ alkyl or $C_{1-6}$ alkenyl wherein said alkyl and alkenyl groups are optionally substituted with halo;

or $R^1$ and $R^2$ can be taken together with the carbon atom to which they are attached to form a $C_{3-8}$ cycloalkyl ring wherein said ring system is optionally substituted with $C_{1-6}$ alkyl, hydroxyalkyl or halo;

$R^3$ is hydrogen, $C_{1-6}$ alkyl or $C_{1-6}$ alkenyl wherein said alkyl and alkenyl groups are optionally substituted with $C_{3-6}$ cycloalkyl or halo;

$R^4$ is hydrogen, $C_{1-6}$ alkyl or $C_{1-6}$ alkenyl wherein said alkyl and alkenyl groups are optionally substituted with $C_{3-6}$ cycloalkyl or halo;

or $R^3$ and $R^4$ can be taken together with the carbon atom to which they are attached to form a $C_{3-8}$ cycloalkyl ring, $C_{5-8}$ cycloalkenyl ring, or five to seven membered heterocycloalkyl wherein said cycloalkyl, cycloalkenyl and heterocycloalkyl groups are optionally substituted with $C_{1-6}$ alkyl, halo, hydroxyalkyl, hydroxy, alkoxy or keto;

X is selected from the group consisting of —O—, —S—, $SO_2$, and —C($R^5$)($R^6$)—;

$R^5$ is hydrogen or $C_{1-6}$ alkyl;

$R^6$ is hydrogen or $C_{1-6}$ alkyl;

or $R^5$ and $R^6$ can be taken together with any of the atoms to which they may be attached or are between them to form a 3-8 membered cycloalkyl ring system wherein said ring system is optionally substituted with $C_{1-6}$ alkyl or halo;

$R^7$ is hydrogen, $C_{1-6}$ alkyl, $C_{2-6}$ alkenyl, $C_{2-6}$ alkynyl, $C_{1-6}$ haloalkyl, $C_{1-6}$ alkyloxy, nitro, cyano, aryl, heteroaryl, $C_{3-8}$ cycloalkyl, heterocycloalkyl, —C(O)O$R^{10}$, —C(O)$R^{10}$, —C(O)OSi[CH(CH$_3$)$_2$]$_3$, —$R^{10}$C(O)$R^{13}$, —C(O)$R^{13}$, —C(O)N($R^{12}$)($R^{12}$), —C($R^{10}$)($R^{11}$)OH, —$R^{10}$S$R^{13}$, —$R^{13}$, —C($R^{13}$)$_3$, —C($R^{10}$)($R^{11}$)N($R^{13}$)$_2$, —C($R^{10}$)($R^{11}$)N($R^{10}$)$R^{13}$, —C($R^{10}$)($R^{11}$)N($R^{10}$)($R^{11}$), —C($R^{10}$)($R^{11}$)SC($R^{10}$)($R^{11}$)($R^{13}$), —C($R^a$)($R^b$)N$R^a$C($R^a$)($R^b$), —C($R^a$)($R^b$)N($R^a$)($R^b$), —($R^a$)($R^b$)C($R^a$)($R^b$)N($R^a$)($R^b$), —C(O)C($R^a$)($R^b$)N($R^a$)($R^b$), —C($R^a$)($R^b$)N($R^a$)C(O) $R^{13}$ or C($R^a$)($R^b$)C(O)N($R^a$)($R^b$); wherein said groups are optionally substituted on either the carbon or the heteroatom with one to five substituents independently selected from $C_{1-6}$ alkyl, halo, keto, cyano, haloalkyl, hydroxyalkyl, —O$R^9$, —O(aryl), —$NO_2$, —$NH_2$, —NHS(O)$_2R^{10}$, —$R^{13}SO_2R^{12}$, —$SO_2R^{12}$, —SO($R^{12}$), —$SO_2$N($R^c$)($R^d$), —$SO_2$N($R^{10}$)C(O)($R^{12}$), —C($R^{10}$)($R^{11}$)N($R^{10}$)($R^{11}$), —C($R^{10}$)($R^{11}$)OH, —COOH, —C($R^a$)($R^b$)C(O)N($R^a$)($R^b$), —N($R^{10}$)C($R^{10}$)($R^{11}$)($R^{13}$), —NH(CH$_2$)$_2$OH, —NHC(O)O$R^{10}$, —Si(CH$_3$)$_3$, heterocycloalkl, aryl or heteroaryl;

$R^8$ is hydrogen, $C_{1-6}$ alky, $C_{2-6}$ alkenyl, $C_{2-6}$ alkynyl, $C_{1-6}$ haloalkyl, $C_{1-6}$ alkyloxy, nitro, cyano, aryl, heteroaryl, $C_{3-8}$ cycloalkyl, heterocycloalkyl, —C(O)O$R^{10}$, —C(O)$R^{10}$, C(O)OSi[CH(CH$_3$)$_2$]$_3$, —$R^{10}$C(O)$R^{13}$, —C(O)$R^{13}$, —C(O)N($R^{12}$)($R^{12}$), —C($R^{10}$)($R^{11}$)OH, —$R^{10}$S$R^{13}$, —$R^{13}$, —C($R^{13}$)$_3$, —C($R^{10}$)($R^{11}$)N($R^{13}$)$_2$, —C($R^{10}$)($R^{11}$)N$R^{10}$C($R^{11}$)$R^{13}$, —C($R^{10}$)($R^{11}$)N($R^{10}$)$R^{13}$, —C($R^{10}$)($R^{11}$)N($R^{10}$)($R^{11}$), —C($R^{10}$)($R^{11}$)SC($R^{10}$)($R^{11}$)($R^{13}$), —C($R^a$)($R^b$)N$R^a$C($R^a$)($R^b$)($R^{13}$), —C($R^a$)($R^b$)N($R^a$)($R^b$), —C($R^a$)($R^b$)C($R^a$)($R^b$)N($R^a$)($R^b$), —C(O)C($R^a$)($R^b$)N($R^a$)($R^b$), —C($R^a$)($R^b$)N($R^a$)C(O) $R^{13}$ or C($R^a$)($R^b$)C(O)N($R^a$)($R^b$); wherein said groups are optionally substituted on either the carbon or the heteroatom with one to five substituents independently selected from $C_{1-6}$ alkyl, halo, keto, cyano, haloalkyl, hydroxyalkyl, —O$R^9$, —O(aryl), —$NO_2$, —$NH_2$, —NHS(O)$_2R^{10}$, —$R^{13}SO_2R^{12}$, —$SO_2R^{12}$, SO($R^{12}$), —$SO_2$N($R^c$)($R^d$), —$SO_2$N($R^{10}$)C(O)($R^{12}$), —C($R^{10}$)($R^{11}$)N($R^{10}$)($R^{11}$), —C($R^{10}$)($R^{11}$)OH, —COOH, —C($R^a$)($R^b$)C(O)N($R^a$)($R^b$), —N($R^{10}$)C($R^{10}$)($R^{11}$)($R^{13}$), —NH(CH$_2$)$_2$OH, —NHC(O)O$R^{10}$, —Si(CH$_3$)$_3$, heterocycloalky, aryl or heteroaryl;

D is aryl, heteroaryl, $C_{3-8}$ cycloalkyl, heterocycloalkyl, $C_{1-3}$ alkyl or $C_{1-3}$ alkenyl wherein said aryl, heteroaryl, cycloalkyl and heterocycloalkyl groups, which may be monocyclic or bicyclic, are optionally substituted on either the carbon or the heteroatom with one to three substituents selected from $C_{1-6}$ alkyl, $C_{2-6}$ alkenyl, $C_{2-6}$ alkynyl, $C_{1-6}$ alkyloxy, halo, keto, nitro, cyano, aryl, heteroaryl, $C_{3-8}$ cycloalkyl, heterocyclyl, —C(O)OR$^{10}$, —C(O)OSi[CH(CH$_3$)$_2$]$_3$, —OR$^{10}$, —C(O)R$^{10}$, —R$^{10}$C(O)R$^{13}$, —C(O)R$^{13}$, —C(O)N(R$^{12}$)(R$^{12}$), —C(R$^{10}$)(R$^{11}$)OH, —SR$^{12}$, —SR$^{13}$, —R$^{10}$SR$^{13}$, —R$^{13}$, —C(R$^{13}$)$_3$, —C(R$^{10}$)(R$^{11}$)N(R$^{13}$)$_2$, —SO$_2$R$^{12}$, —SO(R$^{12}$), —SO$_2$R$^{13}$, —SO$_2$N(R$^c$)(R$^d$), —SO$_2$CH(R$^{10}$)(R$^{11}$), —SO$_2$N(R$^{10}$)C(O)(R$^{12}$), —SO$_2$(R$^{10}$)C(O)N(R$^{12}$)$_2$, —OSO$_2$R$^{10}$, —N(R$^{10}$)(R$^{11}$), —N(R$^{10}$)C(O)NR$^{10}$R$^{13}$, —N(R$^{10}$)C(O)R$^{10}$, —N(R$^{10}$)C(O)OR$^{10}$, —N(R$^{10}$)SO$_2$R$^{10}$, —C(R$^{10}$)(R$^{11}$)NR$^{10}$C(R$^{10}$)(R$^{11}$)R$^{13}$, —C(R$^{10}$)(R$^{11}$)N(R$^{10}$)R$^{13}$, —C(R$^{10}$)(R$^{11}$)N(R$^{10}$)(R$^{11}$), —C(R$^{10}$)(R$^{11}$)SC(R$^{10}$)(R$^{11}$)(R$^{13}$), R$^{10}$S—, —C(R$^a$)(R$^b$)NR$^a$C(R$^a$)(R$^b$)(R$^{13}$), —C(R$^a$)(R$^b$)N(R$^a$)(R$^b$), —C(R$^a$)(R$^b$)C(R$^a$)(R$^b$)N(R$^a$)(R$^b$), —C(O)C(R$^a$)(R$^b$)N(R$^a$)(R$^b$), —C(R$^a$)(R$^b$)N(R$^a$)C(O)R$^{13}$ or —C(R$^a$)(R$^b$)C(O)N(R$^a$)(R$^b$); wherein said groups are optionally substituted on either the carbon or the heteroatom with one to five substituents independently selected from $C_{1-6}$ alkyl, $C_{3-8}$ cycloalkyl, halo, keto, cyano, haloalkyl, hydroxyalkyl, —OR$^{13}$, —NO$_2$, —NH$_2$, —NHS(O)$_2$R$^{10}$, —R$^{13}$SO$_2$R$^{12}$, —SO$_2$R$^{12}$, —SO(R$^{12}$), —SO$_2$N(R$^c$)(R$^d$), —SO$_2$N(R$^{10}$)C(O)(R$^{12}$), —C(R$^{10}$)(R$^{11}$)N(R$^{10}$)(R$^{11}$), —C(R$^{10}$)(R$^{11}$)OH, —COOH, —C(R$^a$)(R$^b$)C(O)N(R$^a$)(R$^b$), —N(R$^{10}$)C(R$^{10}$)(R$^{11}$), —NH(CH$_2$)$_2$OH, —NHC(O)OR$^{10}$, —Si(CH$_3$)$_3$, heterocycloalkyl, aryl or heteroaryl;

R$^9$ is hydrogen, hydroxy, cyano, $C_{1-6}$ alkyl, $C_{2-6}$ alkenyl, $C_{2-6}$ alkynyl, $C_{1-6}$ alkyloxy, halo, aryl, heteroaryl, $C_{3-8}$ cycloalkyl, heterocycloalkyl, —C(O)OR$^{10}$, —OR$^{10}$, —C(O)R$^{10}$, —C(O)R$^{13}$, —C(O)N(R$^{12}$)(R$^{12}$), —C(R$^{10}$)(R$^{11}$)OH, —R$^{10}$SR$^{13}$, —R$^{13}$, —C(R$^{13}$)$_3$, —C(R$^{10}$)(R$^{11}$)N(R$^{13}$)$_2$, SR$^{10}$, —SO$_2$R$^{12}$, —SO(R$^{12}$), —SO$_2$R$^{13}$, —SO$_2$N(R$^c$)(R$^d$), —SO$_2$CH(R$^{10}$)(R$^{11}$), —N(R$^{10}$)(R$^{11}$), —N(R$^{10}$)C(O)NR$^{10}$R$^{13}$, —N(R$^{10}$)C(O)R$^{10}$, —N(R$^{10}$)C(O)OR$^{10}$, —N(R$^{10}$)SO$_2$R$^{10}$, —C(R$^{10}$)(R$^{11}$)NR$^{10}$C(R$^{10}$)(R$^{11}$)R$^{13}$, —C(R$^{10}$)(R$^{11}$)N(R$^{10}$)R$^{13}$, —C(R$^{10}$)(R$^{11}$)N(R$^{10}$)(R$^{11}$), —C(R$^{10}$)(R$^{11}$)SC(R$^{10}$)(R$^{11}$)—, R$^{10}$S—, —C(R$^a$)(R$^b$)NR$^a$C(R$^a$)(R$^b$), —C(R$^a$)(R$^b$)N(R$^a$)(R$^b$), —C(R$^a$)(R$^b$)C(R$^a$)(R$^b$)N(R$^a$)(R$^b$), —C(O)C(R$^a$)(R$^b$)N(R$^a$)(R$^b$), —C(R$^a$)(R$^b$)N(R$^a$)C(O)R$^{13}$; wherein said groups are optionally substituted on either the carbon or the heteroatom with one to five substituents independently selected from $C_{1-6}$ alkyl, $C_{3-8}$ cycloalkyl, halo, keto, cyano, haloalkyl, hydroxyalkyl, —OR$^{13}$, —NO$_2$, —NH$_2$, —NHS(O)$_2$R$^8$, —R$^{13}$SO$_2$R$^{12}$, SO$_2$R$^{12}$, SO(R$^{12}$), SO$_2$N(R$^c$)(R$^d$), SO$_2$N(R$^{10}$)C(O)(R$^{12}$), —C(R$^{10}$)(R$^{11}$)N(R$^{10}$)(R$^{11}$), —C(R$^{10}$)(R$^{11}$)OH, —COOH, —C(R$^a$)(R$^b$)C(O)N(R$^a$)(R$^b$), —N(R$^{10}$)C(R$^{10}$)(R$^{11}$), —NH(CH$_2$)$_2$OH, —NHC(O)OR$^{10}$, Si(CH$_3$)$_3$, heterocycloalkyl, aryl or heteroaryl;

R$^{10}$ is hydrogen or $C_{1-6}$ alkyl;

R$^{11}$ is hydrogen or $C_{1-6}$ alkyl;

R$^{12}$ is hydrogen or $C_{1-6}$ alkyl which is optionally substituted with halo, alkoxy, cyano, —NR$^{10}$ or —SR$^{10}$;

R$^{13}$ is selected from the group consisting of hydrogen, aryl, aryl($C_{1-4}$) alkyl, heteroaryl, heteroaryl($C_{1-4}$)alkyl, $C_{3-8}$cycloalkyl, $C_{3-8}$cycloalkyl($C_{1-4}$)alkyl, and heterocycloalkyl($C_{1-4}$)alkyl wherein said groups can be optionally substituted with halo or alkoxy;

R$^a$ is hydrogen, $C_{1-6}$ alkyl, ($C_{1-6}$ alkyl)aryl, ($C_{1-6}$ alkyl)hydroxyl, —O($C_{1-6}$ alkyl), hydroxyl, halo, aryl, heteroaryl, $C_{3-8}$ cycloalkyl, heterocycloalkyl, wherein said alkyl, aryl, heteroaryl, $C_{3-8}$ cycloalkyl and heterocycloalkyl can be optionally substituted on either the carbon or the heteroatom with $C_{1-6}$ alkyl or halo;

R$^b$ is hydrogen, $C_{1-6}$ alkyl, ($C_{1-6}$ alkyl)aryl, ($C_{1-6}$ alkyl)hydroxyl, alkoxyl, hydroxyl, halo, aryl, heteroaryl, $C_{3-8}$ cycloalkyl, heterocycloalkyl,wherein said alkyl, aryl, heteroaryl, $C_{3-8}$ cycloalkyl and heterocycloalkyl can be optionally substituted on either the carbon or the heteroatom with $C_{1-6}$ alkyl or halo;

or R$^a$ and R$^b$ can be taken together with the carbon atom to which they are attached or are between them to form a $C_{3-8}$ cycloalkyl ring or $C_{3-8}$ heterocycloalkyl ring wherein said 3-8 membered ring system may be optionally substituted with $C_{1-6}$ alkyl and halo;

R$^c$ is hydrogen or $C_{1-6}$ alkyl which is optionally substituted with halo or OR$^{13}$;

R$^d$ is hydrogen or $C_{1-6}$ alkyl which is optionally substituted with halo or OR$^{13}$;

or R$^c$ and R$^d$ can be taken together with the nitrogen atom to which they are attached or are between them to form a $C_{3-8}$ heterocycloalkyl ring which is optionally substituted with $C_{1-6}$ alkyl, halo hydroxyalkyl, hydroxy, alkoxy or keto; n is zero, one, two or three; and the pharmaceutically acceptable salts and N-oxide derivatives thereof.

In an embodiment of the invention, R$^1$ and R$^2$ are each hydrogen. In another embodiment of the invention, R$^1$ and R$^2$, when on the same carbon atom, can be taken together with the carbon atom to which they are attached to form a 3-8 membered ring system wherein said ring system is optionally substituted with $C_{1-6}$ alkyl, hydroxyalkyl or halo. Examples of ring systems that can be formed include cyclopropyl, cyclobutyl, cyclopentyl, cyclohexyl and cycloheptyl. In a further embodiment, R$^1$ and R$^2$, when on the same carbon atom, can be taken together with the carbon atom to which they are attached to form a cyclopropyl ring wherein said ring system is optionally substituted with $C_{1-6}$ alkyl or halo. A preferred embodiment is when cyclopropyl is formed.

In an embodiment of the invention, R$^3$ is hydrogen and R$^4$ are each independently $C_{1-6}$ alkyl which is optionally substituted with $C_{3-6}$ cycloalkyl ring or halo. In a futher embodiment of the invention R$^3$ is hydrogen and R$^4$ is isobutyl. In another embodiment of the invention, R$^3$ and R$^4$, when on the same carbon atom, can be taken together with the carbon atom to which they are attached to form $C_{3-8}$ cycloalkyl ring, $C_{5-8}$ cycloalkenyl ring, or five to seven membered heterocyclyl wherein said cycloalkyl, cycloalkenyl and heterocyclyl groups are optionally substituted with $C_{1-6}$ alkyl, halo, hydroxyalkyl, hydroxy, alkoxy or keto. Examples of ring systems that can be formed include, but are not limited to the following, keeping in mind that the heterocycle is optionally substituted with one or more substituents as described above: cyclopropyl, cyclobutyl, cyclopentyl, cyclohexyl and cycloheptyl. A preferred embodiment is when cyclohexyl is formed.

In an embodiment of the invention, X is —O—, —S— or —SO$_2$—. In a further embodiment of the invention, X is O.

In an embodiment of the invention, R$^7$ is aryl, heteroaryl or $C_{1-6}$ haloalkyl and R$^8$ is hydrogen. In a further embodiment of the invention, R$^7$ is phenyl or CF$_3$.

In an embodiment of the invention, D is aryl, heteroaryl, cycloalkyl or heterocycloalkyl. In a further embodiment of the invention, D is phenyl or pyridyl.

In an embodiment of the invention, R$^9$ is aryl, heteroaryl or heterocycloalkyl, wherein said groups are optionally substituted on either the carbon or the heteroatom with one to five substituents independently selected from $C_{1-6}$ alkyl, halo, —SO$_2$R$^{12}$, —SO(R$^{12}$) or aryl. In a further embodiment of the invention, R$^9$ is piperidine, phenylpiperazine, pyridine or phenylmethylsulfone.

In an embodiment of the invention, $R^a$ and $R^b$ are defined such that they can be taken together with the carbon or nitrogen to which they are attached to form a monocyclic or bicyclic carbocycle or heterocycle with 5-7 members in each ring. The heterocycle can optionally contain, in addition to the nitrogen, 1 or 2 additional heteroatoms selected from N, O and S. Said carbocycle and heterocycle can be optionally substituted with one or more substituents selected from $C_{1-6}$ alkyl and halo.

Embodied by the present invention are methods for treating disorders related to abnormal bone resoprtion. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. A preferred embodiment includes methods for treating osteoporosis and metastatic bone disease. A more preferred embodiment includes methods for treating osteoporosis.

Specific embodiments of the present invention include, but are not limited to:

(2S)-2-{[(R)-(4-bromophenyl)(phenyl)methyl]oxy}-N-(cyanomethyl)-4-methylpentanamide;

(2S)-N-(cyanomethyl)-4-methyl-2-{[(R)-phenyl(4'-piperazin-1-yl-1,1'-biphenyl-4-yl)methyl]oxy}pentanamide;

(2S)-N-(cyanomethyl)-4-methyl-2-{[(R)-phenyl(4'-pyridin-4-yl-1,1'-biphenyl-4-yl)methyl]oxy}pentanamide;

(2S)-2-({(R)-(4-bromophenyl)[4-(methylsulfonyl)phenyl]methyl}oxy)-N-(cyanomethyl)-4-methylpentanamide;

(2S)-N-(cyanomethyl)-4-methyl-2-{[(S)-[4-(methylsulfonyl)phenyl](4'-piperazin-1-yl-1,1'-biphenyl-4-yl)methyl]oxy}pentanamide;

(2S)-N-(cyanomethyl)-2-{[(R)-[4'-(1H-imidazol-1-yl)-1,1'-biphenyl-4-yl](phenyl) methyl]oxy}-4-methylpentanamide;

(2S)-2-{[(R)-(4-bromophenyl)(4-chlorophenyl)methyl]oxy}-N-(cyanomethyl)-4-methylpentanamide;

(2S)-2-{[(S)-(4-bromophenyl)(mesityl)methyl]oxy}-N-(cyanomethyl)-4-methylpentanamide;

(2S)-2-(benzhydryloxy)-N-(cyanomethyl)-4-methylpentanamide;

(2S)-2-{[(S)-(4-chlorophenyl)(4'-piperazin-1-yl-1,1'-biphenyl-4-yl)methyl]oxy}-N -(cyanomethyl)-4-methylpenteanamide;

(2S)-N-(cyanomethyl)-2-{[(S)-mesityl(4'-piperazin-1-yl-1,1'-biphenyl-4-yl)methyl]oxy}-4-methylpentanamide;

1-{[(R)-(4-bromophenyl)(phenyl)methyl]oxy}-N-(cyanomethyl)cyclohexanecarboxade;

(2S)-2-{[(1R)-1-(4-bromophenyl)-2-(4-chlorophenyl)ethyl]oxy}-N-(cyanomethyl)-4-methylpentanamide;

(2S)-2-{[(R)-(4-bromophenyl)(cyclopropyl)methyl]oxy}-N-(cyanomethyl)-4-methylpenteanamide;

(2S)-2-{[(R)-(3-bromophenyl)(phenyl)methyl]oxy}-N-(cyanomethyl)-4-methyipentanamide;

2-[(4-bromophenyl)(1-methyl-1H-pyrazol-5-yl)methoxy]-N-(cyanomethyl)-4-methylpentanamide;

2-[(4-bromophenyl)(1-methyl-1H-pyrazol-5-yl)methoxy]-N-(cyanomethyl)-4-methylpentanamide;

(2S)-2-[[4-(3-chloropyrazin-2-yl)phenyl](phenyl)methoxy]-N-(cyanomethyl)-4-methylpentanamide;

(2S)-N-(cyanomethyl)-4-methyl-2-{phenyl[4-(1,3-thiazol-2-yl)phenyl]methoxy}pentanamide;

(2S)-2-[[4'-(aminosulfonyl)-1,1'-biphenyl-4-yl](phenyl)methoxy]-N-(cyanomethyl)-4-methylpentanamide;

(2S)-N-(cyanomethyl)-4-methyl-2-[[4'-(methylsulfonyl)-1,1'-biphenyl-4-yl](phenyl)methoxy]pentanamide;

(2S)-N-(cyanomethyl)-4-methyl-2-[phenyl(4-quinolin-3-ylphenyl)methoxy]pentanamide;

(2S)-N-(cyanomethyl)-4-methyl-2-[phenyl(4-pyrimidin-5-ylphenyl)methoxy]pentanamide;

(2S)-N-(cyanomethyl)-4-methyl-2-[phenyl(4-quinolin-8-ylphenyl)methoxy]pentanamide;

(2S)-N-(cyanomethyl)-2-[{4-[6-(hydroxymethyl)-1-oxidopyridin-3-yl]phenyl}(phenyl)methoxy]-4-methylpentanamide;

(2S)-N-(cyanomethyl)-4-methyl-2-[phenyl(4-pyridin-4-ylphenyl)methoxy]pentanamide;

(2S)-N-(cyanomethyl)-2-[[4-(1H-indol-4-yl)phenyl](phenyl)methoxy]-4-methylpentanamide;

(2S)-N-(cyanomethyl)-4-methyl-2-[phenyl(4-pyridin-2-ylphenyl)methoxy]pentanamide;

(2S)-N-(cyanomethyl)-4-methyl-2-[phenyl(4-pyrazin-2-ylphenyl)methoxy]pentanamide;

(2S)-N-(cyanomethyl)-4-methyl-2-[phenyl(4-pyridin-3-ylphenyl)methoxy]pentanamide;

(2S)-N-(cyanomethyl)-4-methyl-2-(phenyl{4-[5-(2H-tetraazol-5-yl)pyridin-3-yl]phenyl}methoxy)pentanamide;

(2S)-N-(cyanomethyl)-4-methyl-2-[[4-(3-methylpyridin-2-yl)phenyl](phenyl)methoxy]pentanamide;

2-{4-[[((1S)-1-{[(cyanomethyl)amino]carbonyl}-3-methylbutyl)oxy](phenyl)methyl]phenyl}isonicotinic acid;

(2S)-N-(cyanomethyl)-4-methyl-2-[phenyl(4-pyridin-2-ylphenyl)methoxy]pentanamide;

ethyl 4'-[[((1S)-1-{[(cyanomethyl)amino]carbonyl}-3-methylbutyl)oxy](phenyl)methyl]-1,1'-biphenyl-4-carboxylate;

4'-[[((1S)-1-{[(cyanomethyl)amino]carbonyl}-3-methylbutyl)oxy](phenyl)methyl]-1,1'-biphenyl-4-carboxamide;

N-(cyanomethyl)-4-methyl-2-{phenyl[4-(piperazin-1-ylcarbonyl)phenyl]methoxy}pentanamide;

N-(cyanomethyl)-2-[(4-{[4-(2-fluoroethyl)piperazin-1-yl]carbonyl}phenyl)(phenyl)methoxy]-4-methylpentanamide;

N-(cyanomethyl)-4-methyl-2-[(4-{[4-(methylsulfonyl)piperazin-1-yl]carbonyl}phenyl)(phenyl)methoxy]pentanamide;

(2S)-2-{[(S)-(4-bromophenyl)(thien-2-yl)methyl]oxy}-N-(cyanomethyl)-4-methylpentanamide;

(2S)-N-(cyanomethyl)-4-methyl-2-{[(S)-(4'-piperazin-1-yl-1,1'-biphenyl-4-yl)(thien-2-yl)methyl]oxy}pentanamide;

(2S)-2-[(4-bromophenyl)(thien-3-yl)methoxy]-N-(cyanomethyl)-4-methylpentanamide;

2-[(4-bromophenyl)(pyridin-2-yl)methoxy]-N-(cyanomethyl)-4-methylpentanamide;

2-[(4-bromophenyl)(1,3-thiazol-2-yl)methoxy]-N-(cyanomethyl)-4-methylpentanamide;

N-(cyanomethyl)-4-methyl-2-[(4'-piperazin-1-yl-1,1'-biphenyl-4-yl)(pyridin-2-yl)methoxy]pentanamide;

N-(cyanomethyl)-4-methyl-2-[(4'-piperazin-1-yl-1,1'-biphenyl-4-yl)(1,3-thiazol-2-yl)methoxy]pentanamide;

2-[(4-bromophenyl)(pyridin-3-yl)methoxy]-N-(cyanomethyl)-4-methylpentanamide;

2-[(4-bromophenyl)(pyridin-4-yl)methoxy]-N-(cyanomethyl)-4-methylpentanamide;

2-[1-(4-bromophenyl)ethoxy]-N-(cyanomethyl)-4-methylpentanamide;

2-[1-(4-bromophenyl)propoxy]-N-(cyanomethyl)-4-methylpentanamide;

2-[1-(4-bromophenyl)ethoxy]-N-(cyanomethyl)-4-methylpentanamide;

N-(cyanomethyl)-2-[(4-fluorophenyl)(4-pyridin-4-ylphenyl)methoxy]-4-methylpentanamide;
2-[(4-bromophenyl)(4-fluorophenyl)methoxy]-N-(cyanomethyl)-4-methylpentanamide;
2-[(4-bromophenyl)(4-fluorophenyl)methoxy]-N-(1-cyanocyclopropyl)-4-methylpentanamide;
N-(cyanomethyl)-2-[(4-fluorophenyl)(4'-piperazin-1-yl-1,1'-biphenyl-4-yl)methoxy]-4-methylpentanamide;
2-[1-(4-bromophenyl)propoxy]-N-(cyanomethyl)-4-methylpentanamide;
N-(1-cyanocyclopropyl)-2-[(4-fluorophenyl)(4'-piperazin-1-yl-1,1'-biphenyl-4-yl)methoxy]-4-methylpentanamide;
N-(cyanomethyl)-4-methyl-2-[phenyl(4'-piperazin-1-yl-1,1'-biphenyl-4-yl)methoxy]pentanamide;
(2S)-N-(cyanomethyl)-2-[(4-fluorophenyl)(4'-piperazin-1-yl-1,1'-biphenyl-4-yl)methoxy]-4-methylpentanamide;
(2S)-N-(cyanomethyl)-4-methyl-2-[phenyl(4'-piperazin-1-yl-1,1'-biphenyl-4-yl)methoxy]pentanamide;
(2S)-2-[(4-bromophenyl)(phenyl)methoxy]-N-(cyanomethyl)-4-methylpentanamide;
(2S)-N-(cyanomethyl)-4-methyl-2-{[(S)-phenyl(4'-piperazin-1-yl-1,1'-biphenyl-4-yl)methyl]oxy}pentanamide;
N-(cyanomethyl)-4-methyl-2-[1-(4'-piperazin-1-yl-1,1'-biphenyl-4-yl)ethoxy]pentanamide;
N-(cyanomethyl)-4-methyl-2-[1-(4'-piperazin-1-yl-1,1'-biphenyl-4-yl)ethoxy]pentanamide;
(2S)-2-[(4-bromophenyl)(4-fluorophenyl)methoxy]-N-(cyanomethyl)-4-methylpentanamide;
(2S)-N-(Cyanomethyl)-4-methyl-2-{[(R)-[4'-(methylthio)-1,1'-biphenyl-4-yl](phenyl)methyl]oxy}pentanamide;
(2S)-N-(cyanomethyl)-4-methyl-2-{[(R)-[4'-(methylsulfonyl)-1,1'-biphenyl-4-yl](phenyl)methyl]oxy}pentanamide;
(2S)-N-(Cyanomethyl)-4-methyl-2-{[(R)-(4'-morpholin-4-yl-1,1'-biphenyl-4-yl)(phenyl)methyl]oxy}pentanamide;
(2S)-2-[(4-bromophenyl)(cyclohexyl)methoxy]-N-(cyanomethyl)-4-methylpentanamide;
(2S)-2-[(4-bromophenyl)(cyclohexyl)methoxy]-N-(cyanomethyl)-4-methylpentanamide;
(2S)-2-{[1-(4-bromophenyl)-2-methylprop-2-enyl]oxy}-N-(cyanomethyl)-4-methylpentanamide;
(2S)-2-{[1-(4-bromophenyl)-2-methylprop-2-enyl]oxy}-N-(cyanomethyl)-4-methylpentanamide;
(2S)-2-[1-(4-bromophenyl)-2-methylpropoxy]-N-(cyanomethyl)-4-methylpentanamide;
(2S)-2-[1-(4-bromophenyl)-2-methylpropoxy]-N-(cyanomethyl)-4-methylpentanamide;
2-[1-(4-bromophenyl)-2,2,2-trifluoroethoxy]-N-(cyanomethyl)-4-methylpentanamide;
(2S)-N-(cyanomethyl)-2-{[(R)-(4-cyanophenyl)(phenyl)methyl]oxy}-4-methylpentanamide;
(2S)-N-(cyanomethyl)-4-methyl-2-[((R)-phenyl{4-[(trimethylsilyl)ethynyl]phenyl}methyl)oxy]pentanamide;
(2S)-N-(cyanomethyl)-2-{[(R)-(4-ethynylphenyl)(phenyl)methyl]oxy}-4-methylpentanamide;
2-[1-(4-bromophenyl)-2,2,2-trifluoroethoxy]-N-(cyanomethyl)-4-methylpentanamide;
N-(cyanomethyl)-4-methyl-2-[2,2,2-trifluoro-1-(4'-piperazin-1-yl-1,1'-biphenyl-4-yl)ethoxy]pentanamide;
2-{[(S)-(4-bromophenyl)(phenyl)methyl]oxy}-N-(cyanomethyl)-4-methylpentanamide;
2-[(4-bromophenyl)(phenyl)methoxy]-N-(cyanomethyl)-4-methylpentanamide;
N-(cyanomethyl)-4-methyl-2-[phenyl(4-pyridin-4-ylphenyl)methoxy]pentanamide;
N-(cyanomethyl)-4-methyl-2-[phenyl(4'-piperazin-1-yl-1,1'-biphenyl-4-yl)methoxy]pentanamide;
(2R)-2-[(4-bromophenyl)(4-fluorophenyl)methoxy]-N-(cyanomethyl)-4-methylpentanamide;
(2S)-N-(cyanomethyl)-4-methyl-2-{[(R)-{4'-[4-(methylsulfonyl)piperazin-1-yl]-1,1'-biphenyl-4-yl}(phenyl)methyl]oxy}pentanamide;
2-{[(4-bromophenyl)(phenyl)methyl]thio}-N-(cyanomethyl)-4-methylpentanamide;
(2S)-N-(cyanomethyl)-4-methyl-2-{[(R)-[4'-(4-methylpiperazin-1-yl)-1,1'-biphenyl-4-yl](phenyl)methyl]oxy}pentanamide;
N-(cyanomethyl)-4-methyl-2-(2,2,2-trifluoro-1-{4'-[4-(methylsulfonyl)piperazin-1-yl]-1,1'-biphenyl-4-yl}ethoxy)pentanamide;
2-[(4-bromophenyl)(2,4,6-trifluorophenyl)methoxy]-N-(cyanomethyl)-4-methylpentanamide;
(2S)-2-[bis(4-bromophenyl)methoxy]-N-(cyanomethyl)-4-methylpentanamide;
(2S)-N-(cyanomethyl)-4-methyl-2-{[(R)-phenyl(4-pyridin-4-ylphenyl)methyl]oxy}pentanamide;
4-{4'-[(R)-[((1S)-1-{[(cyanomethyl)amino]carbonyl}-3-methylbutyl)oxy](phenyl)methyl]-1,1'-biphenyl-4-yl}-1,1-dimethylpiperazin-1-ium iodide;
(2S)-N-(cyanomethyl)-2-{[(R)-{4'-[4-(2-hydroxyethyl)piperazin-1-yl]-1,1'-biphenyl-4-yl}(phenyl)methyl]oxy}-4-methylpentanamide;
2-{[(4-bromophenyl)(phenyl)methyl]sulfonyl}-N-(cyanomethyl)-4-methylpentanamide;
N-(cyanomethyl)-4-methyl-2-{2,2,2-trifluoro-1-[4'-(methylthio)-1,1'-biphenyl-4-yl]ethoxy}pentanamide;
2-[1-(4-bromophenyl)-2,2,2-trifluoroethoxy]-N-(1-cyanocyclopropyl)-4-methylpentanamide;
N-(cyanomethyl)-4-methyl-2-{2,2,2-trifluoro-1-[4'-(methylsulfonyl)-1,1'-biphenyl-4-yl]ethoxy}pentanamide;
4-[[((1S)-1-{[(cyanomethyl)amino]carbonyl}-3-methylbutyl)oxy(phenyl)methyl]-N-methoxy-N -methylbenzamide;
4-[[((1S)-1-{[(cyanomethyl)amino]carbonyl}-3-methylbutyl)oxy](phenyl)methyl]-N,N -dimethylbenzamide;
(2S)-N-(cyanomethyl)-4-methyl-2-[[4-(morpholin-4-ylcarbonyl) phenyl](phenyl)methoxy]pentanamide;
4-[[((1S)-1-{[(cyanomethyl)amino]carbonyl}-3-methylbutyl)oxy](phenyl)methyl]benzoic acid;
(2S)-N-(cyanomethyl)-4-methyl-2-{[(R)-{4-[4-(methylthio)benzoyl]phenyl}(phenyl)methyl]oxy}pentanamide;
(2S)-N-(cyanomethyl)-4-methyl-2-{[(R)-{4-[4-(methylsulfonyl)benzoyl]phenyl}(phenyl)methyl]oxy}pentanamide;
(2S)-2-{[(R)-[4-(1,1'-biphenyl-4-ylcarbonyl)phenyl](phenyl)methyl]oxy}-N-(cyanomethyl) -4-methylpentanamide;
(2S)-2-[{5-bromopyridin-2-yl)(phenyl)methoxy]-N-(cyanomethyl)-4-methylpentanamide;
(2S)-N-(cyanomethyl)-4-methyl-2-{phenyl[5-(4-piperazin-1-ylphenyl)pyridin-2-yl]methoxy}pentanamide;
(2S)-N-(cyanomethyl-4-methyl-2-[{5-[4-(methylthio)phenyl]pyridin-2-yl}(phenyl)methoxy]pentanamide;
(2S)-N-(cyanomethyl-4-methyl-2-[{5-[4-(methylthio)phenyl]pyridin-2-yl}(phenyl)methoxy]pentanamide;
(2S)-N-(cyanomethyl-4-methyl-2-{[R or S)-{5-[4-(methylsulfonyl)phenyl]pyridin-2-yl}(phenyl)methyl]oxy}pentanamide;
(2S)-N-(cyanomethyl-4-methyl-2-{[(R or S)-{5-[4-methylsulfonyl)phenyl]pyridin-2-yl}(phenyl)methyl]oxy}pentanamide;

(2S)-N-(cyanomethyl-4-methyl-2-[{5-[4-(methylsulfonyl)phenyl]-1-oxidopyridin-2-yl}(phenyl)methoxy]pentanamide;

(2S)-2-[(4-bromothien-2-yl)(phenyl)methoxy]-N-(cyanomethyl)-4-methylpentanamide;

(2S)-2-[(5-bromo-1-oxidopyridin-2-yl)(phenyl)methoxy]-N-(cyanomethyl)-4-methylpentanamide;

(2S)-N-(cyanomethyl)-4-methyl-2-{[(R)-[4-(1-methylpiperidin-4-yl)phenyl](phenyl) methyl]oxy}pentanamide;

(2S)-N-(cyanomethyl)-2-{[(R)-{4-[1-(2-methoxyethyl)piperidin-4-yl]phenyl}(phenyl) methyl]oxy)-4-methylpentanamide;

(2S)-N-(cyanomethyl)-4-methyl-2-{[(R)-[4-(6-methyl-1-oxidopyridin-3-yl)phenyl](phenyl)(phenyl)methyl]oxy}pentanamide;

(2S)-N-(cyanomethyl)-4-methyl-2-{[(R)-[4-(1-oxidopyridin-4-yl)henyl](phenyl) methyl]oxy}pentanamide;

(2S)-N-(cyanomethyl)-4-methyl-2-{[(R)-[4-(1-methyl-1-oxidopiperidin-4-yl)phenyl](phenyl)methyl]oxy}pentanamide;

(2S)-N-(cyanomethyl)-2-{[(R)-{4-[1-(2-methoxyethyl)-1-oxidopiperidin-4-yl]phenyl}(phenyl)(phenyl)methyl]oxy-4-methylpentanamide;

(2S)-N-(cyanomethyl)-4-methyl-2-{[(R)-[4-(5-methylcyclohex-1-en-1-yl)phenyl(phenyl)methyl]oxy}pentanamide;

3-{4-[(R)-[((1S)-1-{[(cyanomethyl)amino]carbonyl}-3-methylbutyl)oxy](phenyl)methyl]phenyl}-1-methylpyridinium iodide;

(2S)-N-(cyanomethyl)-4-methyl-2-{[(R)-[4-(1-methylpiperidin-3-yl)phenyl](phenyl)methyl]oxy)pentanamide;

(2S)-N-(cyanomethyl)-4-methyl-2-{[(R)-phenyl(4-pyridin-3-ylphenyl)methyl]oxy}pentanamide;

(2S)-N-(cyanomethyl)-4-methyl-2-{[(R)-[4-(1-oxidopyridin-3-yl)phenyl](phenyl)methyl]oxy}pentanamide;

(2S)-N-(cyanomethyl)-2-{[(R)-{4-[1-(2-methoxyethyl)piperidin-3-yl]phenyl}(phenyl)methyl]oxy}-4-methylpentanamide;

(2S)-N-(cyanomethyl)-4-methyl-2-{[(R)-phenyl(4-quinolin-3-ylphenyl)methyl]oxy}pentanamide;

(2S)-N-(cyanomethyl)-4-methyl-2-{[(R)-[4-(1-methyl-1,2,3,4-tetrahydroquinolin-3-yl)phenyl](phenyl)methyl]oxy}pentanamide;

(2S)-N-(cyanomethyl)-4-methyl-2-{[(R)-[4-(1-oxidoquinolin-3-yl)phenyl](phenyl)methyl]oxy}pentanamide;

(2S)-N-(cyanomethyl)-2-{[(R)-{4-[1-(2-methoxyethyl)-1-oxidopiperidin-3-yl]phenyl}(phenyl)methyl]oxy}-4-methylpentanamide;

(2S)-N-(1-cyanocyclopropyl)-2-[(R)-[4'-(1-hydroxycyclopropyl)biphenyl-4-yl](phenyl)methoxyl]-4-methylpentanamide;

(2S)-N-(1-cyanocyclopropyl)-4-methyl-2-{(R)-phenyl[4'-(2,2,2-trifluoro-1-hydroxyethyl)biphenyl-4-yl]methoxy}pentanamide;

(2S)-2-[(R)-[4'-(1-amino-2,2,2-trifluoroethyl)biphenyl-4-yl](phenyl)methoxy]-N-(1-cyanocyclopropyl)-4-methylpentanamide;

1-{4'-[(R)-[((1S)-1-{[(1-cyanocyclopropyl)amino]carbonyl}-3-methylbutyl)oxy](phenyl)methyl]biphenyl-4-yl}cyclopropanecarboxylic acid;

2-{4'-[(R)-[((1S)-1-{[(1-cyanocyclopropyl)amino]carbonyl}-3-methylbutyl)oxy](phenyl)methyl]biphenyl-4-yl}-2-hydroxypropanoic acid;

(2S)-N-(1-cyanocyclopropyl)-2-[(R)-[4'-(2-hydroxyethyl)biphenyl-4-yl](phenyl)methoxy]-4-methylpentanamide;

(2S)-N-(1-cyanocyclopropyl)-2-[(R)-{4'-[cyclopropyl(hydroxy)methyl]biphenyl-4-yl}(phenyl)methoxy]-4-methylpentanamide;

(2S)-N-(1-cyanocyclopropyl)-2-[(R)-[3'-(1-hydroxyethyl)biphenyl-4-yl](phenyl)methoxy]-4-methylpentanamide;

(2S)-N-(1-cyanocyclopropyl)-2-[(R)-[3'-(1-hydroxy-1-methylethyl)biphenyl-4-yl](phenyl)methoxy]-4-methylpentanamide;

(2S)-N-(1-cyanocyclopropyl)-2-[(R)-[3'-(1-cyanocyclopropyl)biphenyl-4-yl](phenyl)methoxy]-4-methylpentanamide;

(2S)-N-(1-cyanocyclopropyl)-2-[(R)-[4'-(1-cyanocyclopropyl)biphenyl-4-yl](phenyl)methoxy]-4-methylpentanamide;

(2S)-2-[(R)-[3',4'-bis(1-hydroxy-1-methylethyl)biphenyl-4-yl](phenyl)methoxy]-N-(1-cyanocyclopropyl)-4-methylpentanamide;

(2S)-2-[(R)-[3',4'-bis(1-hydroxycyclopropyl)biphenyl-4-yl](phenyl)methoxy]-N-(1-cyanocyclopropyl)-4-methylpentanamide;

and the pharmaceutically acceptable salts, stereoisomers and N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

"Cathepsin dependent diseases or conditions" refer to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteoporosis in cathepsin K-deficient mice. Proc. Natl. acad. Sci. USA 95:13453-13458; 1998.

Another embodiment of the invention is a method treating cancer in a mammal in need thereof, comprising administering to the mammal a therapeutically effective amount of any of the compounds or any of the pharmaceutical compositions described above. It is known in the literature that Cathepsin K is expressed in human breast carcinoma, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma."

Cancer Res Dec. 1, 1997;57(23):5386-90.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and cornstarch, and lubricating agents, such as magnesium stearate, are commonly added. For oral administration in capsule form, useful diluents include lactose and dried cornstarch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid artritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

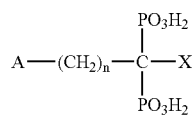

wherein n is an integer from 0 to 7 and wherein A and X are independently selected from the group consisting of H, OH, halogen, $NH_2$, SH, phenyl, C1-C30 alkyl, C3-C30 branched or cycloalkyl, bicyclic ring structure containing two or three N, C1-C30 substituted alkyl, C1-C10 alkyl substituted $NH_2$, C3-C10 branched or cycloalkyl substituted $NH_2$, C1-C10 dialkyl substituted $NH_2$, C1-C10 alkoxy, C1-C10 alkyl substituted thio, thiophenyl, halophenylthio, C1-C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3-C10 ring.

In the foregoing chemical formula, the alkyl groups can be straight, branched, or cyclic, provided sufficient atoms are selected for the chemical formula. The C1-C30 substituted alkyl can include a wide variety of substituents, nonlimiting examples which include those selected from the group consisting of phenyl, pyridyl, furanyl, pyrrolidinyl, imidazonyl, $NH_2$, C1-C10 alkyl or dialkyl substituted $NH_2$, OH, SH, and C1-C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting of alkali metal, alkaline metal, ammonium, and mono-, di-, tri-, or tetra-C1-C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and J. Org. Chem 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for EMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

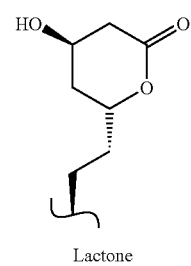

Lactone

I

-continued

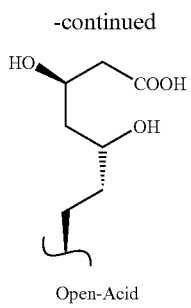

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta^8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic $\alpha v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ (>$10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invetion therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

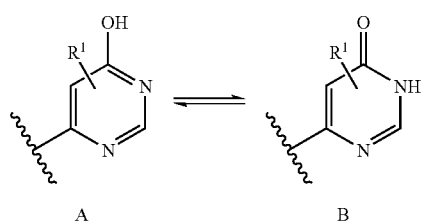

When any variable (e.g. $R^1$, $R^2$, $R^a$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on. "Alkoxy" represents an alkyl group of indicated number of carbon atoms attached through an oxygen bridge.

The term "cycloalkyl" or "carbocycle" shall mean cyclic rings of alkanes of three to eight total carbon atoms, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "cycloalkenyl" shall mean cyclic rings of 3 to 10 carbon atoms and at least 1 carbon to carbon double bond (i.e., cycloprenpyl, cyclobutenyl, cyclopenentyl, cyclohexenyl, cycloheptenyl or cycloocentyl).

The term "alkynyl" refers to a hydrocarbon radical straight or branched, containing from 2 to 10 carbon atoms and at least 1 carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O). The term "alkoxy" as used herein means an alkyl portion, where alkyl is as defined above, connected to the remainder of the molecule via an oxygen atom. Examples of alkoxy include methoxy, ethoxy and the like.

The term "haloalkyl" includes an alkyl portion, where alkyl is as defined above, which is substituted with one to five halo.

The term "hydroxyalkyl" means a linear monovalent hydrocarbon raidcal of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "heterocycloalkye" or "heterocycle" as used herein is intended to mean a 5- to 10-membered nonaromatic ring containing from 1 to 4 heteroatoms selected from the group consisting of O, N and S, and includes bicyclic groups. "Heterocycloalkyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The present invention also includes N-oxide derivatives and protectedderivatives of compounds of Formula I. For example, when compounds of Formula I contain an oxidizable nitrogen atom, the nitrogen atom can beconverted to an N-oxide by methods well known in the art. Also when compounds of Formula I contain groups such as hydroxy, carboxy, thiol or anygroup containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

The alkyl, alkenyl, alkynyl, cycloalkyl, aryl, heteroaryl and heterocycloalkyl substituents may be unsubstituted or unsubstituted, unless specifically defined otherwise. For example, a $(C_1-C_6)$ alkyl may be substituted with one or more substituents selected from OH, oxo, halogen, alkoxy, dialkylamino, or heterocycloalkyl, such as morpholinyl, piperidinyl, and so on. In the case of a disubstituted alkyl, for instance, wherein the substituents are oxo and OH, the following are included in the definition: —(C═O)CH$_2$CH (OH)CH$_3$, —(C═O)OH, —CH$_2$(OH)CH$_2$CH(O), and so on.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharmn. Sci*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:

| | |
|---|---|
| AcOH = | acetic acid |
| Boc = | t-butyloxycarbonyl |
| Boc$_2$O = | di-tert-butyl dicarbonate |
| BuLi = | butyl lithium |
| CCl$_4$ = | carbon tetrachloride |
| CH$_2$Cl$_2$ = | methylene chloride |
| CH$_3$CN = | acetonitrile |
| CHCl$_3$ = | chloroform |
| Cs$_2$CO$_3$ = | cesium carbonate |
| CuI = | copper iodide |
| DMA = | N,N-dimethyl acetamide |
| DMAP = | 4-(dimethylamino)pyridine |
| DMF = | N,N-dimethylformamide |
| DMSO = | dimethylsulfoxide |
| EDCI = | 1-(3-dimethylaminopropyl)-3-ethylcarbodiimide hydrochloride |
| Et$_2$O = | diethyl ether |
| Et$_3$N = | triethylamine |
| EtOAc = | ethyl acetate |
| EtOH = | ethanol |
| HATU = | o-(7-azabenzotriazol-1-yl)-N,N,N',N'-tetramethyluronium hexafluorophosphate |
| HOAc = | acetic acid |
| K$_2$CO$_3$ = | potassium carbonate |
| KOBu$^t$ = | potassium tert-butoxide |
| LiOH = | lithium hydroxide |
| mCPBA = | metachloroperbenzoic acid |
| MeOH = | methanol |
| MeSO$_3$H = | methane sulfonic acid |
| MgSO$_4$ = | magnesium sulfate |
| Ms = | methanesulfonyl = mesyl |
| MsCl = | methanesulfonyl chloride |
| NaBH$_4$ = | sodium borohydride |
| NaH = | sodium hydride |
| Na$_2$CO$_3$ = | sodium carbonate |
| NaHCO$_3$ = | sodium hydrogencarbonate |
| NaOH = | sodium hydroxide |
| Na$_2$SO$_4$ = | sodium sulfate |
| NBS = | N-bromosuccinimide |
| NH$_3$ = | ammonia |
| NH$_4$Cl = | ammonium chloride |
| Pd/C = | palladium on carbon |
| PdCl$_2$(dppf) = | [1,1'-bis(diphenylphosphino)ferrocene]dichloropalladium(II) |
| Pd$_2$(dba)$_3$ = | tris(dibenzylideneacetone)dipalladium(0) |
| PPh$_3$ = | triphenylphosphine |
| PPTS = | pyridinium p-toluenesulfonate |
| iPr$_2$Nli = | lithium diisopropyl amide |
| PyBOP = | benzotriazol-1-yloxytris(pyrrolidino)phosphonium-hexafluorophosphate |
| rt = | room temperature |
| sat. aq. = | saturated aqueous |
| TFA = | trifluoroacetic acid |
| THF = | tetrahydrofuran |
| tlc = | thin layer chromatography |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

obtained can be reacted with a trichloroacetimidate in the presence of acid to afford the ether product, which can then be further derivatized to introduce other pharmacophores.

Scheme 2

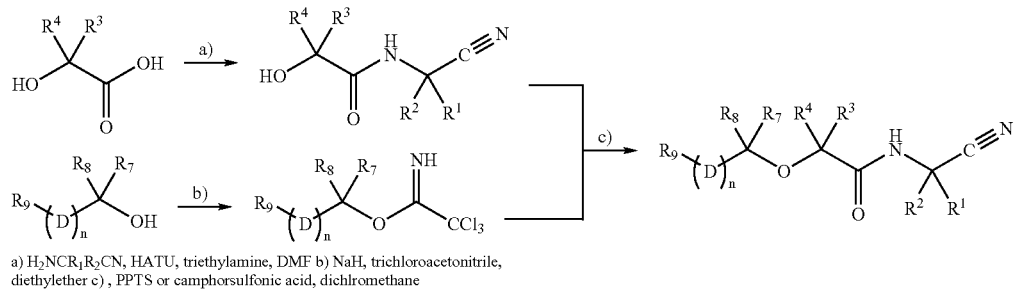

a) H$_2$NCR$_1$R$_2$CN, HATU, triethylamine, DMF b) NaH, trichloroacetonitrile, diethylether c) , PPTS or camphorsulfonic acid, dichlromethane Compounds of the present invention can be prepared according to Scheme 1, as indicated below. Thus an alpha-hydroxy acid can be condensed with an aldehyde, for example, upon azeotropic removal of water in the presence of an acid. The dioxolone affords mainly the acid when treated with zinc chloride followed by a Grignard reagent at low temperature. The acid undergoes amide formation in the presence of a dehydrating agent like HATU. The left hand portion of the molecule is often derivatized using palladium-mediated reactions, such as a Suzuki reaction. The product can be further modified to introduce other pharmacophores.

Compounds of the present invention can also be prepared according to Scheme 3, as indicated below. Ketones and aldehydes can be reacted with hydrides, Grignard reagents or organolithium reagents to provide alcohols that can be alkylated with an alpha bromo ester in the presence of sodium hydride in DM. The ester can be hydrolyzed under aqueous conditions or under anhydrous conditions. After amide formation with a dehydrating agent, the molecule can be further modified to introduce other pharmacophores.

Scheme 1

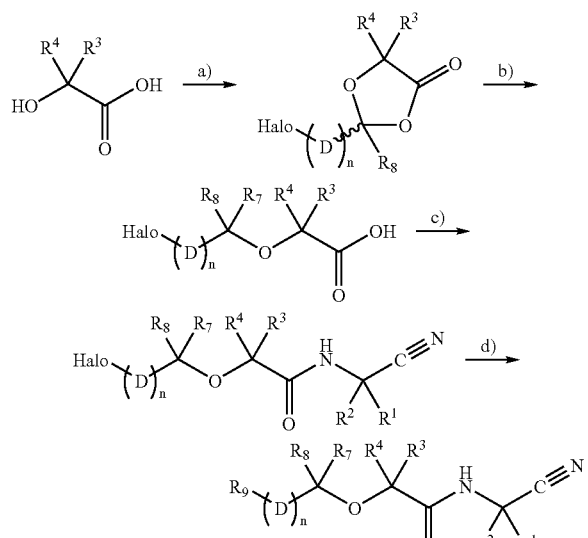

a) Halo(D)$_n$COR$_8$, PPTS, heat, toluene b) R$_7$MgBr, ZnCl$_2$, -30 C. to r.t., diethylether c) H$_2$NCR$_1$R$_2$CN, HATU, triethylamine, DMF d) R$_9$(D)$_n$B(OH)$_2$, PdCl$_2$dppf·CH$_2$Cl$_2$, 2M Na$_2$CO$_3$, DMF, Heat Scheme 3

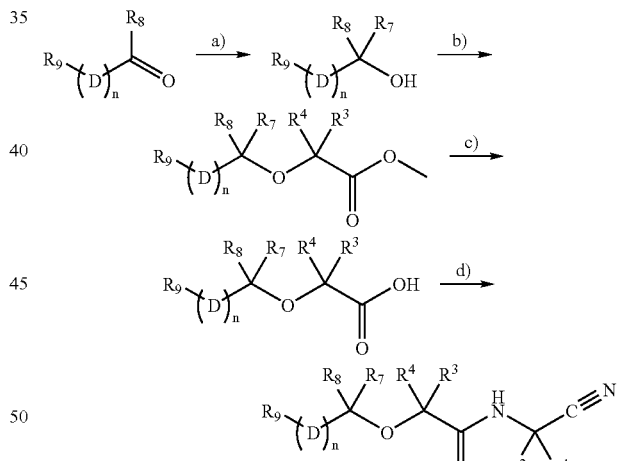

a) R$_7$Br, BuLi or Magnesium, THF or Et$_2$O b) NaH, BrCR$_3$R$_4$COOMe, DMF c) LiOH, THF, H$_2$O, MeOH, r.t. or LiI, pyridine, heat d) H$_2$NCR$_1$R$_2$CN, HATU, Et$_3$N, DMF Compounds of the present invention can also be prepared according to Scheme 2, as indicated below. Alcohols can be derivatized to make the corresponding tricholoacethimdate with a catalytic amount of sodium hydride in ether provided that the reaction is quite concentrated. In parallel, an alpha-hydroxy acid undergoes amide formation in the presence of a dehydrating agent like HATU. The hydroxynitrile thus As shown in scheme 4, sulfur derivatives comprised in the present invention have been prepared from the starting bromide corresponding to alcohols shown below. Triisopropylsilanethiol is a convenient source of sulfur and it may be used in a sequential one-pot double nucleophilic displacement to give the thioether. The ester functionality is saponified and the resulting acid can be coupled in the usual fashion with HATU to afford the amide. The molecule can be further modified to introduce other pharmacophores. Oxidation of the sulfur atom to a higher oxidation state can be performed before or after introduction of the pharmacophores, depending on the functionality introduced.

Scheme 4

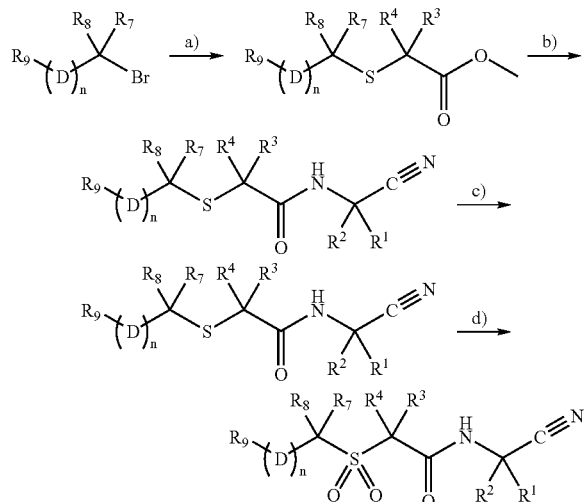

a) (i-Pr)₃SiSH, NaH then BrCR₃R₄COOMe then TBAF, DMF, r.t. b) LiOH, THF, H₂O, MeOH, r.t c) H₂NCR₁R₂CN, HATU, Et₃N, DMF d) MMPP, CH₂Cl₂ MeOH

EXAMPLE 1

Synthesis of (2S)-2-{[(R)-(4-bromophenyl)(phenyl)methyl]oxy}-N-(cyanomethyl)-4-methylpentanamide Step 1 (5S)-2-(4-bromophenyl)-5-isobutyl-1,3-dioxolan-4-one (2S)-2-hydroxy-4-methylpentanoic acid (46.4 g, 351 mmol) and 4-bromobenzaldehyde (50 g, 270.2 mmol) were dissolved in 400 ml toluene and pyridinium 4-methylbenzenesulfonate (340 mg, 1.35 mmol) was added. The mixture was refluxed in a Dean-Stark for 24 hours. The mixture was cooled, poured into 500 ml NaHCO₃(sat) and 500 ether, the phases were separated and the organic phase washed with 500 ml NaHCO₃(sat.) and brine. The organic phase was dried with Na₂SO₄ and the solvent striped. 400 ml Hexane was added to the resulting solid and the mixture was stirred 1 hour in salt ice bath. The solution was filtered thru Celite, and the solvent removed. (5S)-2-(4-bromophenyl)-5-isobutyl-1,3-dioxolan-4-one (3:2 mixture of cis/trans) was obtained.

Step 2 (2S)-2-{[(R)-(4-bromophenyl)(phenyl)methyl]oxy}-4-methylpentanoic acid

Zinc chloride (1.12 l of 1M solution in ether, 1120 mmol) was added to 500 ml ether at −40° C. (5S)-2-(4-bromophenyl)-5-isobutyl-1,3-dioxolan-4-one (3:2 mixture of cis/trans) (56 g, 187 mmol) was then added dropwise in 200 ml ether (over 15 min), followed by phenylmagnesium bromide (125 ml of a 3M solution in ether, 374 mmol) (dropwise over 45 min). The solution was stirred at 0° C. for 2 hours. The reaction was quenched at 0° C. with 800 ml of a saturated solution of NH₄Cl, the phases were separated and the aqueous layer extracted with 800 ml ether. The organic layers were combined, washed with brine, dried with MgSO₄ and the solvent was removed. (2S)-2-{[(R)-(4-bromophenyl)(phenyl)methyl]oxy}-4-methylpentanoic acid (de=86%) was obtained after purification on silica gel (5% ethyl acetate/toluene).

Step 3 (2S)-2-{[(R)-(4-bromophenyl)(phenyl)methyl]oxy}-N-(cyanomethyl)-4-methylpentanamide (2S)-2-{[(R)-(4-bromophenyl)(phenyl)methyl]oxy}-4-methylpentanoic acid (46.5 g, 123 mmol) was dissolved in DMF (200 mL). To this mixture was added HATU (56.7 g, 149 mmol, 1.2 eg), Et₃N (57.7 g, 570 mmol, 4.6 eg), then added at 0° C. aminoacetonitrile hydrochloride (13.5 g, 146 mmol, 1.19 eg). The resulting reaction mixture was stirred at room temperature for 3 hours; then poured into 1 L of half saturated sodium bicarbonate. The aqueous phase was extracted with EtOAc (2×500 mL). Organic fraction was washed with brine (200 mL), 1N HCl (200 mL), brine (200 mL), 0.5 N NaOH (300 mL), brine (200 mL). Solvent was evaporated under reduced pressure and the resulting dark red oil which was chromatographed with 20% EA/hexane to give the title compound.

MS (−APCI): 413.0 [M−1]⁻

EXAMPLE 2

Synthesis of (2S)-N-(cyanomethyl)-4-methyl-2-{[(R)-phenyl(4'-piperazin-1-yl-1,1'-biphenyl-4-yl)methyl]oxy}pentanamide (2S)-2-{[(R)-(4-bromophenyl)(phenyl)methyl]oxy}-N-(cyanomethyl)-4-methylpentanamide (1 g, 2.41 mmol) 1-[4-(dihydroxyboryl)phenyl]piperazin-4-ium chloride (642 mg, 2.65 mmol), PdCl₂(dppf) (88 mg, 0.120 mmol) and 2M Na₂CO₃ (4.8 ml, 9.63 mmol) were dissolved in 25 ml DMF, the solution was degassed 3 times and heated for 10 h @ 85° C. The solution was cooled, poured into 125 ml NaHCO₃ (sat.) and the product extracted with 3×25 ml ethyl acetate. The combined organic layers were then washed with 4× water, then dried with Na₂SO₄. The product was then purified on silica gel (5% MeOH/5% NH4OH/90% DCM).

MS (−APCI): 495.3 [M−1]⁻

EXAMPLE 3

Synthesis of (2S)-N-(cyanomethyl)-4-methyl-2-{[(R)-phenyl(4'-pyridin-4-yl-1,1'-biphenyl-4-yl)methyl]oxy}pentanamide Step 1 4-(4-bromophenyl)pyridine Pyridin-4-ylboronic acid (500 mg, 4.07 mmol), 1-bromo-4-iodobenzene (1.27 g, 4.47 mmol) and 2M Na₂CO₃ (6.1 ml, 12.2 mmol) were dissolved in 20 ml DMF and the solution was degassed 3 times. PdCl₂(dppf) (149 mg, 0.203 mmol) was added and the mixture was stirred overnight at 80° C. The solution was cooled, poured into 100 ml NaHCO₃ (sat.) and extracted 3 times with 20 ml ethyl acetate. The combined organic layers were then washed with 4× water, then dried with Na₂SO₄. 4-(4-bromophenyl)pyridine was obtained and used without further purification.

Step 2 (2S)-N-(cyanomethyl)-4-methyl-2-({(R)-phenyl[4-(4,4,5,5-tetramethyl-1,3,2-dioxaborolan-2-yl)phenyl]methyl}oxy)pentanamide (2S)-2-{[(R)-(4-bromophenyl)(phenyl)methyl]oxy}-N-(cyanomethyl)-4-methylpentanamide from Example 1 (692 mg, 1.67 mmol), 4,4,4',4',5,5,5',5'-octamethyl-2,2'-bi-1,3,2-dioxaborolane (444 mg, 1.75 mmol), KOAc (492 mg, 5.01 mmol) and PdCl$_2$(dppf) were dissolved in 8 ml DMF. The solution was degassed 3 times and heated to 80° C. overnight. The solution was cooled, poured into 40 ml brine and the product extracted with 3×5 ml ethyl acetate. The combined organic layers were then washed with 4× water, then dried with Na$_2$SO$_4$. (2S)-N-(cyanomethyl)-4-methyl-2-({(R)-phenyl[4-(4,4,5,5-tetramethyl-1,3,2-dioxaborolan-2-yl)phenyl]methyl}oxy)pentanamide was obtained after purification on silica gel (40% ethyl acetate/hexanes).

Step 3 (2S)-N-(cyanomethyl)-4-methyl-2-{[(R)-phenyl(4'-pyridin-4-yl-1,1'-biphenyl-4-yl)methyl]oxy}pentanamide (2S)-N-(cyanomethyl)-4-methyl-2-({(R)-phenyl[4-(4,4,5,5-tetramethyl-1,3,2-dioxaborolan-2-yl)phenyl]methyl}oxy)pentanamide (100 mg, 0.216 mmol), 4-(4-bromophenyl)pyridine (56 mg, 0.238 mmol) and 2M K$_2$CO$_3$ (324 ul, 0.648 mmol) were dissolved in 1.6 ml DMF and the solution was degassed 3 times. PdCl$_2$(dppf) (4.8 mg, 0.03 mmol) was added and the mixture was stirred overnight at 80° C. The solution was cooled, poured into 8 ml NaHCO$_3$ (sat.) and extracted 3 times with 2 ml ethyl acetate. The combined organic layers were then washed with 4× water, then dried with Na$_2$SO$_4$. (2S)-N-(cyanomethyl)-4-methyl-2-{[(R)-phenyl(4'-pyridin-4-yl-1,1'-biphenyl-4-yl)methyl]oxy}pentanamide was obtained after purification on silica gel (2% MeOH/38% ethyl acetate/60% hexanes).
MS (+APCI): 490.3 [M+1]$^+$

EXAMPLE 4

Synthesis of (2S)-N-(cyanomethyl)-2-{[(R)-[4'-(1H-imidazol-1-yl)-1,1'-biphenyl-4-yl](phenyl)methyl]oxy}-4-methylpentanamide Following Step 3 of Example 3, the title compound was synthesized using 1-(4-bromophenyl)-1H-imidazole instead of 4-(4-bromophenyl)pyridine.
MS (+APCI): 479.1 [M+1]$^+$

EXAMPLE 5

Synthesis of (2S)-2-({(R)-(4-bromophenyl)[4-(methylsulfonyl)phenyl]methyl}oxy)-N-(cyanomethyl)-4-methylpentanamide Step 1 (2S)-2-({(R)-(4-bromophenyl)[4-(methylthio)phenyl]methyl}oxy)-4-methylpentanoic acid Following Step 2 of Example 1, the title compound was synthesized using bromo[4-(methylthio)phenyl]magnesium instead of phenylmagnesium bromide.

Step 2 (2S)-2-({(R)-(4-bromophenyl)[4-(methylsulfonyl)phenyl]methyl}oxy)-4-methylpentanoic acid (2S)-2-({(R)-(4-bromophenyl)[4-(methylthio)phenyl]methyl}oxy)-4-methylpentanoic acid (103 mg, 0.243 mmol) (from Step 1) was dissolved in 2.5 ml DCM at 0° C. and mCPBA (55-86%) (84 mg) was added, the solution was stirred for 1 hour and an additional 42 mg of mCPBA was added. After stirring for 1 hour the solvent was stripped and (2S)-2-({(R)-(4-bromophenyl)[4-(methylsulfonyl)phenyl]methyl}oxy)-4-methylpentanoic acid was obtained after purification on silica gel (1% AcOH/39% ethyl acetate/60% Hexanes).

Step 3 (2S)-2-({(R)-(4-bromophenyl)[4-(methylsulfonyl)phenyl]methyl}oxy)-N-(cyanomethyl)-4-methylpentanamide Following Step 3 of Example 1, the title compound was synthesized using (2S)-2-({(R)-(4-bromophenyl)[4-(methylsulfonyl)phenyl]methyl}oxy)-4-methylpentanoic acid (from Step 2) instead of (2S)-2-{[(R)-(4-bromophenyl)(phenyl)methyl]oxy}-4-methylpentanoic acid.
MS (−APCI): 491.2 [M−1]$^-$

EXAMPLE 6

Synthesis of (2S)-N-(cyanomethyl)-4-methyl-2-{[(S)-[4-(methylsulfonyl)phenyl](4'-piperazin-1-yl-1,1'-biphenyl-4-yl)methyl]oxy}pentanamide Following Step 1 of Example 2, the title compound was synthesized using (2S)-2-({(R)-(4-bromophenyl)[4-(methylsulfonyl)phenyl]methyl}oxy)-N-(cyanomethyl)-4-methylpentanamide instead of (2S)-2-{[(R)-(4-bromophenyl)(phenyl)methyl]oxy}-N-(cyanomethyl)-4-methylpentanamide.
MS (+APCI): 575.3 [M+1]$^+$

EXAMPLE 7

Synthesis of (2S)-2-{[(R)-(4-bromophenyl)(4-chlorophenyl)methyl]oxy}-N-(cyanomethyl)-4-methylpentanamide Step 1 (2S)-2-{[(R)-(4-bromophenyl)(4-chlorophenyl)methyl]oxy}-4-methylpentanoic acid Following Step 2 of Example 1, the title compound was synthesized using bromo(4-chlorophenyl)magnesium instead of phenylmagnesium bromide.

Step 2 (2S)-2-{[(R)-(4-bromophenyl)(4-chlorophenyl)methyl]oxy}-N-(cyanomethyl)-4-methylpentanamide Following Step 3 of Example 1, the title compound was synthesized using (2S)-2-{[(R)-(4-bromophenyl)(4-chlorophenyl)methyl]oxy}-4-methylpentanoic acid (from Step 1) instead of (2S)-2-{[(R)-(4-bromophenyl)(phenyl)methyl]oxy}-4-methylpentanoic acid.
MS (−APCI): 447.0 [M−1]$^-$

EXAMPLE 8

Synthesis of (2S)-2-{[(S)-(4-chlorophenyl)(4'-piperazin-1-yl-1,1'-biphenyl-4-yl)methyl]oxy}-N-(cyanomethyl)-4-methylpentanamide Following Step 1 of Example 2, the title compound was synthesized using (2S)-2-{[(R)-(4-bromophenyl)(4-chlorophenyl)methyl]oxy}-N-(cyanomethyl)-4-methylpentanamide instead of (2S)-2-{[(R)-(4-bromophenyl)(phenyl)methyl]oxy}-N-(cyanomethyl)-4-methylpentanamide.

MS (+APCI): 531.2 [M+1]$^+$

EXAMPLE 9

Synthesis of (2S)-2-{[(S)-(4-bromophenyl)(mesityl)methyl]oxy}-N-(cyanomethyl)-4-methylpentanamide Step 1 (2S)-2-{[(S)-(4-bromophenyl)(mesityl)methyl]oxy}-4-methylpentanoic acid Following Step 2 of Example 1, the title compound was synthesized using bromo(mesityl)magnesium instead of phenylmagnesium bromide.

Step 2 (2S)-2-{[(S)-(4-bromophenyl)(mesityl)methyl]oxy}-N-(cyanomethyl)-4-methylpentanamide Following Step 3 of Example 1, the title compound was synthesized using (2S)-2-{[(S)-(4-bromophenyl)(mesityl)methyl]oxy}-4-methylpentanoic acid (from Step 1) instead of (2S)-2-{[(R)-(4-bromophenyl)(phenyl)methyl]oxy}-4-methylpentanoic acid.

MS (−APCI): 455.1 [M−1]$^-$

EXAMPLE 10

(2S)-N-(cyanomethyl)-2-{[(S)-mesityl(4'-piperazin-1-yl-1,1'-biphenyl-4-yl)methyl]oxy}-4-methylpentanamide Following Step 1 of Example 2, the title compound was synthesized using (2S)-2-{[(S)-(4-bromophenyl)(mesityl)methyl]oxy}-N-(cyanomethyl)-4-methylpentanamide instead of (2S)-2-{[(R)-(4-bromophenyl)(phenyl)methyl]oxy}-N-(cyanomethyl)-4-methylpentanamide.

MS (+APCI): 539.4 [M+1]$^+$

EXAMPLE 11

Preparation of (2S)-2-{[(1R)-1-(4-bromophenyl)-2-(4-chlorophenyl)ethyl]oxy}-N-(cyanomethyl)-4-methylpentanamide Step 1 (2S)-2-{[(1R)-1-(4-bromophenyl)-2-(4-chlorophenyl)ethyl]oxy}-4-methylpentanoic acid Following Step 2 of Example 1, the title compound was synthesized using bromo(4-chlorobenzyl)magnesium is used instead of phenylmagnesium bromide.

Step 2 (2S)-2-{[(1R)-1-(4-bromophenyl)-2-(4-chlorophenyl)ethyl]oxy}-N-(cyanomethyl)-4-methylpentanamide Following Step 3 of Example 1, the title compound was synthesized using (2S)-2-{[(1R)-1-(4-bromophenyl)-2-(4-chlorophenyl)ethyl]oxy}-4-methylpentanoic acid (from Step 1) instead of (2S)-2-{[(R)-(4-bromophenyl)(phenyl)methyl]oxy}-4-methylpentanoic acid.

MS (−APCI): 461.2 [M−1]$^-$

EXAMPLE 12

Preparation of (2S)-2-{[(1R)-1-(4-bromophenyl)-2-(4-chlorophenyl)ethyl]oxy}-N-(cyanomethyl)-4-methylpentanamide Step 1 (2S)-2-{[(1R)-1-(4-bromophenyl)-2-(4-chlorophenyl)ethyl]oxy}-N-(cyanomethyl)-4-methylpentanamide Following Step 2 of Example 1, the title compound was synthesized using bromo(cyclopropylmethyl)magnesium instead of phenylmagnesium bromide.

Step 2 (2S)-2-{[(R)-(4-bromophenyl)(cyclopropyl)methyl]oxy}-4-methylpentanoic acid Following Step 3 of Example 1, the title compound was synthesized using (2S)-2-{[(R)-(4-bromophenyl)(cyclopropyl)methyl]oxy}-4-methylpentanoic acid (from Step 1) instead of (2S)-2-{[(R)-(4-bromophenyl)(phenyl)methyl]oxy}-4-methylpentanoic acid.

MS (−APCI): 477.2 [M−1]$^-$

EXAMPLE 13

Synthesis of (2S)-2-(benzhydryloxy)-N-(cyanomethyl)-4-methylpentanamide

Step 1 (5S)-5-isobutyl-2-phenyl-1,3-dioxolan-4-one

Following Step 1 of Example 1, the title compound was synthesized using benzaldehyde instead of 4-bromobenzaldyde.

Step 2 (2S)-2-(benzhydryloxy)-4-methylpentanoic acid

Following Step 2 of Example 1, the title compound was synthesized using (5S)-5-isobutyl-2-phenyl-1,3-dioxolan-4-one instead of (5S)-2-(4-bromophenyl)-5-isobutyl-1,3-dioxolan-4-one.

Step 3 (2S)-2-(benzhydryloxy)-N-(cyanomethyl)-4-methylpentanamide

Following Step 3 of Example 1, the title compound was synthesized (2S)-2-(benzhydryloxy)-4-methylpentanoic acid (from Step 2) was used instead of (2S)-2-{[(R)-(4-bromophenyl)(phenyl)methyl]oxy}-4-methylpentanoic acid.

MS (−APCI): 335.1 [M−1]$^-$

EXAMPLE 14

Synthesis of (2S)-2-{[(R)-(3-bromophenyl)(phenyl)methyl]oxy}-N-(cyanomethyl)-4-methylpentanamide Step 1 (5S)-2-(3-bromophenyl)-5-isobutyl-1,3-dioxolan-4-one Following Step 1 of Example 1, the title compound was synthesized using 3-bromobenzaldehyde bromobenzaldehyde instead of 4-bromobenzaldyde.

Step 2 (2S)-2-{[(R)-(3-bromophenyl)(phenyl)methyl]oxy}-4-methylpentanoic acid Following Step 2 of Example 1, the title compound was synthesized using (5S)-2-(3-bromophenyl)-5-isobutyl-1,3-dioxolan-4-one (from Step 1) instead of (5S)-2-(4-bromophenyl)-5-isobutyl-1,3-dioxolan-4-one.

Step 3 (2S)-2-{[(R)-(3-bromophenyl)(phenyl)methyl]oxy}-N-(cyanomethyl)-4-methylpentanamide Following Step 3 of Example 1, the title compound was synthesized using (2S)-2-{[(R)-(3-bromophenyl)(phenyl)methyl]oxy}-4-methylpentanoic acid (from Step 2) instead of (2S)-2-{[(R)-(4-bromophenyl)(phenyl)methyl]oxy}-4-methylpentanoic acid.
MS (−APCI): 413.1 [M−1]$^-$

EXAMPLE 15

Synthesis of 1-{[(R)-(4-bromophenyl)(phenyl)methyl]oxy}-N-(cyanomethyl)cyclohexanecarboxamide

Step 1
2-(4-bromophenyl)-1,3-dioxaspiro[4,5]decan-4-one

Following Step 1 of Example 1, the title compound was synthesized using 1-hydroxycyclohexanecarboxylic acid is used instead of (2S)-2-hydroxy-4-methylpentanoic acid.

Step 2 1-[(4-bromophenyl)(phenyl)methoxy]cyclohexanecarboxylic acid

Following Step 2 of Example 1, the title compound was synthesized using 2-(4-bromophenyl)-1,3-dioxaspiro[4.5]decan-4-one (from Step 1) was used instead of (5S)-2-(4-bromophenyl)-5-isobutyl-1,3-dioxolan-4-one.

Step 3 1-{[(R)-(4-bromophenyl)(phenyl)methyl]oxy}-N-(cyanomethyl)cyclohexanecarboxamide Following Step 3 of Example 1, the title compound was synthesized using 1-[(4-bromophenyl)(phenyl)methoxy]cyclohexanecarboxylic acid (from Step 2) instead of (2S)-2-{[(R)-(4-bromophenyl)(phenyl)methyl]oxy}-4-methylpentanoic acid.
MS (−APCI): 425.1 [M−1]$^-$

EXAMPLE 16

Synthesis of (2S)-N-(cyanomethyl)-4-methyl-2-{phenyl[4-(4,4,5,5-tetramethyl-1,3,2-dioxaborolan-2-yl)phenyl]methoxy}pentanamide To a solution of (2S)-2-[(4-bromophenyl)(phenyl)methoxy]-N-(cyanomethyl)-4-methylpentanamide from Example 1 (1 eq.), Bis(pinacolato)diboron (1.3 eq.) and potassium acetate (4 eq.) in DMF (0.2M) was added PdCl$_2$(dppf) dichloromethane complex. The solution was briefly degassed by bubbling nitrogen through the solution and the mixture was heated at 60° C. for 24 h. The reaction was diluted with a 1 to 4 mixture of water and an organic phase made of diethyl ether and ethyl acetate and then separated. The organic phases were dried with brine and solid sodium chloride. The liquor obtained after removal of the volatiles was purified over silica gel (ethyl acetate/dichloromethane). The product solidified on standing.

General Procedure 1

To an aryl bromide (1.4-1.6 eq.), was added (2S)-N-(cyanomethyl)-4-methyl-2-{phenyl[4-(4,4,5,5-tetramethyl-1,3,2-dioxaborolan-2-yl)phenyl]methoxy}pentanamide (1 eq.) in tetrahydrofuran/propanol 4/1 (0.05M) and 2M aqueous sodium carbonate (3 eq.). The solution was briefly degassed by bubbling nitrogen through the solution and a palladium acetate and triphenylphosphine mixture in a 1:3 ratio (0.01-0.15 eq.) was added. The reaction was heated to 80° C. for 24 h. The reaction was cooled down and diluted with dichloromethane (acid acetic was added in the case of an acidic compound) and then filtered through a SPE tube of silica gel. The concentrated liquor was purified on a reverse phase (C$_4$) HPLC-MS column.

The following compounds were synthesized using general procedure 1.

| NAME | CHARACTERIZATION |
|---|---|
| (2S)-2-[[4-(3-chloropyrazin-2-yl)phenyl](phenyl)methoxy]-N-(cyanomethyl)-4-methylpentanamide | MS (−ESI): 447.3 [M − 1]$^-$ |
| (2S)-N-(cyanomethyl)-4-methyl-2-{phenyl[4-(1,3-thiazol-2-yl)phenyl]methoxy}pentanamide | MS (−ESI): 418.4 [M − 1]$^-$ |
| (2S)-2-[[4'-(aminosulfonyl)-1,1'-biphenyl-4-yl](phenyl)methoxy]-N-(cyanomethyl)-4-methylpentanamide | MS (−ESI): 490.4 [M − 1]$^-$ |
| (2S)-N-(cyanomethyl)-4-methyl-2-[[4'-(methylsulfonyl)-1,1'-biphenyl-4-yl](phenyl)methoxy]pentanamide | MS (−ESI): 489.4 [M − 1]$^-$ |
| (2S)-N-(cyanomethyl)-4-methyl-2-[phenyl(4-quinolin-3-yl)phenyl)methoxy]pentanamide | MS (−ESI): 462.4 [M − 1]$^-$ |
| (2S)-N-(cyanomethyl)-4-methyl-2-[phenyl(4-pyrimidin-5-yl)phenyl)methoxy]pentanamide | MS (−ESI): 413.4 [M − 1]$^-$ |
| (2S)-N-(cyanomethyl)-4-methyl-2-[phenyl(4-quinolin-8-yl)phenyl)methoxy]pentanamide | MS (−ESI): 462.4 [M − 1]$^-$ |
| (2S)-N-(cyanomethyl)-2-[{4-[6-(hydroxymethyl)-1-oxidopyridin-3-yl]phenyl}(phenyl)methoxy]-4-methylpentanamide | MS (−ESI): 458.4 [M − 1]$^-$ |
| (2S)-N-(cyanomethyl)-4-methyl-2-[phenyl(4-pyridin-4-yl)phenyl)methoxy]pentanamide | MS (−ESI): 412.4 [M − 1]$^-$ |
| (2S)-N-(cyanomethyl)-2-[[4-(1H-indol-4-yl)phenyl](phenyl)methoxy]-4-methylpentanamide | MS (−ESI): 450.4 [M − 1]$^-$ |
| (2S)-N-(cyanomethyl)-4-methyl-2-[phenyl(4-pyridin-2-yl)phenyl)methoxy]pentanamide | MS (−ESI): 412.3 [M − 1]$^-$ |
| (2S)-N-(cyanomethyl)-4-methyl-2-[phenyl(4-pyrazin-2-yl)phenyl)methoxy]pentanamide | MS (−ESI): 413.5 [M − 1]$^-$ |
| (2S)-N-(cyanomethyl)-4-methyl-2-[phenyl(4-pyridin-3-yl)phenyl)methoxy]pentanamide | MS (−ESI): 412.5 [M − 1]$^-$ |
| (2S)-N-(cyanomethyl)-4-methyl-2-(phenyl{4-[5-(2H-tetraazol-5-yl)pyridin-3-yl]phenyl}methoxy)pentanamide | MS (−ESI): 480.5 [M − 1]$^-$ |
| (2S)-N-(cyanomethyl)-4-methyl-2-[[4-(3-methylpyridin-2-yl)phenyl](phenyl)methoxy]pentanamide | MS (−ESI): 426.5 [M − 1]$^-$ |
| 2-{4-[[((1S)-1-{[(cyanomethyl)amino]carbonyl}-3-methylbutyl)oxy](phenyl)methyl]phenyl}isonicotinic acid | MS (−ESI): 456.5 [M − 1]$^-$ |
| (2S)-N-(cyanomethyl)-4-methyl-2-[phenyl(4-pyrimidin-2-yl)phenyl)methoxy]pentanamide | MS (−ESI): 413.5 [M − 1]$^-$ |
| ethyl 4'-[[((1S)-1-{[(cyanomethyl)amino]carbonyl}-3-methylbutyl)oxy](phenyl)methyl]-1,1'-biphenyl-4-carboxylate | MS (−ESI): 483.4 [M − 1]$^-$ |

-continued

| NAME | CHARACTERIZATION |
|---|---|
| 4'-[[((1S)-1-{[(cyanomethyl)amino]carbonyl}-3-methylbutyl)oxy](phenyl)methyl]-1,1'-biphenyl-4-carboxamide | MS (−ESI): 454.5 [M − 1]⁻ |

EXAMPLE 17

Synthesis of N-(cyanomethyl)-4-methyl-2-{phenyl[4-(piperazin-1-ylcarbonyl)phenyl]methoxy}pentanamide Step 1 methyl 4-[hydroxy(phenyl)methyl]benzoate To a solution of methyl 4-formylbenzoate (2.83 g, 17.2 mmoles) at −78° C. in 60 mL of dichloromethane is added 10 mL a 2.0 M solution of phenylmagnesium chloride in tetrahydrofuran (20.0 mmoles) over 7 minutes. After stirring for an additional 20 minutes, the reaction was quenched with methanol then with saturated aqueous ammonium chloride. The aqueous layer was acidified with 1N hydrochloric acid and the phases were separated. The organic portion was washed with saturated aqueous sodium bicarbonate, brine and dried over magnesium sulfate. Removal of the volatiles under reduced pressure and purification over silica gel afforded the title ester.

Step 2 4-[hydroxy(phenyl)methyl]benzoic acid

To a solution of methyl 4-[hydroxy(phenyl)methyl]benzoate from step 1 (1.6 g, 6.6 mmol) in THF (40 mL) was added methanol (13 mL) and 1.0N aqueous potassium hydroxide solution (13.2 mL, 13.2 mmol). The mixture was heated at 70° C. for 20 minutes and then cooled down to room temperature. Methanol and THF were evaporated under reduced pressure. 3.0N hydrochloric acid (7.5 mL, 22.5 mmol) was added to the crude residue. The solid obtained was filtered to afford the title acid as a white solid. The resulting crude compound was used as such in the next step.

Step 3 tert-butyl 4-{4-[hydroxy(phenyl)methyl]benzoyl}piperazine-1-carboxylate

To a solution of the crude compound of 4-[hydroxy(phenyl)methyl]benzoic acid (1.51 g, 6.6 mmol) in DMF (33 mL) was added tert-butyl piperazine-1-carboxylate (1.23 g, 6.6 mmol), triethylamine (3.7 mL, 26.5 mmol) and HATU (2.51 g, 6.6 mmol). The mixture was aged for 3 hours under a nitrogen atmosphere and was then poured into a saturated aqueous solution of NaHCO₃. The resulting mixture was extracted 3 times with ethyl acetate. The combined organic layers were washed with brine, dried and evaporated to a solid which was stirred in ethyl acetate at room temperature for 2 hours. The title compound was then recovered by filtration as a white solid.

Step 4 tert-butyl 4-{4-[[1-(methoxycarbonyl)-3-methylbutoxy](phenyl)methyl]benzoyl}piperazine-1-carboxylate To a solution of tert-butyl 4-{4-[hydroxy(phenyl)methyl]benzoyl}piperazine-1-carboxylate from step 3 (1.5 g, 3.8 mmol) in DMF (20 mL) at 0° C. was added sodium hydride (0.16 g, 4.0 mmol) portionwise. The mixture was aged 15 minutes under a nitrogen atmosphere and methyl 2-bromo-4-methylpentanoate (0.65 mL, 4.0 mmol) was added dropwise. The reaction was allowed to warm to room temperature and was aged for 3 hours. The mixture was then partitioned between ethyl acetate and brine and the organic layer was dried and evaporated. The crude product was chromatographed on silica gel using 40% ethyl acetate in hexanes to afford the title compound.

Step 5 2-[(4-{[4-(tert-butoxycarbonyl)piperazin-1-yl]carbonyl}phenyl)(phenyl)methoxy]-4-methylpentanoic acid potassium salt To a solution of tert-butyl 4-{4-[[1-(methoxycarbonyl)-3-methylbutoxy](phenyl)methyl]benzoyl}piperazine-1-carboxylate from step 3 (0.6 g, 1.1 mmol) in THF (6.5 mL) was added methanol (2.2 mL) and 1.0N aqueous potassium hydroxide solution (2.2 mL, 2.2 mmol). The mixture was heated at 70° C. for 20 minutes and then cooled down to room temperature. The crude mixture was evaporated under reduced pressure and co-evaporated twice with toluene. The solid residue obtained was used as such in the next step.

Step 6 tert-butyl 4-{4-[(1-{[(cyanomethyl)amino]carbonyl}-3-methylbutoxy)(phenyl)methyl]benzoyl}piperazine-1-carboxylate Using the same procedure as described in step 3, 2-[(4-{[4-(tert-butoxycarbonyl)piperazin-1-yl]carbonyl}phenyl)(phenyl)methoxy]-4-methylpentanoic acid potassium salt from step 4 (0.55 g, 1.1 mmol) was coupled with amino acetonitrile HCl salt. The crude product was chromatographed on silica gel using 5% methanol in dichloromethane to afford the title compound as a white solid.

Step 7 N-(cyanomethyl)-4-methyl-2-{phenyl[4-(piperazin-1-ylcarbonyl)phenyl]methoxy}pentanamide Tert-butyl 4-{4-[(1-{[(cyanomethyl)amino]carbonyl}-3-methylbutoxy)(phenyl)methyl]benzoyl}piperazine-1-carboxylate from step 6 (0.09 g, 0.16 mmol) was dissolved in formic acid (1 mL). The mixture was aged for 2 hours and evaporated under reduced pressure. The crude residue was neutralized using a saturated aqueous solution of NaHCO₃. The mixture was extracted 3 times with dichloromethane and the organic layers were dried and evaporated. The crude product was chromatographed on silica gel using 1% NH₄OH and 9% methanol in dichloromethane to afford the title compound as a white solid.
MS (+APCI) 449.1 [M+1]⁺

EXAMPLE 18

Synthesis of N-(cyanomethyl)-2-[(4-{[4-(2-fluoroethyl)piperazin-1-yl]carbonyl}phenyl)(phenyl)methoxy]-4-methylpentanamide To a solution of N-(cyanomethyl)-4-methyl-2-{phenyl[4-(piperazin-1-ylcarbonyl)phenyl]methoxy}pentanamide from example 17, step 7 (79 mg, 0.18 mmol) in acetonitrile (1 mL), was added Na₂CO₃ (37 mg, 0.36 mmol) and 2-bromofluoroethane (39 µL, 0.525 mmol). The reaction was heated in a sealed tube at 85° C. for 16 hours and was then cooled down to room temperature. The mixture was then concentrated and the crude residue chromatographed on silica gel using 1% NH₄OH and 9% methanol in dichloromethane to afford the title compound.
MS (−ESI) 493.1 [M−1]⁻

EXAMPLE 19

Preparation of L-000873736-000G001

Synthesis of N-(cyanomethyl)-4-methyl-2-[(4-{[4-(methylsulfonyl)piperazin-1-yl]carbonyl}phenyl)(phenyl)methoxy]pentanamide To a solution of N-(cyanomethyl)-4-methyl-2-{phenyl[4-(piperazin-1-ylcarbonyl)phenyl]methoxy}pentanamide from example 17, step 7 (102 mg, 0.23 mmol) in DMF (1 mL), was added methyl sulfonyl chloride (27 μL, 0.35 mmol) and cesium carbonate (91 mg, 0.28 mmol). The mixture was aged for 2 hours under nitrogen atmosphere and was diluted with dichloromethane. The resulting mixture was filtered over celite and concentrated under reduced pressure. The crude residue was chromatographed on silica gel using 1% NH₄OH and 9% methanol in dichloromethane to afford the title compound.
MS (−APCI) 525.3 [M−1]⁻

EXAMPLE 20

Synthesis of (2S)-2-{[(S)-(4-bromophenyl)(thien-2-yl)methyl]oxy}-N-(cyanomethyl)-4-methylpentanamide Step 1 (5S)-2-(4-bromophenyl)-5-isobutyl-1,3-dioxolan-4-one The title compound was prepared following Step 1 of Example 1.

Step 2 (2S)-2-{[(S)-(4-bromophenyl)(thien-2-yl)methyl]oxy}-4-methylpentanoic acid To a solution of 2-bromothiophene (326 mg, 2.0 mmol) in ether (8 mL) was added magnesium turnings (51 mg, 2.1 mmol). The mixture was heated at 50° C. for 1 hour, under a nitrogen atmosphere. The grignard solution was then cooled down to −40° C. and aged until addition. In a second flask, cooled at −40° C., a 0.2M solution of (5S)-2-(4-bromophenyl)-5-isobutyl-1,3-dioxolan-4-one in ether, from step 1 (5.0 mL, 1.0 mmol) was added dropwise to a 1.0M solution of zinc chloride in ether (5.0 mL, 5 mmol). Finally, the grignard solution was added dropwise to the zinc chloride mixture and the reaction was aged for 30 minutes at −40° C. The mixture was allowed to warm to 0° C. and aged for 4 hours. The reaction was then poured into a saturated aqueous solution of NH₄Cl and the resulting mixture was extracted 3 times with Et₂O. The organic layers were washed with brine, dried and evaporated. The crude product was chromatographed on silica gel using 30% ethyl acetate in hexanes to afford the title compound.

Step 3 (2S)-2-{[(S)-(4-bromophenyl)(thien-2-yl)methyl]oxy}-N-(cyanomethyl)-4-methylpentanamide To a solution of (2S)-2-{[(S)-(4-bromophenyl)(thien-2-yl)methyl]oxy}-4-methylpentanoic acid from step 2, (273 mg, 0.71 mmol) in DMF (3.5 mL) was added aminoacetonitrile HCL salt (66 mg, 0.71 mmol), triethylamine (359 μL, 3.55 mmol) and HATU (270 mg, 0.71 mmol). The mixture was aged for 3 hours under a nitrogen atmosphere and was then poured into a saturated aqueous solution of NaHCO₃. The resulting mixture was extracted 3 times with ethyl acetate. The organic extracts were washed with brine, dried and evaporated to a solid. The crude product was chromatographed on silica gel using 35% ethyl acetate in hexanes to afford the title compound.
¹H NMR (500 MHz, DMSO-d₆) δ (ppm): (8.7-8.6, m, 1H); (7.6, d, 3H); (7.4, d, 2H); (7.1, s, 1H); (7.0, t, 1H); (5.7, s, 1H); (4.1, d, 2H); (3.9-3.8, m, 1H); (1.8-1.7, m, 1H); (1.7-1.6, m, 1H); (1.4-1.3, m, 1H); (0.9, d, 3H); (0.7, d, 3H).

EXAMPLE 21

Synthesis of (2S)-N-(cyanomethyl)-4-methyl-2-{[(S)-(4'-piperazin-1-yl-1,1'-biphenyl-4-yl)(thien-2-yl)methyl]oxy}pentanamide To a solution of (2S)-2-{[(S)-(4-bromophenyl)(thien-2-yl)methyl]oxy}-N-(cyanomethyl)-4-methylpentanamide, from example 20, step 3 (113 mg, 0.27 mmol) in DMF (3 mL) was added 4-piperazin-1-ylphenylboronic acid (73 mg, 0.30 mmol), and a 2.0M aqueous solution of Na₂CO₃ (0.54 mL, 1.08 mmol). The mixture was placed under vacuum and purged with nitrogen 3 times before the PdCl₂(dppf)₂ was added (10 mg, 0.014 mmol). The reaction mixture was purged 3 other times with nitrogen and the reaction was heated to 85° C. for 16 hours. The mixture was then diluted with dichloromethane and filtered over celite. The organic layer was isolated and washed with a saturated solution of NaHCO₃ and brine, dried and evaporated. The crude residue was chromatographed on silica gel using 1% NH₄OH and 9% methanol in dichloromethane to afford the title compound.
MS (+APCI) 503.1 [M+1]⁺

EXAMPLE 22

Synthesis of (2S)-2-[(4-bromophenyl)(thien-3-yl)methoxy]-N-(cyanomethyl)-4-methylpentanamide Step 1 (4-bromophenyl)(thien-3-yl)methanol To a solution of 1.5M BuLi in hexanes (3.5 mL, 5.25 mmol) in THF (6.5 mL) cooled to −78° C. was added 3-bromothiophene dropwise (469 μL, 5.0 mmol). The mixture was stirred for 30 minutes and a 1.0M solution of 4-bromobenzaldehyde in THF was slowly added (5.5 mL, 5.5 mmol). The reaction was warmed to 0° C. and aged for 1 hour. The mixture was then poured into a saturated aqueous solution of NH₄Cl. The resulting mixture was extracted 3 times with ethyl acetate and the organic layers were washed with brine, dried and evaporated. The crude residue was chromatographed on silica gel using a gradient of 10-25% ethyl acetate in hexanes to afford the title compound.

Step 2 (4-bromophenyl)(thien-3-yl)methyl 2,2,2-trichloroethanimidoate

To a solution of (4-bromophenyl)(thien-3-yl)methanol from step 1 (632 mg, 2.36 mmol) in diethyl ether (2.5 mL) at 0° C. was added sodium hydride (6 mg, 0.24 mmol). Then trichloroacetonitrile was added dropwise (237 μL, 2.36 mmol) over 15 minutes and the reaction was allowed to warm to room temperature for 3 hours. The reaction was then filtered over celite and concentrated under reduced pressure. The resulting crude compound was used as such in the next step.

Step 3 (2S)-2-[(4-bromophenyl)(thien-3-yl)methoxy]-N-(cyanomethyl)-4-methylpentanamide To a solution of (4-bromophenyl)(thien-3-yl)methyl 2,2,2-trichloroethanimidoate from step 2 (970 mg, 2.36 mmol) in dichloromethane (12 mL) was added (2S)-N-(cyanomethyl)-2-hydroxy-4-methylpentanamide (402 mg, 2.36 mmol) and camphorsulfonic acid (137 mg, 0.59 mmol). The reaction was stirred overnight at room temperature and the resulting mixture was poured into water. The aqueous layer was extracted 3 times with ethyl acetate. The combined organic layers were washed with brine, dried and evaporated and the crude residue was chromatographed on silica gel using 50% ethyl acetate in hexanes to afford the title compound.

MS (−APCI) 419.0 [M−1]−

EXAMPLE 23

Synthesis of 2-[(4-bromophenyl)(pyridin-2-yl)methoxy]-N-(cyanomethyl)-4-methylpentanamide Step 1 (4-bromophenyl)(pyridin-2-yl)methanol Using the same protocol as described in example 22, step 1, 2-bromopyridine (477 µL, 5.0 mmol) was added to 4-bromobenzaldehyde (1.018 g, 5.5 mmol). The crude residue obtained was chromatographed on silica gel using 50% ethyl acetate in hexanes to afford the title compound.

Step 2 methyl 2-[(4-bromophenyl)(pyridin-2-yl)methoxy]-4-methylpentanoate

To a solution of (4-bromophenyl)(pyridin-2-yl)methanol from step 1 (720 mg, 2.73 mmol) in DMF (14 mL) at 0° C., was added sodium hydride portionwise (69 mg, 2.87 mmol). The mixture was stirred 30 minutes before the methyl 2-bromo-4-methylpentanoate was slowly added (469 µL, 2.87 mmol). The reaction was allowed to warm to room temperature and was aged for 3 hours more. The mixture was then poured into brine and extracted 3 times with ethyl acetate. The combined organic extracts were dried and concentrated and the crude product obtained was chromatographed on silica gel using 50% ethyl acetate in hexanes to afford the title compound.

Step 3 2-[(4-bromophenyl)(pyridin-2-yl)methoxy]-4-methylpentanoic acid potassium salt Using the same protocol as described in example 17, step 5, methyl 2-[(4-bromophenyl)(pyridin-2-yl)methoxy]-4-methylpentanoate from step 2 (623 mg, 1.59 mmol) was hydrolysed with potassium hydroxide. The solid residue obtained was used as such in the next step.

Step 4 2-[(4-bromophenyl)(pyridin-2-yl)methoxy]-N-(cyanomethyl)-4-methylpentanamide Using the same protocol as described in example 17, step 3, 2-[(4-bromophenyl)(pyridin-2-yl)methoxy]-4-methylpentanoic acid potassium salt from step 3 (662 mg, 1.59 mmol) was coupled with aminoacetonitrile HCl Salt. The crude residue obtained was chromatographed on silica gel using 50% ethyl acetate in hexanes to afford the title compound.

$^1$H NMR (500 MHz, DMSO-$d_6$) δ (ppm) mixture of 4 diastereoisomers: (9.6, bs, 1H); (8.7, d, 1H); (8.5, d, 1H); (8.1, bs, 1H); (7.9-7.8, m, 2H); (7.7-7.6, m, 3H); (7.5-7.4, m, 6H); (7.4-7.3, m, 2H); (7.2, d, 1H); (5.65, s, 1H); (5.6, s, 1H); (4.3, d, 2H); (4.2, d, 2H); (4.0-3.9, m, 2H); (2.9-2.8, m, 1H); (2.8-2.6, m, 3H); (1.6-1.5, m, 2H); (1.95, d, 3H); (1.9, d, 3H); (1.75, 3H); (1.65, 3H).

EXAMPLE 24

Synthesis of 2-[(4-bromophenyl)(pyridin-3-yl)methoxy]-N-(cyanomethyl)-4-methylpentanamide Step 1 (4-bromophenyl)(pyridin-3-yl)methanol Using the same protocol as described in example 22, step 1, 3-bromopyridine (482 µL, 5.0 mmol) was added to 4-bromobenzaldehyde (1.018 g, 5.5 mmol). The crude residue was chromatographed on silica gel using 1% NH$_4$OH and 9% MeOH in dichloromethane to afford the title compound.

Step 2 methyl 2-[(4-bromophenyl)(pyridin-3-yl)methoxy]-4-methylpentanoate

Using the same protocol as described in example 23, step 2, (4-bromophenyl)(pyridin-3-yl)methanol from step 1 (644 mg, 2.4 mmol) was added to methyl 2-bromo-4-methylpentanoate (412 µL, 2.52 mmol). The crude residue was chromatographed on silica gel using 50% ethyl acetate in hexanes to afford the title compound.

Step 3 2-[(4-bromophenyl)(pyridin-3-yl)methoxy]-4-methylpentanoic acid potassium salt Using the same protocol as described in example 17, step 5, methyl 2-[(4-bromophenyl)(pyridin-3-yl)methoxy]-4-methylpentanoate from step 2 (268 mg, 0.68 mmol) was hydrolysed with potassium hydroxide. The solid residue obtained was used as such in the next step.

Step 4 2-[(4-bromophenyl)(pyridin-3-yl)methoxy]-N-(cyanomethyl)-4-methylpentanamide Using the same protocol as described in example 17, step 3, 2-[(4-bromophenyl)(pyridin-3-yl)methoxy]-4-methylpentanoic acid potassium salt from step 3 (132 mg, 0.35 mmol) was coupled with aminoacetonitrile HCl Salt. The crude residue obtained was chromatographed on silica gel using 10% MeOH in dichloromethane to afford the title compound.

MS (−ESI) 414.2 [M−1]−

EXAMPLE 25

Synthesis of 2-[(4-bromophenyl)(pyridin-4-yl)methoxy]-N-(cyanomethyl)-4-methylpentanamide Step 1 4-bromophenyl)(pyridin-4-yl)methanol Using the same protocol as described in example 22, step 1, 4-bromopyridine (790 mg, 5.0 mmol) was added to 4-bromobenzaldehyde (1.018 g, 5.5 mmol). The crude residue was chromatographed on silica gel using 1% NH$_4$OH and 9% MeOH in dichloromethane to afford the title compound.

Step 2 methyl 2-[(4-bromophenyl)(pyridin-4-yl)
methoxy]-4-methylpentanoate

Using the same protocol as described in example 23, step 2, (4-bromophenyl)(pyridin-4-yl)methanol from step 1 (594 mg, 2.20 mmol) was added to methyl 2-bromo-4-methylpentanoate (377 μL, 2.31 mmol). The crude residue was chromatographed on silica gel using 50% ethyl acetate in hexanes to afford the title compound.

Step 3 2-[(4-bromophenyl)(pyridin-4-yl)methoxy]-
4-methylpentanoic acid potassium salt Using the same protocol as described in example 17, step 5, methyl 2-[(4-bromophenyl)(pyridin-4-yl)methoxy]-4-methylpentanoate from step 2 (293 mg, 0.75 mmol) was hydrolysed with potassium hydroxide. The solid residue obtained was used as such in the next step.

Step 4 2-[(4-bromophenyl)(pyridin-4-yl)methoxy]-
N-(cyanomethyl)-4-methylpentanamide Using the same protocol as described in example 17, step 3, 2-[(4-bromophenyl)(pyridin-4-yl)methoxy]-4-methylpentanoic acid potassium salt from step 3 (312 mg, 0.75 mmol) was coupled with aminoacetonitrile HCl Salt. The crude residue obtained was chromatographed on silica gel using 10% MeOH in dichloromethane to afford the title compound.
MS (+ESI) 416.2 [M+1]$^+$

EXAMPLE 26

Synthesis of N-(cyanomethyl)-4-methyl-2-[(4'-piperazin-1-yl-1,1'-biphenyl-4-yl)(pyridin-2-yl)methoxy]pentanamide Using the same protocol as described in example 21, 2-[(4-bromophenyl)(pyridin-2-yl)methoxy]-N-(cyanomethyl)-4-methylpentanamide from example 7, step 4 (241 mg, 0.58 mmol) was coupled with 4-piperazin-1-ylphenylboronic acid (155 mg, 0.64 mmol). The crude residue obtained was chromatographed on silica gel using 1% NH$_4$OH and 9% MeOH in dichloromethane to afford the title compound.
MS (+APCI) 498.3 [M+1]$^+$

EXAMPLE 27

Synthesis of 2-[(4-bromophenyl)(1,3-thiazol-2-yl)
methoxy]-N-(cyanomethyl)-4-methylpentanamide Step 1 (4-bromophenyl)(1,3-thiazol-2-yl)methanol Using the same protocol as described in example 22, step 1, 2-bromothiazole (451 μL, 5.0 mmol) was added to 4-bromobenzaldehyde (1.018 g, 5.5 mmol). The crude residue was chromatographed on silica gel using 50% ethyl acetate in hexanes to afford the title compound.

Step 2 methyl 2-[(4-bromophenyl)(1,3-thiazol-2-yl)
methoxy]-4-methylpentanoate

Using the same protocol as described in example 23, step 2, (4-bromophenyl)(1,3-thiazol-2-yl)methanol from step 1 (983 mg, 3.64 mmol) was added to methyl 2-bromo-4-methylpentanoate (624 μL, 3.82 mmol). The crude residue was chromatographed on silica gel using 25% ethyl acetate in hexanes to afford the title compound.

Step 3 2-[(4-bromophenyl)(1,3-thiazol-2-yl)methoxy]-4-methylpentanoic acid potassium salt Using the same protocol as described in example 17, step 5, methyl 2-[(4-bromophenyl)(1,3-thiazol-2-yl)methoxy]-4-methylpentanoate from step 2 (441 mg, 1.11 mmol) was hydrolysed with potassium hydroxide. The solid residue obtained was used as such in the next step.

Step 4 2-[(4-bromophenyl)(1,3-thiazol-2-yl)methoxy]-N-(cyanomethyl)-4-methylpentanamide Using the same protocol as described in example 17, step 3, 2-[(4-bromophenyl)(1,3-thiazol-2-yl)methoxy]-4-methylpentanoic acid potassium salt from step 3 (427 mg, 1.11 mmol) was coupled with aminoacetonitrile HCl Salt. The crude residue obtained was chromatographed on silica gel using 50% ethyl acetate in hexanes to afford the title compound.
MS (–APCI) 420.8 [M–1]$^-$

EXAMPLE 28

Synthesis of N-(cyanomethyl)-4-methyl-2-[(4'-piperazin-1-yl-1,1'-biphenyl-4-yl)(1,3-thiazol-2-yl)
methoxy]pentanamide Using the same protocol as described in example 21, 2-[(4-bromophenyl)(1,3-thiazol-2-yl)methoxy]-N-(cyanomethyl)-4-methylpentanamide from example 27, step 4 (225 mg, 0.53 mmol) was coupled with 4-piperazin-1-ylphenylboronic acid (141 mg, 0.58 mmol). The crude residue obtained was chromatographed on silica gel using 1% NH$_4$OH and 9% MeOH in dichloromethane to afford the title compound.
MS (+APCI) 504.2 [M+1]$^+$

EXAMPLE 29

Synthesis of (2S)-2-[(4-bromophenyl)(4-fluorophenyl)methoxy]-N-(cyanomethyl)-4-methylpentanamide Step 1 (4-bromophenyl)(4-fluorophenyl)methanol To a solution of 1,4-dibromobenzene (42.4 mmol, 10 g) in THF (100 mL) at –78° C. was added dropwise n-BuLi (42.4 mmol, 2 M in hexane). The mixture was stirred at –78° C. for 0.5 h., 4-fluorobenzaldehyde (42.4 mmol, 5.3 g) was added. The mixture was stirred at –78° C. for 1 h and then warmed to r.t. The reaction mixture was diluted with EtOAc, washed with NaHCO$_3$ and brine. The organic extract was dried (anhyd. MgSO4) and concentrated under reduced pressure to give an oil. Chromatography gave the title compound.

Step 2 (4-Bromophenyl)(4-fluorophenyl)methyl
2,2,2-trichloroethanimidoate

Sodium Hydride (60%, 0.356 mmol) was suspended in Et$_2$O (2 mL) and a solution of (4-bromophenyl)(4-fluorophenyl)methanol (3.56 mmol, 281 mg) in 2 mL Et$_2$O was added. The mixture was stirred at r.t. for 0.25 h. The mixture was cooled to 0° C., Trichloroacetonitrile (3.38 mmol, 144 mg) was added. The mixture was allowed to warmed to r.t. over 1 h. The reaction mixture was concentrated to an oil and pentane containing 0.36 mmol of MeOH was added with vigorous stirring. The mixture was filtered and washed with pentane. Concentration of the filtrate gave the crude imidate which was used as such without further purification.

Step 3 Methyl (2S)-2-[(4-bromophenyl)(4-fluorophenyl)methoxy]-4-methylpentanoate To a solution of the (4-bromophenyl)(4-fluorophenyl) methyl 2,2,2-trichloroethanimidoate of step 2 (1.18 mmol, 500 mg) in $CH_2Cl_2$ (5 mL) was added L-leucic acid methyl ester 2 (1.18 mmol, 146 mg) and then camphor sulfonic acid (0.12 mmol, 27 mg). The mixture was stirred at r.t. for 18 h. A few drops of saturated NaHCO3 was added, The mixture was diluted with ether and filtered. The filtrate was concentrated under reduced pressure and the crude product was chromatographed to give the title compound.

Step 4 (2S)-2-[(4-Bromophenyl)(4-fluorophenyl) methoxy]-4-methylpentanoic acid

To a suspension of methyl (2S)-2-[(4-bromophenyl)(4-fluorophenyl)methoxy]-4-methylpentanoate of step 3 (0.38 mmol, 157 mg) in MeOH/THF/$H_2O$ (1:2:2 mL) was added LiOH monohydrate (0.96 mmol, 40 mg). The mixture was stirred at r.t. for 2 h. HCl (1N) was added until pH 1. The mixture was extracted with $CH_2Cl_2$. The combined extracts were dried over anhydrous, MgSO4 and concentrated. The crude acid was used without further purification.

Step 5 (2S)-2-[(4-bromophenyl)(4-fluorophenyl) methoxy]-N-(cyanomethyl)-4-methylpentanamide To a solution of (2S)-2-[(4-bromophenyl)(4-fluorophenyl)methoxy]-4-methylpentanoic acid of step 4 (0.35 mmol, 151 mg) in DMF (3 mL) was added aminoacetonitrile hydrochloride (0.38 mmol) and HATU (0.38 mmol, 145 mg). Diisopropylethylamine (0.96 mmol, 123 mg) was added last, the mixture was stirred at r.t. for 3 days. Ether was added, followed by 1 N HCl. The mixture was separated after agitation. The organic extract was washed with 0.1 N HCl, water and brine and dried over anhyd. MgSO4. Concentration of the organic extracts followed by chromatography gave the title amide.

MS (–ESI): 433.2 [M–1]⁻

EXAMPLE 30

Synthesis of (2S)-2-[(4-bromophenyl)(cyclohexyl) methoxy]-N-(cyanomethyl)-4-methylpentanamide Step 1 (4-Bromophenyl)(cyclohexyl)methanol To a solution of 1,4-dibromobenzene (42.4 mmol, 10 g) in THF (100 mL) at –78° C. was added dropwise n-BuLi (42.4 mmol, 2 M in hexane). The mixture was stirred at –78° C. for 0.5 h., cyclohexanecarboxaldehyde (42.4 mmol, 4.8 g) was added. The mixture was stirred at –78° C. for 0.5 h and then warmed to r.t. The reaction mixture was diluted with EtOAc, washed with NaHCO3 and brine. The organic extract was dried (anhyd. $MgSO_4$) and concentrated under reduced pressure to give an oil. Chromatography gave the title compound.

Step 2 (4-Bromophenyl)(cyclohexyl)methyl 2,2,2-trichloroethanimidoate

Sodium Hydride (60%, 0.74 mmol) was suspended in $Et_2O$ (8 mL) and a solution of (4-bromophenyl)(cyclohexyl) methanol of step 1 (7.4 mmol, 2.0 g) in 8 mlL $Et_2O$ was added. The mixture was stirred at r.t. for 0.25 h. The mixture was cooled to 0° C., Trichloroacetonitrile (7.4 mmol, 1.07 g) was added. The mixture was allowed to warmed to r.t. over 1 h. The reaction mixture was diluted with EtOAc, washed with NaHCO3 and dried over anhyd. MgSO4. Concentration of the organic extract gave the crude imidate as a yellow solid which was used without further purification.

Step 3 (2S)-2-[(4-bromophenyl)(cyclohexyl)methoxy]-N-(cyanomethyl)-4-methylpentanamide To a solution of (4-bromophenyl)(cyclohexyl)methyl 2,2,2-trichloroethanimidoate of step 2 (4.18 mmol, 1.73 g) in $CH_2Cl_2$ (15 mL) was added (2S)-N-(cyanomethyl)-2-hydroxy-4-methylpentanamide from Step 1, Example 67 (4.18 mmol, 0.71 g) and then PPTS (0.42 mmol, 0.105 g). The mixture was stirred at r.t. for 72 h. A red solution resulted. The mixture was diluted with EtOAc and washed with NaHCO₃. The organic extract was dried (anhyd. MgSO4) and concentrated under reduced pressure to give an oil. Chromatography gave the less polar diastereomer and the more polar isomer.

MS (–ESI) 419.1 [M–1]⁻ for each isomer.

EXAMPLE 31

Synthesis of (2S)-2-{[1-(4-bromophenyl)-2-methylprop-2-enyl]oxy}-N-(cyanomethyl)-4-methylpentanamide Step 1 1-(4-bromophenyl)-2-methylprop-2-en-1-ol To a cold (–78° C.) solution of 1,4-dibromobenzene 1 (42.4 mmol, 10 g) in THF (60 mL) was added butyl lithium(42.4 mmol, 2.5 M in hexane). The mixture was stirred at –78° C. for 1 h. 2-methylpropenal (42.4 mmol, 2.97 g) was added. The mixture was stirred at –78° C. for 1 h. NH4Cl was added. The mixture was extracted with EtOAc. The organic extract was washed with brine, dried and concentrated to an oil. Chromatography (5-15% EtOAc/hexane) gave the desired alcohol.

Step 2 1-(4-Bromophenyl)-2-methylprop-2-enyl 2,2,2-trichloroethanimidoate

Sodium Hydride (60%, 1.1 mmol) was suspended in $Et_2O$ (14 mL) and a solution of alcohol 1 (11 mmol, 2.5 g) in $Et_2O$ (7 mL) was added. The mixture was stirred at r.t. for 0.25 h. The mixture was cooled to 0° C., Trichloroacetonitrile (11 mmol, 1.59 g) was added. The mixture was allowed to warmed to r.t. over 1 h. The reaction mixture was diluted with EtOAc, washed with NaHCO3 and dried over anhyd. MgSO4. Concentration of the extract gave the crude imidate which was chromatographed to give the title compound.

Step 3 (2S)-2-{[1-(4-bromophenyl)-2-methylprop-2-enyl]oxy}-N-(cyanomethyl)-4-methylpentanamide To a solution of 1-(4-bromophenyl)-2-methylprop-2-enyl 2,2,2-trichloroethanimidoate of step 2 (0.81 mmol, 300 mg) in $CH_2Cl_2$ (6 mL) was added (2S)-N-(cyanomethyl)-2-hydroxy-4-methylpentanamide from Step 1, Example 67 (0.81 mmol, 137 mg) and then PPTS (0.081 mmol, 20 mg). The mixture was stirred at r.t. for 72 h. The mixture was diluted with EtOAc and washed with NaHCO3. The organic extract was dried (anhyd. MgSO4) and concentrated under reduced pressure to give an oil. Chromatography (10% Acetone/EtOAc) gave 2 diastereomers (20 mg each).

MS (–ESI) 377.2 [M–1]⁻ for each diastereomer.

EXAMPLE 32

Synthesis of (2S)-2-[1-(4-bromophenyl)-2-methyl-propoxy]-N-(cyanomethyl)-4-methylpentanamide Step 1 1-(4-Bromophenyl)-2-methylpropan-1-ol To a solution of 4-brombenzaldehyde (27 mmol, 5.0 g) in THF (20 mL) was added at –78° C. a solution of isopropylmagnesium chloride (41 mmol, 20.2 mL, 2M in ether). The mixture was stirred at –78° C. for 1 h and warmed to 0° C. for 1 h. NH4Cl was added an the mixture was extracted with EtOAc. The organic extract was washed with brine, dried and concentrated to an oil. Chromatography (5-15% EtOAc/hexane) gave the desired alcohol.

Step 2 1-(4-Bromophenyl)-2-methylpropyl 2,2,2-trichloroethanimidoate

Sodium Hydride (60%, 0.87 mmol) was suspended in Et2O (9 mL) and a solution of 1-(4-bromophenyl)-2-methylpropan-1-ol of step 1 (8.7 mmol, 2.0 g) in Et2O (6 mL) was added. The mixture was stirred at r.t. for 0.25 h. The mixture was cooled to 0° C. Trichloroacetonitrile (11 mmol) was added. The mixture was allowed to warmed to r.t. over 1 h. The mixture was diluted with EtOAc and washed with NaHCO3. The organic extract was dried (anhyd. MgSO4) and concentrated under reduced pressure to give an oil. Chromatography (10% Acetone/EtOAc) gave the title compound.

Step 3 (2S)-2-[1-(4-bromophenyl)-2-methylpropoxy]-N-(cyanomethyl)-4-methylpentanamide To a solution of the 1-(4-bromophenyl)-2-methylpropyl 2,2,2-trichloroethanimidoate (2.6 mmol, 0.97 g) in $CH_2Cl_2$ (15 mL) was added (2S)-N-(cyanomethyl)-2-hydroxy-4-methylpentanamide from Step 1, Example 67 (3.9 mmol, 0.66 g) and then PPTS (0.26 mmol, 65 mg). The mixture was stirred at r.t. for 20 h. The mixture was diluted with EtOAc and washed with NaHCO3. The organic extract was dried (anhyd. MgSO4) and concentrated under reduced pressure to give an oil. Chromatography (10% Acetone/EtOAc) gave 2 diastereomers.

MS (–ESI) 379.1 [M–1]⁻ for each diastereomer.

EXAMPLE 33

Synthesis of (2S)-N-(Cyanomethyl)-4-methyl-2-{[(R)-[4'-(methylthio)-1,1'-biphenyl-4-yl](phenyl)methyl]oxy}pentanamide To a solution of (2S)-2-{[(R)-(4-bromophenyl)(phenyl)methyl]oxy}-N-(cyanomethyl)-4-methylpentanamide (0.84 mmol, 348 mg) in toluene (5 mL) and n-propanol (1.5 mL) was added under a stream of nitrogen 4-(methylthio)phenylboronic acid (1.0 mmol, 169 mg), $Pd(PPh_3)_4$ (0.042 mmol, 48 mg), $Na_2CO_3$ (2 M, 2 mL). The mixture was degassed with a rapid stream of nitrogen bubbling through the mixture and the mixture was heated to 100° C. for 2 h. The mixture was cooled, diluted with EtOAc and washed with water. The product was isolated by chromatography (40% EtOac/Hexane).

MS (–ESI) 457 [M–1]⁻

EXAMPLE 34

Synthesis of (2S)-N-(cyanomethyl)-4-methyl-2-{[(R)-[4'-(methylsulfonyl)-1,1'-biphenyl-4-yl](phenol)methyl]oxy}pentanamide To a solution of (2S)-N-(Cyanomethyl)-4-methyl-2-{[(R)-[4'-(methylthio)-1,1'-biphenyl-4-yl](phenyl)methyl]oxy}pentanamide from Example 33 (0.60 mmol, 274 mg) in $CH_2Cl_2$ was added m-CPBA (1.5 mmol, 268 mg, 80%) at 0° C. The mixture was stirred at 0° C. for 1 h. The mixture was warmed to r.t. and stirred for 3 h. The mixture was diluted with EtOAc and washed with $Na_2CO_3$, $NaHCO_3$, brine and dried (anhyd. $MgSO_4$). The organic extract was concentrated under reduced pressure and the residue was chromatographed to give the title compound.

MS (–ESI) 489 [M–1]⁻

EXAMPLE 35

Synthesis of (2S)-N-(Cyanomethyl)-4-methyl-2-{[(R)-(4'-morpholin-4-yl-1,1'-biphenyl-4-yl)(phenyl)methyl]oxy}pentanamide Step 1 4-(4-Bromophenyl)morpholine To a solution of of morpholine (0.85 mmol, 739 mg) in dioxane (12 mL) was added 1,4-dibromobenzene (21.2 mmol, 5 g), 2-(di-t-butylphosphine)biphenyl (1.02 mmol, 304 mg), potassium t-butoxide (25.5 mmol, 2.47 g) and $Pd_2(dba)_3$ (0.254 mmol, 233 mg) The mixture was degassed under a stream of nitrogen and then heated to reflux for 20 h. The mixture was diluted with EtOAc and washed with water and brine. The organic extract was concentrated under reduced pressure and the residue was chromatographed to give the desired product.

Step 2 (2S)-N-(Cyanomethyl)-4-methyl-2-{[(R)-(4'-morpholin-4-yl-1,1'-biphenyl-4-yl)(phenyl)methyl]oxy}pentanamide To a solution of N-(4-bromophenyl)morpholine (0.66 mmol, 159 mg) in DMF (7 mL) was added under a stream of nitrogen (2S)-N-(cyanomethyl)-4-methyl-2-{phenyl[4-(4,4,5,5-tetramethyl-1,3,2-dioxaborolan-2-yl)phenyl]methoxy}pentanamide from Example 16 (0.66 mmol, 250 mg). $PdCl_2(dppf)$ (0.033 mmol, 24 mg) and 2N $Na_2CO_3$ (2.63 mmol) was added. The mixture was degassed with a rapid stream of nitrogen bubbling through the mixture and the mixture was heated to 85° C. for 18 h. EtOAc was added, the mixture was washed with water and brine. The organic extract was dried and chromatographed (20-40% EtOAc/hexane) to give the title compound.

MS (–ESI) 496 [M–1]⁻

EXAMPLE 36

Synthesis of (2S)-N-(cyanomethyl)-4-methyl-2-{[(R)-[4-(5-methylcyclohex-1-en-1-yl)phenyl](phenyl)methyl]oxy}pentanamide

Step 1 methyl(2S)-2-{[(R)-(4-bromophenyl)(phenyl)methyl]oxy}-4-methylpentanoate To a solution of (2S)-2-{[(R)-(4-bromophenyl)methyl]oxy}-4-methylpentanoic acid from step 2 example 1, (2.5 g, 6.6 mmol) in methanol (25 mL) at 0° C. was added portionwise diazomethane in diethyl ether until the yellow color persisted. A few drops of acetic acid were then added to quench the excess diazomethane. The colorless solution was concentrated and then the volatiles were coevaporated twice with n-heptane. The oil was pumped on to remove the last traces of solvent.

$^1$H NMR (500 MHz, DMSO-d$_6$) δ 7.53 (d, 2H), 7.40-7.26 (m, 7H), 5.48 (s, 1H), 3.89-3.82 (m, 1H), 3.65 (s, 3H), 1.80-1.63 (m, 2H), 1.45-1.35 (m, 1H), 0.85 (d, 3H), 0.53 (d, 3H).

Step 2 methyl (2S)-4methyl-2-{[(R)-phenyl(4-pyridin-3-ylphenyl)methyl]oxy)}pentanoate To a mixture of methyl (2S)-2-{[(R)-(4-bromophenyl)(phenyl)methyl]oxy}-4-methylpentanoate from example 68 (1.88 g, 4.8 mmol) and pyridine-3-boronic acid-1,3-propanediol cyclic ester (862 mg, 5.29 mmol) in DMF (48 mL) was added 2 molar sodium carbonate (9.6 mL). The mixture was degased 3 times using nitrogen. Added [1,1'-bis(diphenylphosphino)ferrocene]dichloropalladium (II) complex with dichloromethane (1:1) (175 mg, 0.24 mmol). Degassed 3 more times with nitrogen. The mixture was inserted in an oil bath at 85° C. and stirred for 2.5 hr. The mixture was added to water (250 mL) and extracted with ethyl acetate (200 mL). Separated the layers and washed the organics with dilute brine (50 mL). Dried (Na$_2$SO$_4$), filtered, concentrated and chromatographed the residue on silica gel using 40% ethyl acetate in toluene as eluent to obtain the title compound as an oil.

MS (+APCI) 390.0 [M+1]$^+$

Step 3 3-{4-[(R)-{[(1S)-1-(methoxycarbonyl)-3-methylbutyl]oxy}(phenyl)methyl]phenyl}-1-methylpyridinium iodide A solution of methyl (2S)-4-methyl-2-{[(R)-phenyl(4-pyridin-3-ylphenyl)methyl]oxy}pentanoate from example 36 step 2 (881 mg, 2.26 mmol) and iodomethane (3.2 g, 22.6 mmol) in acetonitrile (22 mL) was heated in a pressure tube immersed in an oil bath at 120° C. for 18 hours. The solution was concentrated and the residue pumped on to obtain the pyridinium iodide salt as a foam.

$^1$H NMR (500 MHz, DMSO-d$_6$) δ 9.38 (s, 1H), 8.95 (d, 2H), 8.86 (d, 1H), 8.20 (t, 1H), 7.84 (d, 2H), 7.59 (d, 2H), 7.48-7.30 (m, 5H), 5.63 (s, 1H), 4.42 (s, 3H), 3.98-3.88 (m, 1H), 3.66 (s, 3H), 1.89-1.67 (m, 2H), 1.54-1.35 (m, 1H), 0.90 (d, 3H), 0.68 (d, 3H).

Step 4 methyl (2S)-4-methyl-2-{[(R)-[4-(1-methyl-1,2,5,6-tetrahydropyridin-3-yl)phenyl](phenyl)methyl]oxy}pentanoate To a solution of 3-{4-[(R)-{[(1S)-1-(methoxycarbonyl)-3-methylbutyl]oxy}(phenyl)methyl]phenyl}-1-methylpyridinium iodide from example 36 step 3 (1.45 g, 2.72 mmol) in methanol (25 mL) was added in portions sodium cyanoborohydride (4.25 g, 67.6 mmol). The mixture was heated at 65° C. for 1 h and then concentrated. The residue was partitioned between diethyl ether (75 mL) and water (25 mL). The separated aqueous layer was extracted again with diethyl ether (75 mL). The combined ether layers were dried (Na$_2$SO$_4$), filtered, concentrated and chromatographed on silica gel using 10% methanol in dichloromethane as eluent to obtain the title compound as an oil.

MS (+APCI) 408.2 [M+1]$^+$

Step 5 (2S)-N-(cyanomethyl)-4-methyl-2-{[(R)-[4-(5-methylcyclohex-1-en-1-yl)phenyl](phenyl)methyl]oxy}pentanamide A solution of methyl (2S)-4-methyl-2-{[(R)-[4-(1-methyl-1,2,5,6-tetrahydropyridin-3-yl)phenyl](phenyl)methyl]oxy}pentanoate from example 36 step 4 (100 mg, 0.25 mmol), THF (1.5 mL), methanol (0.5 mL) and 1N KOH (0.5 mL) was heated at 70° C. for 45 min. The mixture was concentrated and then 2 times with toluene to dry. To the residue was added DMF (1.5 mL), aminoacetonitrile hydrochloride (23 mg, 0.25 mmol), HATU coupling reagent (95 mg, 0.25 mmol) and triethylamine (75 mg, 0.75 mmol). The reagents were stirred at r.t. for 2 h, then added to dilute brine (5 mL) and extracted with 1:1 THF/ethyl acetate (25 mL). The organic layer was washed with brine (2×10 mL), dried (Na$_2$SO4), filtered, concentrated and the residue purified by chromatography on silica gel using 10% methanol in dichloromethane to obtain the title compound as a white solid.

MS (+APCI) 432.2 [M+1]$^+$

EXAMPLE 37

Synthesis of 3-{4-[(R)-[((1S)-1-{[(cyanomethyl)amino]carbonyl}-3-methylbutyl)oxy](phenyl)methyl]phenyl}-1-methylpyridinium iodide Using the same procedure as described for example 36 step 3 (2S)-N-(cyanomethyl)-4-methyl-2-{[(R)-phenyl(4-pyridin-3-ylphenyl)methyl]oxy}pentanamide (150 mg, 0.36 mmol) was converted to its pyridinium iodide salt. The salt was swished with diethyl ether (20 mL) for 18 h and the title compound was filtered off as an amorphous solid.

$^1$H NMR (500 MHz, DMSO-d$_6$) δ 9.35 (s, 1H), 8.95 (d, 1H), 8.85 (d, 1H), 8.69 (t, 1H), 8.19 (t, 1H), 7.84 (d, 2H), 7.63 (d, 2H), 7.47-7.29 (m, 5H), 5.55 (s, 1H), 4.40 (s, 3H), 4.14 (d, 2H), 3.87-3.79 (m, 1H), 1.84-1.63 (m, 2H), 1.47-1.38 (m, 1H), 0.87 (d, 3H), 0.73 (d, 3H).

EXAMPLE 38

Synthesis of (2S)-N-(cyanomethyl)-4-methyl-2-{[(R)-phenyl(4-pyridin-3-ylphenyl)methyl]oxy}pentanamide Using the same hydrolysis and coupling procedures as described in Step 5 of example 36, methyl (2S)-4-methyl-2-{[(R)-phenyl(4-pyridin-3-ylphenyl)methyl]oxy}pentanoate (250 mg, 0.64 mmol) was hydrolyzed and coupled to give the title compound as a white solid.

MS (+APCI) 414.1 [M+1]$^+$

EXAMPLE 39

Synthesis of (2S)-N-(cyanomethyl)-4-methyl-2-{[(R)-[4-(1-methylpiperidin-3-yl)phenyl](phenyl)methyl]oxy}pentanamide Step 1 methyl(2S)-4-methyl-2-{[(R)-[4-(1-methylpiperidin-3-yl)phenyl](phenyl)methyl]oxy}pentanoate To avoid catalytic poisoning during the hydrogenation, the quaternary pyridinium salt was first washed to remove free iodide. 3-{4-[(R)-{[(1S)-1-(methoxycarbonyl)-3-methylbutyl]oxy}(phenyl)methyl]phenyl}-1-methylpyridinium iodide from step 3 in example 36 (3.58 g, 6.6 mmol) was dissolved in dichloromethane (100 mL) and shaken with 5% sodium metabisulfite (30 mL) until the heavy red color dissipated. The organic layer was separated, dried (Na$_2$SO$_4$), filtered and concentrated to recover 3.2 g. of starting material. A mixture of the quaternary salt (3.2 g, 6.0 mmol), methanol (150 mL), acetic acid (800 mg, 12 mmol) and platinum oxide (hydrated) 79-84% (250 mg) was hydrogenated at 60 psi for 48 hours. The mixture was filtered, concentrated and then concentrated 2 times with n-heptane. The residue was chromatographed on silica gel using 5% methanol in dichloromethane to obtain the title compound as a foam.
MS (+APCI) 410.2 [M+1]$^+$ Step 1 Alternate Procedure A mixture of methyl (2S)-4-methyl-2-{[(R)-[4-(1-methyl-1,2,5,6-tetrahydropyridin-3-yl)phenyl](phenyl)methyl]oxy}pentanoate from step 4 in example 36 (300 mg, 0.73 mmol) ethanol (10 mL) acetic acid (87 mg, 1.46 mmol) and 10% palladium on charcoal (18 mg) was hydrogenated for 48 h at 60 psi. The mixture was filtered, concentrated and then concentrated 2 times with n-heptane. The residue was pumped on to obtain the title compound as an oil.
MS (+APCI) 410.2 [M+1]$^+$ Step 2 (2S)-N-(cyanomethyl)-4-methyl-2-{[(R)-[4-(1-methylpiperidin-3-yl)phenyl](phenyl)methyloxy)pentanamide Using the same hydrolysis and coupling procedures as described in step 5 in example 36 (337 mg, 0.82 mmol) of methyl (2S)-4-methyl-2-{[(R)-[4-(1-methylpiperidin-3-yl)phenyl](phenyl)methyl]oxy}pentanoate was hydrolyzed and coupled to give the title compound as a white solid.
MS (+APCI) 434.2 [M+1]$^+$

EXAMPLE 40

Synthesis of (2S)-N-(cyanomethyl)-4-methyl-2-{[(R)-[4-(1-oxidopyridin-3-yl)phenyl](phenyl)methyl]oxy}pentanamide To a solution of (2S)-N-(cyanomethyl)-4-methyl-2-{[(R)-phenyl(4-pyridin-3-ylphenyl)methyl]oxy}pentanamide from example 38 (95 mg, 0.23 mmol) in dichloromethane (10 mL) was added 77% quality 3-chloroperoxybenzoic acid (51.5 mg, 0.23 mmol) at 5° C. The temperature was permitted to gradually rise to r.t. over 1.5 h. The mixture was concentrated and the residue partitioned between ethyl acetate and 1M Na$_2$CO$_3$. The ethyl acetate layer was dried (Na$_2$SO$_4$) and concentrated to yield 100 mg of the title compound. Purification by chromatography on silica gel using 10% methanol in dichloromethane and concentrating with diethyl ether 2 times gave a white solid.
MS (+APCI) 430.1 [M+1]$^+$

EXAMPLE 41

Synthesis of (2S)-N-(cyanomethyl)-2-{[(R)-{4-[1-(2-methoxyethyl)piperidin-3-yl]phenyl}(phenyl)methyl]oxy}-4-methylpentanamide Step 1 3-{4-[(R)-{[(1S)-1-(methoxycarbonyl)-3-methylbutyl]oxy}(phenyl)methyl]phenyl}-1-(2-methoxyethyl) pyridinium bromide A solution of methyl (2S)-4-methyl-2-{[(R)-phenyl(4-pyridin-3-ylphenyl)methyl]oxy}pentanoate from example 36 step 2 (740 mg, 1.9 mmol) and 2-bromoethyl methyl ether (1.32 g, 9.5 mmol) in acetonitrile (10 mL) was heated in a pressure tube emersed in an oil bath at 120+ C. for 18 hours. The mixture was concentrated and the residue slurried with diethyl ether (25 mL) 2 times followed by decanting and then pumped on by high vacuum to obtain the title compound as a foam.
$^1$H NMR (500 MHz, DMSO-d$_6$) δ 9.44 (s, 1H), 9.0 (d, 1H), 8.93 (d, 1H), 8.24 (t, 1H), 7.87 (d, 2H), 7.60 (d, 2H), 7.46-7.30 (m, 5H), 5.62 (s, 1H), 4.88 (t, 2H), 3.96-3.85 (m, 3H), 3.65 (s, 3H), 3.28 (s, 3H), 1.88-1.68 (m, 2H), 1.50-1.41 (m, 1H), 0.88 (d, 3H), 0.57 (d, 3H).

Step 2 methyl (2S)-2-{[(R)-(4-[1-(2-methoxyethyl)piperidin-3-yl]phenyl}(phenyl)methyl]oxy}-4-methylpentanoate A mixture of 3-{4-[(R)-{[(1S)-1-(methoxycarbonyl)-3-methylbutyl]oxy}(phenyl)methyl]phenyl}-1-(2-methoxyethyl)pyridinium bromide from example 41 step 1 (870 mg, 1.64 mmol), ethanol (50 mL), acetic acid (197 mg, 3.28 mmol) and platinum oxide (hydrated) 79-84% (63 mg) was hydrogenated at 60 psi for 18 hours. The mixture was filtered, concentrated and then concentrated twice with n-heptane. The residue was chromatographed on silica gel using 10% methanol in dichloromethane to obtain the title compound as a thick oil.
MS (+APCI) 454.2 [M+1]$^+$ Step 3 (2S)-N-(cyanomethyl)-2-{[(R)-{4-[1-(2-methoxyethyl)piperidin-3-yl]phenyl}(phenyl)methyl]oxy}-4-methylpentanamide Using the same hydrolysis and coupling procedures as described for example 36 step 5, methyl (2S)-2-{[(R)-{4-[1-(2-methoxyethyl)piperidin-3-yl]phenyl}(phenyl)methyl]oxy}-4-methylpentanoate (741 mg, 1.6 mmol) was hydrolyzed and coupled to give the title compound as a white solid.
MS (+APCI) 478.2 [M+1]$^+$

EXAMPLE 42

Synthesis of (2S)-N-(cyanomethyl)-2-{[(R)-{4-[1-(2-methoxyethyl)-1-oxidopiperidin-3-yl]phenyl}(phenyl)methyl]oxy}-4-methylpentanamide To a solution of (2S)-N-(cyanomethyl)-2-{[(R)-{4-[1-(2-methoxyethyl)piperidin-3-yl]phenyl}(phenyl)methyl]oxy}-4-pentanamide from example 41 step 3 (390 mg, 0.81 mmol) in dichloromethane (12 mL) at 0° C. was added 77% quality 3-chloroperoxybenzoic acid (183 mg, 0.81 mmol). The mixture was stirred for 5 minutes and then 5% NaHCO$_3$ solution (10 mL) was added with stirring. The dichloromethane layer was separated, dried (Na$_2$SO$_4$), filtered and concentrated. The residue was chromatographed on silica gel using 30% methanol in ethyl acetate as eluent to obtain the title compound as a foam.

MS (+APCI) 494.3 [M+1]$^+$

EXAMPLE 43

Synthesis of (2S)-N-(cyanomethyl)-4-methyl-2-{[(R)-phenyl(4-quinolin-3-ylphenl)methyl]oxy}pentanamide Step 1 methyl (2S)-4-methyl-2-{[(R)-phenyl(4-quinolin-3-ylphenyl)methyl]oxy}pentanoate Using the same procedure as described for example 36 step 2, methyl (2S)-2-{[(R)-(4-bromophenyl)(phenyl)methyl]oxy}-4-methylpentanoate (2.05 g, 5.25 mmol) and 3-quinolineboronic acid (1.0 g, 5.78 mmol) were coupled to give the title compound as an oil.

MS (+APCI) 440.1 [M+1]$^+$

Step 2 (2S)-N-(cyanomethyl)-4-methyl-2-{[(R)-phenyl(4-quinolin-3-ylphenyl)methy]oxy}pentanamide Using the same hydrolysis and coupling procedures as described for the preparation of for example 36 step 5, methyl (2S)-4-methyl-2-{[(R)-phenyl(4-quinolin-3-ylphenyl)methyl]oxy}pentanoate (500 mg, 1.1 mmol) was hydrolyzed and coupled to give the title compound as a white solid.

MS (+APCI) 464.1 [M+1]$^+$

EXAMPLE 44

Synthesis of (2S)-N-(cyanomethyl)-4-methyl-2-{[(R)-[4-(1-methyl-1,2,3,4-tetrahydroquinolin-3-yl)phenyl](phenyl)methyl]oxy}pentanamide Step 1 3-(4-[(R)-{[(1S)-1-(methoxycarbonyl)-3-methylbutyl]oxy}(phenyl)methyl]phenyl}-1-methylguinolinium iodide Using the same procedure as described for example 36 step 3, methyl (2S)-4-methyl-2-{[(R)-phenyl(4-quinolin-3-ylphenyl)methyl]oxy}pentanoate (750 mg, 1.7 mmol) was converted to the title compound as a solid.

$^1$H NMR (500 MHz, DMSO-d$_6$) δ 9.95 (s, 1H), 9.59 (s, 1H), 8.53 (d, 1H), 8.48 (d, 1H), 8.28 (t, 1H), 8.09 (t, 1H), 7.98 (d, 2H), 7.65 (d, 2H), 7.47-7.30 (m, 5H), 5.65 (s, 1H), 4.72 (s, 2H), 3.48-3.40 (m, 1H), 3.67 (s, 3H), 1.86-1.68 (m, 2H), 1.50-1.43 (m, 1H), 0.89 (d, 3H), 0.68 (d, 3H).

Step 2 methyl (2S)-4-methyl-2-{[(R)-[4-(1-methyl-1,2,3,4-tetrahydroquinolin-3-yl)phenyl](phenyl)methyl]oxy }pentanoate Using the same procedure as described for example 39 Step 1, 3-{4-[(R)-{[(1S)-1-(methoxycarbonyl)-3-methylbutyl]oxy}(phenyl)methyl]phenyl}-1-methylquinolinium iodide (1.0 g, 1.7 mmol) was hydrogenated and purified by chromatography on silica gel using 5% ethyl acetate in hexanes to yield the title compound as a foam.

MS (+APCI) 458.2 [M+1]$^+$

Step 3 (2S)-N-(cyanomethyl)-4-methyl-2-{[(R)-[4-(1-methyl-1,2,3,4-tetrahydroquinolin-3-yl)phenyl](phenyl)methyl]oxy}pentanamide Using the same hydrolysis and coupling procedures as described for example 36 Step 5, methyl (2S)-4-methyl-2-{[(R)-[4-(1-methyl-1,2,3,4-tetrahydroquinolin-3-yl)phenyl](phenyl)methyl]oxy}pentanoate (273 mg, 0.59 mmol) was hydrolyzed and coupled to give the title compound as a white solid.

MS (+APCI) 482.2 [M+1]$^+$

EXAMPLE 45

Synthesis of (2S)-N-(cyanomethyl)-4-methyl-2-{[(R)-[4-(1-oxidoquinolin-3-yl)phenyl](phenyl)methyl]oxy}pentanamide Using the same procedure as described for example 40, (2S)-N-(cyanomethyl)-4-methyl-2-{[(R)-phenyl(4-quinolin-3-ylphenyl)methyl]oxy}pentanamide (126 mg, 0.27 mmol) was oxidized to give the title compound.

MS (+APCI) 480.1 [M+1]$^+$

EXAMPLE 46

Synthesis of 4-[[((1S)-1-{[(cyanomethyl)amino]carbonyl}-3-methylbutyl)oxy](phenyl)methyl]benzoic acid (2S)-2-[(4-bromophenyl)(phenyl)methoxyl]-N-(cyanomethyl)-4-methylpentanamide from example 67 step 4 (1.7 g, 4 mmol), tri-n-butylamine (2.7 g, 14.7 mmol, 3.7 eq), triphenylphosphine (160 mg, 0.6 mmol, 0.15 eq) bis (triphenylphosphine)palladium (11) chloride (42.5 mg, 0.06 mmol, 0.015 eq) and H$_2$O (800 mg, 0.8 mmol, 0.2 eq) were charged in a pressure steel bomb. The apparatus was heated at 130° C. under 300 psi of carbon monoxide for 18 hours. Crude reaction mixture was partitioned between ethyl acetate (50 mL) and 1N HCl (25 mL). Organic fraction was washed with brine, dried, concentrated to give a light pink oil. Chromatographed with 30% EtOAc/hexane+1% AcOH to yield a yellow oil.

MS (−ESI) 379.2 [M−1]$^−$

EXAMPLE 47

Synthesis of 4-[[((1S)-1-{[(cyanomethyl)amino]carbonyl}-3-methylbutyl)oxy](phenyl)methyl]-N-methoxy-N-methylbenzamide To a solution of 4-[[((1S)-1-{[(cyanomethyl)amino]carbonyl}-3-methylbutyl)oxy](phenyl)methyl]benzoic acid from example 46 (40 mg, 0.105 mmol) and N,O-dimethylhydroxylamine hydrochloride (10.3 mg, 0.105 mmol, 1 eq) in 1 mL DMF were added HATU (40 mg, 0.105 mmol, 1 eq), triethylamine (32 mg, 0.315 mmol, 3 eq). The mixture was stirred at room temperature for 18 hours, then poured into a half saturated solution of NaHCO3 (5 mL). It was extracted with EtOAc (2×10 mL); washed organic fraction with brine, concentrated to give the product.

MS (+APCI) 424.2 [M+1]$^+$

EXAMPLE 48

Synthesis of 4-[[((1S)-1-{[(cyanomethyl)amino] carbonyl}-3-methylbutyl)oxy](phenyl)methyl]-N,N-dimethylbenzamide Using the same coupling procedure as described for example 47, 4-[[((1S)-1-{[(cyanomethyl)amino]carbonyl}-3-methylbutyl)oxy](phenyl)methyl]benzoic acid (51 mg, 0.134 mmol) was reacted with dimethylamine hydrochloride (11 mg, 0.134 mmol, 1 eg) to give the title compound as an oil after chromatography with 25% acetone/toluene.

MS (+APCI) 408.2 [M+1]$^+$

EXAMPLE 49

Synthesis of (2S)-N-(cyanomethyl)-4-methyl-2-[[4-(morpholin-4-ylcarbonyl)phenyl](phenyl)methoxy]pentanamide Using the same coupling procedure as described for example 47, 4-[[((1S)-1-{[(cyanomethyl)amino]carbonyl)}-3-methylbutyl)oxy](phenyl)methyl] benzoic acid (39 mg, 0.102 mmol) was reacted with morpholine (8.9 mg, 0.102 mmol) 1 eg) to give the title compound as an oil after chromatography with 50% EtOAc/toluene+2% Et$_3$N.

MS (-ESI) 448.2 [M-1]$^-$

EXAMPLE 50

Synthesis of (2S)-N-(cyanomethyl)-4-methyl-2-{[(R)-{4-[4-(methylthio)benzoyl]phenyl}(phenyl)methyl]oxy}pentanamide (2S)-2-{[(R)-(4-bromophenyl)(phenyl)methyl]oxy}-N-(cyanomethyl)-4-methylpentanamide from example 68 (150 mg, 0.361 mmol), 4-(methylthio)phenyl boronic acid (67 mg, 0.398 mmol, 1.1 eg), [1,1-bis(diphenylphosphino)ferrocene]dichloropalladium (II)complex) (7.9 mg, 0.011 mmol, 0.03 eg), potassium iodide (180 mg, 1.08 mmol, 3 eg), potassium carbonate (149 mg, 1.08 mmol, 3 eg) were mixed together in anisole (5 mL). The reaction mixture was degased 3× with nitrogen, then heated at 90° C. under 1atm of CO for 18 hours. The crude reaction mixture was concentrated under high vacuum and the residue was chromatographed with 30% EtOAc/hexane to give the title compound.

MS (+ESI) 487.1 [M+1]$^+$

EXAMPLE 51

Synthesis of (2S)-N-(cyanomethyl)-4-methyl-2-{[(R)-{4-[4-(methylsulfonyl)benzoyl]phenyl}(phenyl)methyl]oxy}pentanamide To a solution of (2S)-N-(cyanomethyl)-4-methyl-2-{[(R)-{4-[4-(methylthio)benzoyl]phenyl}(phenyl)methyl]oxy}pentanamide from example 50, (30 mg, 0.062 mmol) in dichloromethane (5 mL) was added m-chloroperoxybenzoic acid (29 mg, 77% purity, 0.130 mmol, 2.1 eg) and it was stirred at room temperature for 1 hour. Reaction mixture was then washed with 5% NaHCO3, dried, concentrated to dryness, chromatographed with 50% EtOAc/hexane+2% dichloromethane to yield the title compound.

MS (-ESI) 517.1 [M-1]$^-$

EXAMPLE 52

Synthesis of (2S)-2-{[(R)-[4-(1,1'-biphenyl-4-ylcarbonyl)phenyl](phenyl)methyl]oxy}-N-(cyanomethyl)-4-methylpentanamide Using the same procedures as described for the example 50, (2S)-2-{[(R)-(4-bromophenyl)(phenyl)methyl]oxy}-N-(cyanomethyl)-4-methylpentanamide (105 mg, 0.253 mmol) was reacted with 1,1'-biphenyl-4-ylboronic acid (50 mg, 0.253 mmol, 1 eg) to give the title compound after chromatography with 20% EtOAc/hexane.

MS (-APCI) 515.5[M-1]$^-$

EXAMPLE 53

Synthesis of (2S)-2-[(5-bromopyridin-2-yl)(phenyl)methoxy]-N-(cyanomethyl)-4-methylpentanamide

Step 1 Synthesis of (5-bromopyridin-2-yl)(phenyl)methanol 2,5 dibromopyridine (15.0 g, 63.3 mmol) was added to toluene (450 ml) and it was cooled at -70° C. BuLi (1.6 M in hexanes)(41 ml, 66.5 mmol, 1.05 eg) was added dropwise over 1 hour, then reaction mixture was stirred at -70° C. for another hour. Benzaldehyde (7.4 g, 69.6 mmol, 1.1 eg) dissolved in toluene (5 mL) was added slowly. The mixture was stirred at -70° C. for 30 min., then warmed to 0° C. Quenched with Sat NH4Cl (200 mL) and phases partitioned. Aqueous phase was extracted with EtOAc (100 mL) and combined organic washed with brine, dried, evaporated. Residue was chromatographed with 15% EtOAc/hexane to yield the title compound.

Step 2 Synthesis of (5-bromopyridin-2-yl)(phenyl)methyl 2,2,2-trichloro ethanimidoate To a solution of (5-bromopyridin-2-yl)(phenyl)methanol from example 53 step 1 (2 g, 7.6 mmol) in Et2O (20 mL) was added NaH (30 mg; 60% dispersion in oil, 0.76 mmol, 0.1 eg). The resulting suspension was cooled to 0° C. and trichloroacetonitrile (1.1 g, 7.6 mmol, 1 eg) was added dropwise. Reaction mixture was stirred at 0° C. for 15 min., then at room temperature for 30 min. The precipitate was filtered and washed with Et$_2$O.

Step 3 Synthesis of (2S)-2-[(5-bromopyridin-2-yl)(phenyl)methoxy]-N-(cyanomethyl)-4-methylpentanamide To a solution of (5-bromopyridin-2-yl)(phenyl)methyl 2,2,2-trichloroethanimidoate from example 53 step 2 (2 g, 4.9 mmol) in 1,2-dichloroethane (50 mL) was added (2S)-N-(cyanomethyl)-2-hydroxy-4-methylpentanamide (830 mg, 4.9 mmol, 1 eg) and camphor sulfonic acid (114 mg, 0.49 mmol, 0.10 eg). The suspension was heated to reflux for 18 hours, then concentrated to dryness. Residue was chromatographed with 25% EtOAc/hexane to yield the title compound.

MS (-ESI) 414, 416 [M-1]$^-$

EXAMPLE 54

Synthesis of (2S)-N-(cyanomethyl)-4-methyl-2-{phenyl[5-(4-piperazin-1-ylphenyl)pyridin-2-yl]methoxy}pentanamide (2S)-2-[(5-bromopyridin-2-yl)(phenyl)methoxy]-N-(cyanomethyl)-4-methylpentanamide from example 53 step 3 (156 mg, 0.375 mmol), 4-piperazine-1-ylphenyl boronic acid (100 mg, 0.413 mmol, 1.1 eg), [1,1'-Bis(diphenylphosphino)-ferrocene dichloropalladium II complex with $CH_2Cl_2$ (13.7 mg, 0.0187 mmol, 0.05 eg), sodium carbonate (2M soln, 750 uL, 1.5 mmol, 4 eg) were mixed together in DMF (5 mL). The reaction mixture was degased 3× with $N_2$, then heated to 90° C. for 5 hours. After cooling, the mixture was evaporated under high vacuum and residue was chromatographed with a mixture of dichloromethane/methanol/ammonium hydroxide (90:9:1) to give the title compound.

MS (−ESI) 496.2 [M−1]⁻

EXAMPLE 55

Synthesis of (2S)-N-(cyanomethyl-4-methyl-2-[{5-[4-(methylthio)phenyl]pyridin-2-yl}(phenyl)methoxy]pentanamide Using the same procedure as described for example 54, (2S)-2-[(5-bromopyridin-2-yl)(phenyl)methoxy]-N-(cyanomethyl)-4-methylpentanamide (190 mg, 0.456 mmol) was reacted with 4-(methylthio)phenyl boronic acid (84 mg, 0.502 mmol, 1.1 eg) to give respectively the less polar isomer and the more polar isome after chromatography with 30% EtOAc/hexane.

MS(−ESI) 458.2 [M−1]⁻

EXAMPLE 56

Synthesis of (2S)-N-(cyanomethyl)-4-methyl-2-{[(R or S)-{5-[4-(methylsulfonyl)phenyl]pyridin-2-yl}(phenyl)methyl]oxy}pentanamide To a solution of (2S)-N-(cyanomethyl)-4-methyl-2-[{5-[4-(methylthio)phenyl]pyridin-2-yl}(phenyl)methoxy]pentanamide from example 55 (112 mg, 0.244 mmol) in dichloromethane (20 mL) at 0° C. was added portionwise m-chloro-peroxybenzoic acid (109 mg, 77% purity, 0.488 mmol, 2 eq). The reaction mixture was then allowed to stir at room temperature for 30 min. After washing the mixture with 5% NaHCO3 and evaporation, the residue was chromatographed with 60% EtOAc/hexane+1% dichloromethane to give the title compound.

MS (+ESI) 492.1 [M+1]⁺

EXAMPLE 57

Synthesis of (2S)-N-(cyanomethyl)-4-methyl-2-{[(R or S)-{5-[4-methylsulfonyl)phenyl]pyridin-2-yl}(phenyl)methyl]oxy}pentanamide Using the same procedure as described for example 56, (2S)-N-(cyanomethyl-4-methyl-2-[{5-[4-(methylthio)phenyl]pyridin-2-yl}(phenyl)methoxy]pentanamide from example 55 (30 mg, 0.065 mmol) was reacted with m-chloroperoxybenzoic acid (29 mg, 77% purity, 0.13 mmol, 2 eg) to give the title compound.

MS (+ESI) 492 [M+1]⁺

EXAMPLE 58

Synthesis of (2S)-N-(cyanomethyl)-4-methyl-2-[{5-[4-(methylsulfonyl)phenyl]-1-oxidopyridin-2-yl}(phenyl)methoxy]pentanamide The title compound was obtained from over oxidation of (2S)-N-(cyanomethyl-4-methyl-2-[{5-[4-(methylthio)phenyl]pyridin-2-yl}(phenyl)methoxy]pentanamide from example 55 during the preparation of example 57. The title compound was recovered by chromatography with EtOAc.

MS (+ESI) 508 [M+1]⁺

EXAMPLE 59

Synthesis of (2S)-2-[(4-bromothien-2-yl)(phenyl)methoxy]-N-(cyanomethyl)-4-methyl pentanamide

Step 1 Synthesis of (4-bromothien-2-yl)(phenyl)methanol 2,4 dibromothiophene (3 g, 12.4 mmol) was dissolved in $Et_2O$ (50 mL) and cooled to −78° C. BuLi (1.6 M in hexanes)(8.1 mL, 13 mmol, 1.05 eg) was added dropwise over 20 min. then the yellow solution was stirred at −78° C. for 1 hour. Benzaldehyde (1.45 g, 13.64 mmol, 1.1 eg) dissolved in Et2O (15 mL) was added dropwise at a rate to maintain internal temperature <−70° C., then reaction mixture was allowed to warm slowly to 0° C. Quenched with Sat $NH_4Cl$ (50 mL) and phases partitioned. Organic fraction was washed with brine, dried, concentrated. Residue was chromatographed with 10% EtOAc/hexane to yield the title compound as a pale yellow solid.

Step 2 Synthesis of (4-bromothien-2-yl)(phenyl)methyl 2,2,2-trichloroethanimidoate Using the same procedure as described for example 53, Step 2 (4-bromothien-2-yl)(phenyl)methanol (1 g, 3.7 mmol) provided the title compound as an orange oil after chromatography with 5% EtOAc/hexane.

Step 3 Synthesis of (2S)-2-[(4-bromothien-2-yl)(phenyl)methoxy]-N-(cyanomethyl)-4-methylpentanamide Using the same procedure as described for example 53, Step 3, (4-bromothien-2-yl)(phenyl)methyl 2,2,2-trichloroethanimidoate (970 mg, 2.35 mmol) provided the title compound after chromatography with 25% EtOAc/hexane.

MS (−ESI) 419, 421 [M−1]⁻

EXAMPLE 60

Synthesis of (2S)-2-[(5-bromo-1-oxidopyridin-2-yl)(phenyl)methoxy]-N-(cyanomethyl)-4-methylpentanamide Using the same procedure as described for example 40, (2S)-2-[(5-bromopyridin-2-yl)(phenyl)methoxy]-N-(cyanomethyl)-4-methylpentanamide (51 mg, 0.123 mmol) was oxidized to give the title compound after chromatography with 50% EtOAc/hexane.

MS (−ESI) 430, 432 [M−1]⁻

EXAMPLE 61

Synthesis of (2S)-N-(cyanomethyl)-4methyl-2-{[(R)-[4-(1-methylpiperidin-4-yl)phenyl](phenyl)methyl]oxy}pentanamide

Step 1 methyl (2S)-4-methyl-2-{[(R)-phenyl(4-pyridin-4-ylphenyl)methyl]oxy}pentanoate Using the same procedure as described example 36 Step 2, methyl (2S)-2-{[(R)-(4-bromophenyl)(phenyl)methyl]oxy}-4-methyl pentanoate (2.7 g, 6.8 mmol) was coupled with pyridine-4-boronic acid (920 mg, 7.5 mmol, 1.1 eg) to yield the title compound after chromatography with 30% EtOAc/hexane.

Step 2 4-{4-[(R)-{[(1S)-1-(methoxycarbonyl)-3-methylbutyl]oxy}(phenyl)methyl]phenyl}-1-methylpyridinium iodide Using the same procedure as described for example 36 Step 3, methyl (2S)-4-methyl-2-{[(R)-phenyl(4-pyridin-4-ylphenyl)methyl]oxy}pentanoate (757 mg, 1.95 mmol) provided the title compound.

Step 3 methyl (2S)-4-methyl-2-{[(R)-[4-(1-methylpiperidin-4-yl)phenyl](phenyl)methyl]oxy}pentanoate Using the same procedure as described example 39 Step 1, 4-{4-[(R)-{[(1S)-1-(methoxycarbonyl)-3-methylbutyl]oxy}(phenyl)methyl]phenyl}-1-methylpyridinium iodide (460 mg, 0.866 mmol) gave the title compound.

Step 4 (2S)-N-(cyanomethyl)-4-methyl-2-{[(R)-[4-(1-methylpiperidin-4-yl)phenyl](phenyl)methyl]oxy}pentanamide Using the same procedure as described for example 36 Step 5, 4-{4-[(R)-{[(1S)-1-(methoxycarbonyl)-3-methylbutyl]oxy}(phenyl)methyl]phenyl}-1-methylpyridinium iodide (354 mg, 0.88 mmol) gave the title compound as a light beige solid after stirring in 20% EtOAc/hexane for 2 hours.
MS (−APCI) 432.2 [M−1]⁻

EXAMPLE 62

Synthesis of (2S)-N-(cyanomethyl)-2-{[(R)-{4-[1-(2-methoxyethyl)piperidin-4-yl]phenyl}(phenyl)methyl]oxy}-4-methylpentanamide

Step 1 4-{4-[(R)-{[(1S)-1-(methoxycarbonyl)-3-methylbutyl]oxy}(phenyl)methyl]phenyl}-1-(2-methoxyethyl)pyridinium bromide Using the same procedure as described for example 41, Step 1, methyl (2S)-4-methyl-2-{[(R)-phenyl(4-pyridin-4-ylphenyl)methyl]oxy}pentanoate (580 mg, 1.5 mmol) provided the title compound.

Step 2 (2S)-2-{[(R)-{4-[1-(2-methoxyethyl)piperidin-4-yl]phenyl}(phenyl)methyl]oxy}-4-methylpentanoate Using the same procedure as described for example 41, Step 2, 4-{4-[(R)-{[(1S)-1-(methoxycarbonyl)-3-methylbutyl]oxy}(phenyl)methyl]phenyl}-1-(2-methoxyethyl)pyridinium bromide (792 mg, 1.5 mmol) provided the title compound after chromatography with 5% methanol/chloroform.

Step 3 (2S)-N-(cyanomethyl)-2-{[(R)-{4-[1-(2-methoxyethyl)piperidin-4-yl]phenyl}(phenyl)methyl]oxy}-4-methylpentanamide Using the same procedure as described for example 36, Step 5, (2S)-2-{[(R)-{4-[1-(2-methoxyethyl)piperidin-4-yl]phenyl}(phenyl)oxy}-4-methylpentanoate (417 mg, 0.92 mmol) was hydrolyzed and coupled to give the title compound after chromatography with dichloromethane/methanol/ammonium hydroxide (90:9:1).
MS (−APCI) 476.4 [M−1]⁻

EXAMPLE 63

Synthesis of (2S)-N-(cyanomethyl)-4-methyl-2-{[(R)-[4-(6-methyl-1-oxidopyridin-3-yl)phenyl](phenyl)methyl]oxy}pentanamide

Step 1 methyl (2S)-4-methyl-2-{[(R)-[4-(6-methylpyridin-3-yl)phenyl](phenyl)methyl]oxy}pentanoate Using the same procedure described for example 36, Step 2, methyl-(2S)-{[(R)-(4-bromophenyl)(phenyl)methyl]oxy}-4-methylpentanoate (1.6 g, 4.1 mmol) was coupled with dimethyl 6-methylpyridin-3-yl boronate (1 g, 6.0 mmol, 1.5 eg) to yield the title compound as a yellow oil after chromatography with 30% EtOAc/hexane.

Step 2 Synthesis of (2S)-N-(cyanomethyl)-4-methyl-2-{[(R)-[4-(6-methylpyridin-3-yl)phenyl](phenyl)methyl]oxy}pentanamide Using the same procedure as described for example 36, Step 5, methyl (2S)-4-methyl-2-{[(R)-[4-(6-methylpyridin-3-yl)phenyl](phenyl)methyl]oxy}pentanoate (202 mg, 0.5 mmol) was hydrolyzed and coupled to give the title compound as a white solid after chromatography with 50% EtOAc/hexane.

Step 3 (2S)-N-(cyanomethyl)-4-methyl-2-{[(R)-[4-(6-methyl-1-oxidopyridin-3-yl)phenyl](phenol)methyl]oxy}pentanamide Using the same procedures as described for example 40, (2S)-N-(cyanomethyl)-4-methyl-2-{[(R)-[4-(6-methylpyridin-3-yl)phenyl](phenyl)methyl]oxy}pentanamide (100 mg, 0.23 mmol) was oxidized to give the title compound as a white solid.
MS (+APCI) 444.1 [M+1]⁺

EXAMPLE 64

Synthesis of (2S)-N-(cyanomethyl)-4-methyl-2-{[(R)-[4-(1-oxidopyridin-4-yl)phenyl](phenyl)methyl]oxy}pentanamide

Step 1 (2S)-N-(cyanomethyl)-4-methyl-2-{[(R)-phenyl(4-pyridin-4-ylphenyl)methyl]oxy}pentanamide Using the same procedure as described for example 36 Step 5, methyl (2S)-4-methyl-2-{[(R)-phenyl(4-pyridin-4- ylphenyl) methyl]oxy}pentanoate (525 mg, 1.35 mmol) was hydrolyzed and coupled to give the title compound after chromatography with 50% EtOAc/hexane.

Step 2 (2S)-N-(cyanomethyl)-4-methyl-2-{[(R)-[4-(1-oxidopyridin-4-yl)phenyl)](phenyl)methyl]oxy}pentanamide Using the same procedure as described for example 40 (2S)-N-(cyanomethyl)-4-methyl-2-{[(R)-phenyl(4-pyridin-4-ylphenyl)methyl]oxy}pentanamide (117 mg, 0.28 mmol) was oxidized to give the title compound as a light yellow solid.

MS (+APCI) 430.1 [M+1]$^+$

EXAMPLE 65

Synthesis of (2S)-N-(cyanomethyl)-4-methyl-2-{[(R)-[4-(1-methyl-1-oxidopiperidin-4-yl)phenyl](phenyl)methyl]oxy}pentanamide Using the same procedure as described for example 40, (2S)-N-(cyanomethyl)-4-methyl-2-{[(R)-[4-(1-methylpiperidin)-4-yl)phenyl](phenyl)methyl]oxy}pentanamide (80 mg, 0.185 mmol) was oxidized to give the title compound as a foamy solid.

MS (+APCI) 450.2 [M+1]$^+$

EXAMPLE 66

Synthesis of (2S)-N-(cyanomethyl)-2-{[(R)-{4-[1-(2-methoxyethyl)-1-oxidopiperidin-4-yl]phenyl}(phenyl)methyl]oxy}-4-methylpentanamide Using the same procedure as described for example 40, (2S)-N-(cyanomethyl)-2-{[(R)-{4-[1-(2-methoxyethyl)piperidin-4-yl]phenyl}(phenyl)methyl]oxy}-4-methylpentanamide (75 mg, 0.157 mmol) was oxidized to give the title compound after chromatography with 50% methanol/acetone.

MS (+ESI) 494.3 [M+1]$^+$

EXAMPLE 67

Synthesis of (2S)-2-[(4-bromophenyl)(phenyl)methoxy]-N-(cyanomethyl)-4-methylpentanamide Step 1
(2S)-N-(cyanomethyl)-2-hydroxy-4-methylpentanamide L-leucic acid (85 g, 0.643 mole), amino acetonitrile hydrochloride (68 g, 0.734 mole, 1.14 eg), pyBOP (319 g, 0.612 mole, 0.95 eg) were mixed together in DMF (1 L) and cooled at 0° C. Triethylamine (149 g, 1.47 mole, 2.4 eg) was added dropwise at a rate to maintain internal temperature ≦20° C. Reaction mixture was then allowed to warm to room temperature and stirred for 18 hours. Reaction mixture was poured portionwise into saturated NaHCO$_3$ (4 L) and extracted with EtOAc (2×1 L). Half saturated NaCl solution was added to help partition. Combined organic fractions were washed with brine, 0.5 N HCl, brine, dried and evaporated to give a dark red oil. The latter was passed through a silica plug with 50% EtOAc/hexane to give of the title compound.

Step 2 (4-bromophenyl)(phenyl)methanol

To a solution of (4-bromophenyl)(phenyl)methanone (200 g, 0.766 mole) in THF (600 mL) and methanol (400 mL) was added in portions pulverized sodium borohydride (29 g, 0.766 mole) while maintaining the internal temperature between 3° C. and 10° C. After stirring for an additional 15 minutes, acetone (125 mL) was added and the mixture stirred for a subsequent 10 minutes. The solution was concentrated and the residue partitioned between water (250 mL) and ethyl acetate (1.0 L). The organic layer was separated, dried (Na$_2$SO$_4$), filtered and concentrated. The residue was pumped on by high vacuum for 18 hours to give the title compound as an oil.

Step 3 (4-bromophenyl)(phenyl)methyl 2,2,2-trichloroethanimidoate (4-bromophenyl)(phenyl)methanol from example 67 step 2 (175 g, 0.665 mol) was dissolved in Et$_2$O (700 mL) and sodium hydride (2.66 g of 60% dispension in oil, 0.067 mol, 0.1 eg) was added. Reaction mixture was cooled to 0° C. and trichloroacetonitrile (96 g, 0.665 mol, 1 eg) was added dropwise over 15 min. Reaction mixture was allowed to warm to room temperature and stirred for 1.5 hours. Mixture was evaporated to dryness and solid was stirred in hexane for 18 hours. The solid was filtered to give the product.

Step 4 (2S)-2-[(4-bromophenyl)(phenyl)methoxy]-N-(cyanomethyl)-4-methylpentanamide (2S)-N-(cyanomethyl)-2-hydroxy-4-methylpentanamide from example 67 step 1 (22.5 g, 0.132 mol) and (1R)-(-1-10-camphorsulfonic acid (2.85 g, 0.012 mol, 0.1 eg) were added to 1,2-dichloroethane (135 mL) and the suspension was heated to 50° C. (4-bromophenyl)(phenyl)methyl 2,2,2-trichloroethanimidoate (50 g, 0.123 mol, 0.93 eg) was added portionwise over 15 min. then reaction mixture was stirred at 50° C. for 10 min. The reaction was repeated with 2×50 g and 1×69 g of (4-bromophenyl)(phenyl)methyl 2,2,2 trichloroethanimidoate, using same proportions of other reagents. All the batches were combined and evaporated to give a dark red oil (320 g). The latter was dissolved in toluene (600 mL); insoluble material was filtered off and the filtrate was charged on a chromatography column, eluted with 5% EtOAc/toluene to give the title compound.

MS (−ESI) 413 415 [M−1]$^-$

EXAMPLE 68

Synthesis of (2S)-2-{[(R)-(4-bromophenyl)(phenyl)methyl]oxy}-N-(cyanomethyl)-4-methylpentanamide (2S)-2-{[(R)-(4-bromophenyl)(phenyl)methyl]oxy}-4-methylpentanoic acid from Step 2, Example 1, (46.5 g, 123 mmol) was dissolved in DMF (200 mL). To this mixture was added HATU (56.7 g, 149 mmol, 1.2 eg), Et$_3$N (57.7 g, 570 mmol, 4.6 eg), then added at 0° C. aminoacetonitrile hydrochloride (13.5 g, 146 mmol, 1.19 eg). The resulting reaction mixture was stirred at room temperature for 3 hours; then poured into 1 L of half saturated sodium bicarbonate. The aqueous phase was extracted with EtOAc (2×500 mL). Organic fraction was washed with brine (200 mL), 1NHCl (200 mL), brine (200 mL), 0.5 N NaOH (300 mL), brine (200 mL). Solvent was evaporated under reduced pressure and the resulting dark red oil which was chromatographed with 20% EA/hexane to give the title compound.

EXAMPLE 69

Synthesis of 2-[1-(4-bromophenyl)-2,2,2-trifluoroethoxy]-N-(cyanomethyl)-4-methylpentanamide Step, 1 methyl 2-bromo-4-methylpentanoate To a solution of 2-bromo-4-methylpentanoic acid (9.86 mmol, 1.31 g) in $CH_2Cl_2$ (100 mL), was added slowly a solution of diazomethane until no bubbles appears. The mixture was stirred at r.t. for 0.25 h. The volatiles were removed under reduced pressure to leave a yellow liquid. The crude methyl ester was used without further purification.

Step 2 1-(4-bromophenyl)-2,2,2-trifluoroethanol

To a solution of 1-(4-bromophenyl)-2,2,2-trifluoroethanone (37.7 mmol, 8.86 g) in methanol (89 mL) at 0° C., was added sodium borohydride (39.6, 1.50 g). The mixture was stirred for 1 h. HCl 10% (100 mL) was added and the mixture was stirred for 0.25 h. The mixture was extracted with $CH_2Cl_2$. The combined extracts were dried over anhydrous $MgSO_4$ and concentrated under reduced pressure. The crude alcohol was used without further purification.

Step 3 methyl 2-[1-(4-bromophenyl)-2,2,2-trifluoroethoxy]-4-methylpentanoate

Sodium hydride (60% W, 2.16 mmol, 87 mg) was suspended in dry THF and cooled to 0° C. A solution of 1-(4-bromophenyl)-2,2,2-trifluoroethanol from example 69 step 2 was added slowly and stirred at 0° C. over 0.75 h. A solution of methyl 2-bromo-4-methylpentanoate from example 69 step 1 was added and the mixture was allowed to warmed to r.t. and stirred overnight. The reaction was treated with 0.1 N aqueous hydrochloric acid, diluted with diethyl ether and ethyl acetate. The phases are separated and the organic layer was washed with 0.1N aqueous hydrochloric acid then brine and dried over magnesium sulfate. The volatiles were removed unde reduced pressure to yield methyl 4-methyl-2-(2,2,2-trifluoro-1-phenylethoxy)pentanoate that was used without further purification.

Step 4 4-methyl-2-(2,2,2-trifluoro-1-phenylethoxy)pentanoic acid

To a suspension of methyl 4methyl-2-(2,2,2-trifluoro-1-phenylethoxy)pentanoate from example 69 step 3 (0.63 mmol, 241 mg) in pyridine (7 mL), lithium iodide (1.26 mmol, 168 mg) was added and the mixture was heated at 140° C. for 24 h. The mixture was cooled to r.t. HCl 10% (20 mL) was added and HCl 12 N was added until pH 1. The mixture was extracted with ethyl acetate (50 mL) 3×. The combined extracts were dried over anhydrous $MgSO_4$ and concentrated. The crude title acid was used without further purification.

Step 5 2-[1-(4-bromophenyl)-2,2,2-trifluoroethoxy]-N-(cyanomethyl)-4-methylpentanamide To a solution of the 4-methyl-2-(2,2,2-trifluoro-1-phenylethoxy)pentanoic acid from example 69 step 4 (0.18 mmol, 68 mg) in DMF (2.5 mL) was added aminoacetonitrile hydrochloride (0.28 mmol, 26 mg) and HATU (0.21 mmol, 81 mg). Triethylamine (0.61 mmol, 85 μL) was added last. The mixture was stirred at r.t. overnight. $Et_2O$ (20 mL) was added, followed by HCl 1N (10 mL). The mixture was separated. The organic exract was washed with HCl 0.1N (10 mL), water and brine. The combined extracts were dried over anhydrous $MgSO_4$ and concentrated. Purification: 30:70 (AcOEt:Hex.) gave 2-[1-(4-bromophenyl)-2,2,2-trifluoroethoxy]-N-(cyanomethyl)-4-methylpentanamide.

EXAMPLE 70

Synthesis of (2S)-N-(cyanomethyl)-4-methyl-2-[((R)-phenyl{4-[(trimethylsilyl)ethynyl]phenyl}methyl)oxy]pentanamide To a solution of 2-[1-(4-bromophenyl)-2,2,2-trifluoroethoxy]-N-(cyanomethyl)-4-methylpentanamide from example 69 step 5 (4.06 mmol, 2.0 g) in $Et_3N$ (12 mL), was added trimethylsilane acetylene (6.09 mmol, 861 μL) followed by palladium tetrakis triphenylphosphine (0.08 mmol, 92 mg) and cupper iodide (0.12 mmol, 23 mg). The reaction was heated at 75° C. overnight. The mixture was cooled to r.t. and extracted with $Et_2O$ (20 mL). The phases were separated. The organic extract was washed with saturated aqueous ammonium chloride (20 mL). The organic extracts were dried over anhydrous $MgSO_4$ and concentrated under reduced pressure. Purification with 30:70 AcOEt:Hexanes gave the title amide.

MS (−APCI) 431.2 [M−1]$^-$

EXAMPLE 71

Synthesis of (2S)-N-(cyanomethyl)-2-{[(R)-(4-ethynylphenyl)(phenyl)methyl]oxy}-4-methylpentanamide To a solution of (2S)-N-(cyanomethyl)-4-methyl-2-[((R)-phenyl{4-[(trimethylsilyl)ethynyl]phenyl}methyl)oxy]pentanamide from example 70 (0.12 mmol, 50 mg) in THF:MeOH (1.3 mL: 50 uL) at 0° C., AcOH (3 drops) was added followed by tetrabutylammonium triphenyldifluorosilicate (0.01 mmol, 7 mg). The mixture was stirred 20 minutes at 0° C. The mixture was diluted with 1% sodium hydroxyde (3 mL) and diethlyl ether (5 mL). The phases were separated. The organic layer was dried over anhydrous $MgSO_4$ and concentrated under reduced pressure. Purification: 30:70 (AcOEt:Hex.) gave the title amide.

MS (−APCI) 459.1 [M−1]$^-$

EXAMPLE 72

Synthesis of (2S)-N-(cyanomethyl)-2-{[(R)-(4-cyanophenyl)(phenyl)methyl]oxy}-4-methylpentanamide To a solution of 2-[1-(4-bromophenyl)-2,2,2-trifluoroethoxy]-N-(cyanomethyl)-4-methylpentanamide from example 69 step 5 (2.03 mmol, 1.0 g) in DMF (2.5 mL), was added zinc cyanide (1.22 mmol, 144 mg) followed by palladium tetrakistriphenylphosphine (0.08 mmol, 92 mg). The mixture was degassed three times via the freeze-thaw method. The mixture was heated at 80° C. overnight. The next day, more zinc cyanide (0.61 mmol, 72 mg) and tetrakistriphenylphosphine (0.04 mmol, 46 mg) were added The mixture was heated at 80° C. overnight. The mixture was cooled to r.t. and diluted with AcOEt (20 mL). The phases were separated and the organic extract was washed with ammonium chloride, brine. The organic layer was dried over anhydrous MgSO₄ and concentrated under reduced pressure. Purification: 50:50 (AcOEt:Hex.) gave the title amide.

MS (−APCI) 360.1 [M−1]⁻

EXAMPLE 73

Synthesis of 2-{[(4-bromophenyl)(phenyl)methyl]thio}-N-(cyanomethyl)-4-methylpentanamide Step 1 methyl 2-{[(4-bromophenyl)(phenyl)methyl]thio}-4-methylpentanoate To a solution of triisopropylsilanethiol (1.75 mL, 8.05 mmoles) and (4-bromophenyl)(phenyl)methanol from example 67 step 2 (3.5, 8.05 mmoles) in 16 mL of DMF was added sodium hydride as a 60% emulsion in oil (386 mg, 9.66 mmoles). After the exotherm has passed, 1.65 mL (10 mmole) of methyl 2-bromo-4-methylpentanoate was added followed by 12 mL of a 1.0 M solution of tetrabutylammonium fluoride in tetrahydrofuran. After stirring overnight, the reaction was diluted with diethyl ether (200 mL) and washed twice with 0.1 N HCl, twice with water and once with brine. The organic phase was dried over magnesium sulfate and concentrated under reduced pressure. The oil as purified by flash chromatography (9:1 hexanes to ethyl acetate) to give the title ester.

Step 2 2-{[(4-bromophenyl)(phenyl)methyl]thio}-4-methylpentanoic acid

To a solution of 1 g (2.4 mmoles) of methyl 2-{[(4-bromophenyl)(phenyl)methyl]thio}-4-methylpentanoate from example 73 step 2 in a ternary mixture of tetrahydrofuran, methanol and water was added solid lithium hydroxyde monohydrate (151 mg, 3.6 mmoles). The reaction was stirred until disappearance of the starting material by thin layer chromatography and diluted with 1N hydrochloric acid and dichloromethane. The phases were separated and the aqueous phase was washed twice with dichloromethane. The combined organic layers were dried over magnesium sulfate and concentrated under reduced pressure. The title acid was used without further purification.

Step 3 2-{[(4-bromophenyl)(phenyl)methyl]thio}-N-(cyanomethyl)-4-methylpentanamide The procedure from step 3 example 1 was used except that 2-{[(4-bromophenyl)(phenyl)methyl]thio}-4-methylpentanoic acid was used as the carboxylic acid component to give the title compound.

MS (−ESI) 431.0 [M−1]⁻

EXAMPLE 74

Synthesis of 2-{[(4-bromophenyl)(phenyl)methyl]sulfonyl}-N-(cyanomethyl)-4-methylpentanamide To a solution of 2-{[(4-bromophenyl)(phenyl)methyl]thio}-N-(cyanomethyl)-4-methylpentanamide from example 73 step 3 (111 mg, 0.26 mmoles) in a 1:1 mixture of dichloromethane and methanol at 0° C. is added 318 mg (0.64 mmoles) MMPP. After stirring for 30 minutes, the reaction is partitioned between ethyl acetate and saturated aqueous bicarbonate. The phases are separated, the organic layer was washed with saturated aqueous bicarbonate, water and brine successively. The organic portion is dried over magnesium sulfate and concentrated under reduced pressure. The oil was purified via flash chromatography on silica gel to afford the title compound.

MS (−ESI) 463.1 [M−1]⁻

What is claimed is:
1. A compound of the formula:

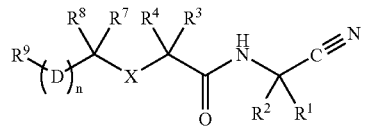

wherein R¹ is hydrogen, $C_{1-6}$ alkyl or $C_{1-6}$ alkenyl wherein said alkyl and alkenyl groups are optionally substituted with halo;

R² is hydrogen, $C_{1-6}$ alkyl or $C_{1-6}$ alkenyl wherein said alkyl and alkenyl groups are optionally substituted with halo;

or R¹ and R² can be taken together with the carbon atom to which they are attached to form a $C_{3-8}$ cycloalkyl ring wherein said ring system is optionally substituted with $C_{1-6}$ alkyl, hydroxyalkyl or halo;

R³ is hydrogen, $C_{1-6}$ alkyl or $C_{1-6}$ alkenyl wherein said alkyl and alkenyl groups are optionally substituted with $C_{3-6}$ cycloalkyl or halo;

R⁴ is hydrogen, $C_{1-6}$ alkyl or $C_{1-6}$ alkenyl wherein said alkyl and alkenyl groups are optionally substituted with $C_{3-6}$ cycloalkyl or halo;

or R³ and R⁴ can be taken together with the carbon atom to which they are attached to form a $C_{3-8}$ cycloalkyl ring, $C_{5-8}$ cycloalkenyl ring, or five to seven membered heterocycloalkyl wherein said cycloalkyl, cycloalkenyl and heterocycloalkyl groups are optionally substituted with $C_{1-6}$ alkyl, halo, hydroxyalkyl, hydroxy, alkoxy or keto;

X is O;

R⁷ is $C_{2-6}$ alkenyl, $C_{2-6}$ alkynyl, $C_{1-6}$ haloalkyl, aryl, heteroaryl; wherein said alkyl, alkenyl, alkynyl, haloalkyl, aryl and heteroaryl groups are optionally substituted on either the carbon or the heteroatom with one to five substituents independently selected from $C_{1-6}$ alkyl, halo, keto, cyano, haloalkyl, hydroxyalkyl, —OR⁹, —O(aryl), —NO₂, —NH₂, —NHS(O)₂R¹⁰, —R¹³SO₂R¹², —SO₂R¹², —SO(R₁₂), —SO₂N(Rᶜ)(Rᵈ), —SO₂N(R¹⁰)C(O)(R¹²), —C(R¹⁰)(R¹¹)N(R¹⁰)(R₁₁), —C(R¹⁰)(R¹¹)OH, —COOH, —C(Rᵃ)(Rᵇ)C(O)N(Rᵃ)(Rᵇ), —N(R¹⁰)C(R¹⁰)(R¹¹)(R¹³), —NH(CH₂)₂OH, —NHC(O)OR₁₀, —Si(CH₃)₃, heterocycloalkyl, aryl or heteroaryl;

R⁸ is hydrogen, $C_{1-6}$ alkyl, $C_{2-6}$ alkenyl, $C_{2-6}$ alkynyl, $C_{1-6}$ haloalkyl, aryl, heteroaryl; wherein said alkyl, alkenyl, alkynyl, haloalkyl, aryl and heteroaryl groups are optionally substituted on either the carbon or the heteroatom with one to five substituents independently selected from $C_{1-6}$ alkyl, halo, keto, cyano, haloalkyl, hydroxyalkyl, —OR⁹, —O(aryl), —NO₂, —NH₂, —NHS(O)₂R¹⁰, —R¹³SO₂R¹², —SO₂R¹², —SO(R₁₂), —SO₂N(Rᶜ)(Rᵈ), —SO₂N(R¹⁰)C(O)(R¹²), —C(R¹⁰)(R¹¹)N(R¹⁰)(R₁₁), —C(R¹⁰)(R¹¹)OH, —COOH, —C(Rᵃ)(Rᵇ)C(O)N(Rᵃ)(Rᵇ), —N(R¹⁰)C(R¹⁰)(R¹¹)(R₁₃), —NH(CH₂)₂OH, —NHC(O)OR¹⁰, —Si(CH₃)₃, heterocycloalkyl, aryl or heteroaryl;

D is aryl, heteroaryl, $C_{3-8}$ cycloalkyl, or heterocycloalkyl, wherein said aryl, heteroaryl, cycloalkyl and heterocycloalkyl groups, which may be monocyclic or bicyclic, are optionally substituted on either the carbon or the heteroatom with one to three substituents selected from $C_{1-6}$ alkyl, $C_{2-6}$ alkenyl, $C_{2-6}$ alkynyl, $C_{1-6}$ alkyloxy, halo, keto, nitro, cyano, aryl, heteroaryl, $C_{3-8}$ cycloalkyl, heterocyclyl, —C(O)OR$^{10}$, —C(O)OSi[CH(CH$_3$)$_2$]$_3$, —OR$^{10}$, —C(O)R$^{10}$, —R$^{10}$C(O)R$_{13}$, —C(O)R$_{13}$, —C(O)N(R$_{12}$)(R$_{12}$), —C(R$^{10}$)(R$^{11}$)OH, —SR$^{12}$, —SR$^{13}$, —R$^{10}$SR$^{13}$, —R$^{13}$, —C(R$^{13}$)$_3$, —C(R$^{10}$)(R$^{11}$)N(R$^{13}$)$_2$, —SO$_2$R$^{12}$, —SO(R$_{12}$), —SO$_2$R$_{13}$, —SO$_2$N(R$^c$)(R$^d$), —SO$_2$CH(R$^{10}$)(R$_{11}$), —SO$_2$N(R$^{10}$)C(O)(R$_{12}$), —SO$_2$(R$^{10}$)C(O)N(R$_{12}$)$_2$, —OSO$_2$R$_{10}$, —N(R$^{10}$)(R$^{11}$), —N(R$^{10}$)C(O)NR$^{10}$R$^{13}$, —N(R$^{10}$)C(O)R$_{10}$, —N(R$^{10}$)C(O)OR$^{10}$, —N(R$^{10}$)SO$_2$R$^{10}$, —C(R$^{10}$)(R$^{11}$)NR$^{10}$C(R$^{10}$)(R$^{11}$)R$^{13}$, —C(R$^{10}$)(R$^{11}$)N(R$^{10}$)R$_{13}$, —C(R$^{10}$)(R$^{11}$)N(R$^{10}$)(R$^{11}$), —C(R$^{10}$)(R$^{11}$)SC(R$^{10}$)(R$^{11}$)(R$_{13}$), R$^{10}$S—, —C(R$^a$)(R$^b$)NR$^a$C(R$^a$)(R$^b$)(R$_{13}$), —C(R$^a$)(R$^b$)N(R$^a$)(R$^b$), —C(R$^a$)(R$^b$)C(R$^a$)(R$^b$)N(R$^a$)(R$^b$), —C(O)C(R$^a$)(R$^b$)N(R$^a$)(R$^b$), —C(R$^a$)(R$^b$)N(R$^a$)C(O)R$^{13}$ or —C(R$^a$)(R$^b$)C(O)N(R$^a$)(R$^b$); wherein said alkyl, alkenyl, alkynyl, haloalkyl, alkoxy, aryl, heteroaryl, cycloalkyl and heterocyclyl groups are optionally substituted on either the carbon or the heteroatom with one to five substituents independently selected from $C_{1-6}$ alkyl, $C_{3-8}$ cycloalkyl, halo, keto, cyano, haloalkyl, hydroxyalkyl, —OR$^{13}$, —NO$_2$, —NH$_2$, —NHS(O)$_2$R$^{10}$, —R$^{13}$SO$_2$R$_{12}$, SO$_2$R$^{12}$, —SO(R$^{12}$), —SO$_2$N(R$^c$)(R$^d$), —SO$_2$N(R$^{10}$)C(O)(R$^{12}$), —C(R$^{10}$)(R$^{11}$)N(R$^{10}$)(R$^{11}$), —C(R$^{10}$)(R$^{11}$)OH, —COOH, —C(R$^a$)(R$^b$)C(O)N(R$^a$)(R$^b$), —N(R$^{10}$)C(R$^{10}$)(R$_{11}$), —NH(CH$_2$)$_2$OH, —NHC(O)OR$^{10}$, —Si(CH$_3$)$_3$, heterocycloalkyl, aryl or heteroaryl;

R$^9$ is hydrogen, hydroxy, cyano, $C_{1-6}$ alkyl, $C_{2-6}$ alkenyl, $C_{2-6}$ alkynyl, $C_{1-6}$ alkyloxy, halo, aryl, heteroaryl, $C_{3-8}$ cycloalkyl, heterocycloalkyl, —C(O)OR$^{10}$, —OR$^{10}$, —C(O)R$^{10}$, —C(O)R$^{13}$, —C(O)N(R$^{12}$)(R$^{12}$), —C(R$^{10}$)(R$^{11}$)OH, —R$^{10}$SR$^{13}$, —R$^{13}$, —C(R$^{13}$)$_3$, —C(R$^{10}$)(R$^{11}$)N(R$^{13}$)$_2$, SR$^{10}$, —SO$_2$R$^{12}$, —SO(R$^{12}$), —SO$_2$R$^{13}$, —SO$_2$N(R$^c$)(R$^d$), —SO$_2$CH(R$^{10}$)(R$^{11}$), —N(R$^{10}$)(R$^{11}$), —N(R$^{10}$)C(O)NR$^{10}$R$^{13}$, —N(R$^{10}$)C(O)R$^{10}$, —N(R$^{10}$)C(O)OR$^{10}$, —N(R$^{10}$)SO$_2$R$^{10}$, —C(R$^{10}$)(R$^{11}$)NR$^{10}$C(R$^{10}$)(R$^{11}$)R$^{13}$, —C(R$^{10}$)(R$^{11}$)N(R$^{10}$)R$^{13}$, —C(R$^{10}$)(R$^{11}$)N(R$^{10}$)(R$^{11}$), —C(R$^{10}$)(R$^{11}$)SC(R$^{10}$)(R$^{11}$)—, R$^{10}$S—, —C(R$^a$)(R$^b$)NR$^a$C(R$^a$)(R$^b$), —C(R$^a$)(R$^b$)N(R$^a$)(R$^b$), —C(R$^a$)(R$^b$)C(R$^a$)(R$^b$)N(R$^a$)(R$^b$), —C(O)C(R$^a$)(R$^b$)N(R$^a$)(R$^b$), —C(R$^a$)(R$^b$)N(R$^a$)C(O)R$^{13}$; wherein said alkyl, alkenyl, alkynyl, alkoxy, aryl, heteroaryl, cycloalkyl and heterocycloalkyl groups are optionally substituted on either the carbon or the heteroatom with one to five substituents independently selected from $C_{1-6}$ alkyl, $C_{3-8}$ cycloalkyl, halo, keto, cyano, haloalkyl, hydroxyalkyl, —OR$^{13}$, —NO$_2$, —NH$_2$, —NHS(O)$_2$R$^8$, —R$^{13}$SO$_2$R$^{12}$, SO$_2$R$^{12}$, SO(R$^{12}$), —SO$_2$N(R$^c$)(R$^d$), SO$_2$N(R$^{10}$)C(O)(R$^{12}$), —C(R$^{10}$)(R$^{11}$)N(R$^{10}$)(R$^{11}$), —C(R$^{10}$)(R$^{11}$)OH, —COOH, —C(R$^a$)(R$^b$)C(O)N(R$^a$)(R$^b$), —N(R$^{10}$)C(R$^{10}$)(R$^{11}$), —NH(CH$_2$)$_2$OH, —NHC(O)OR$^{10}$, Si(CH$_3$)$_3$, heterocycloalkyl, aryl or heteroaryl;

R$^{10}$ is hydrogen or $C_{1-6}$ alkyl;

R$^{11}$ is hydrogen or $C_{1-6}$ alkyl;

R$^{12}$ is hydrogen or $C_{1-6}$ alkyl which is optionally substituted with halo, alkoxy, cyano, —NR$^{10}$ or —SR$^{10}$;

R$^{13}$ is selected from the group consisting of hydrogen, aryl, aryl($C_{1-4}$) alkyl, heteroaryl, heteroaryl($C_{1-4}$)alkyl, $C_{3-8}$cycloalkyl, $C_{3-8}$cycloalkyl($C_{1-4}$)alkyl, and heterocycloalkyl($C_{1-4}$)alkyl wherein said groups can be optionally substituted with halo or alkoxy;

R$^a$ is hydrogen, $C_{1-6}$ alkyl, ($C_{1-6}$ alkyl)aryl, ($C_{1-6}$ alkyl) hydroxyl, —O($C_{1-6}$ alkyl), hydroxyl, halo, aryl, heteroaryl, $C_{3-8}$ cycloalkyl, heterocycloalkyl, wherein said alkyl, aryl, heteroaryl, $C_{3-8}$ cycloalkyl and heterocycloalkyl can be optionally substituted on either the carbon or the heteroatom with $C_{1-6}$ alkyl or halo;

R$^b$ is hydrogen, $C_{1-6}$ alkyl, ($C_{1-6}$ alkyl)aryl, ($C_{1-6}$ alkyl) hydroxyl, alkoxyl, hydroxyl, halo, aryl, heteroaryl, $C_{3-8}$ cycloalkyl, heterocycloalkyl,wherein said alkyl, aryl, heteroaryl, $C_{3-8}$ cycloalkyl and heterocycloalkyl can be optionally substituted on either the carbon or the heteroatom with $C_{1-6}$ alkyl or halo;

or R$^a$ and R$^b$ can be taken together with the carbon atom to which they are attached or are between them to form a $C_{3-8}$ cycloalkyl ring or $C_{3-8}$ heterocycloalkyl ring wherein said 3-8 membered ring system may be optionally substituted with $C_{1-6}$ alkyl and halo;

R$^c$ is hydrogen or $C_{1-6}$ alkyl which is optionally substituted with halo or OR$^{13}$;

R$^d$ is hydrogen or $C_{1-6}$ alkyl which is optionally substituted with halo or OR$^{13}$;

or R$^c$ and R$^d$ can be taken together with the nitrogen atom to which they are attached or are between them to form a $C_{3-8}$ heterocycloalkyl ring which is optionally substituted with $C_{1-6}$ alkyl, halo hydroxyalkyl, hydroxy, alkoxy or keto;

n is two;

or a pharmaceutically acceptable salt or stereoisomer thereof.

2. The compound of claim 1 wherein R$^3$ is H and R$^4$ is $C_{1-6}$ alkyl which is optionally substituted with $C_{3-6}$ cycloalkyl or halo; or a pharmaceutically acceptable salt or stereoisomers thereof.

3. The compound of claim 2 wherein R$^3$ is H and R$^4$ is isobutyl; or a pharmaceutically acceptable salt or stereoisomer thereof.

4. The compound of claim 1 wherein R$^1$ and R$^2$ are each H; or a pharmaceutically acceptable salt or stereoisomer thereof.

5. The compound of claim 1 wherein R$^1$ and R$^2$ can be taken together with the carbon atom to which they are attached to form a $C_{3-8}$ cycloalkyl ring wherein said ring system is optionally substituted with $C_{1-6}$ alkyl, hydroxyalkyl or halo; or a pharmaceutically acceptable salts or stereoisomer thereof.

6. The compound of claim 5 wherein R$^1$ and R$^2$ can be taken together with the carbon atom to which they are attached to form a cyclopropyl ring wherein said ring system is optionally substituted with $C_{1-6}$ alkyl or halo; or a pharmaceutically acceptable salts-or stereoisomers thereof.

7. The compound of claim 1 wherein R$^7$ is aryl, heteroaryl or $C_{1-6}$ haloalkyl and R$^8$ is hydrogen; or a pharmaceutically acceptable salt; or stereoisomer thereof.

8. The compound of claim 1 wherein D is aryl, heteroaryl, cycloalkyl or heterocycloalkyl; or a pharmaceutically acceptable salt or stereoisomers thereof.

9. The compound of claim 8 wherein D is phenyl or a pharmaceutically acceptable salt or stereoisomers thereof.

10. The compound of claim 1 wherein R$^9$ is aryl, heteroaryl or heterocycloalkyl, wherein wherein said groups are optionally substituted on either the carbon or the heteroatom with one to five substituents independently selected from $C_{1-6}$ alkyl, halo, —SO$_2$R$^{12}$, —SO(R$^{12}$) or aryl; or a pharmaceutically acceptable salt or stereoisomer thereof.

11. The compound of claim 1 selected from:

(2S)—N-(cyanomethyl)-4-methyl-2-{[(R)-phenyl(4'-piperazin-1-yl-1,1'-biphenyl-4-yl)methyl]oxy}pentanamide;

(2S)—N-(cyanomethyl)-4-methyl-2-{[(R)-phenyl(4'-pyridin-4-yl-1,1'-biphenyl-4-yl)methyl]oxy}pentanamide;

(2S)—N-(cyanomethyl)-4-methyl-2-{[(S)-[4-(methylsulfonyl)phenyl](4'-piperazin-1-yl-1,1'-biphenyl-4-yl)methyl]oxyl}pentanamide;

(2S)—N-(cyanomethyl)-2-{[(R)-[4'-(1H-imidazol-1-yl)-1,1'-biphenyl-4-yl](phenyl)methyl]oxy}-4-methylpentanamide;

(2S)-2-{[(S)-(4-chlorophenyl)(4'-piperazin-1-yl-1,1'-biphenyl-4-yl)methyl]oxy}-N-(cyanomethyl)-4-methylpentanamide;

(2S)—N-(cyanomethyl)-2-{[(S)-mesityl(4'-piperazin-1-yl-1,1'-biphenyl-4-yl)methyl]oxy}-4-methylpentanamide;

(2S)-2-[[4-(3-chloropyrazin-2-yl)phenyl](phenyl)methoxy]-N-(cyanomethyl)-4-methylpentanamide;

(2S)-2-[[4'-(aminosulfonyl)-1,1'-biphenyl-4-yl](phenyl)methoxy]-N-(cyanomethyl)-4-methylpentanamide;

(2S)—N-(cyanomethyl)-4-methyl-2-[[4'-(methylsulfonyl)-1,1'-biphenyl-4-yl](phenyl)methoxy]pentanamide;

(2S)—N-(cyanomethyl)-4-methyl-2-[phenyl(4-quinolin-3-ylphenyl)methoxy]pentanamide;

(2S)—N-(cyanomethyl)-4-methyl-2-[phenyl(4-pyrimidin-5-ylphenyl)methoxy]pentanamide;

(2S)—N-(cyanomethyl)-4-methyl-2-[phenyl(4-quinolin-8-ylphenyl)methoxy]pentanamide;

(2S)—N-(cyanomethyl)-2-[{4-[6-(hydroxymethyl)-1-oxidopyridin-3-yl]phenyl}(phenyl)methoxy]-4-methylpentanamide;

(2S)—N-(cyanomethyl)-4-methyl-2-[phenyl(4-pyridin-4-ylphenyl)methoxy]pentanamide;

(2S)—N-(cyanomethyl)-2-[[4-(1H-indol-4-yl)phenyl](phenyl)methoxy]-4-methylpentanamide;

(2S)—N-(cyanomethyl)-4-methyl-2-[phenyl(4-pyridin-2-ylphenyl)methoxy]pentanamide;

(2S)—N-(cyanomethyl)-4-methyl-2-[phenyl(4-pyrazin-2-ylphenyl)methoxy]pentanamide;

(2S)—N-(cyanomethyl)-4-methyl-2-[phenyl(4-pyridin-3-ylphenyl)methoxy]pentanamide;

(2S)—N-(cyanomethyl)-4-methyl-2-(phenyl {4-[5-(2H-tetraazol-5-yl)pyridin-3-yl]phenyl}methoxy)pentanamide;

(2S)—N-(cyanomethyl)-4-methyl-2-[[4-(3-methylpyridin-2-yl)phenyl](phenyl)methoxy]pentanamide;

2-{4-[[((1S)-1-{[(cyanomethyl)amino]carbonyl}-3-methylbutyl)oxy](phenyl)methyl]phenyl}isonicotinic acid;

(2S)—N-(cyanomethyl)-4-methyl-2-[phenyl(4-pyrimidin-2-ylphenyl)methoxy]pentanamide;

ethyl 4'-[[((1S)-1-{[(cyanomethyl)amino]carbonyl}-3-methylbutyl)oxy](phenyl)methyl]-1,1'-biphenyl-4-carboxylate;

4'-[[((1S)-1-{[(cyanomethyl)amino]carbonyl}-3-methylbutyl)oxy](phenyl)methyl]-1,1'-biphenyl-4-carboxamide;

(2S)—N-(cyanomethyl)-4-methyl-2-{[(S)-(4'-piperazin-1-yl-1,1'-biphenyl-4-yl)(thien-2-yl)methyl]oxy}pentanamide;

N-(cyanomethyl)-4-methyl-2-[(4'-piperazin-1-yl-1,1'-biphenyl-4-yl)(pyridin-2-yl)methoxy]pentanamide;

N-(cyanomethyl)-4-methyl-2-[(4'-piperazin-1-yl-1,1'-biphenyl-4-yl)(1,3-thiazol-2-yl)methoxy]pentanamide;

N-(cyanomethyl)-2-[(4-fluorophenyl)(4'-piperazin-1-yl-1,1'-biphenyl-4-yl)methoxy]-4-methylpentanamide;

N-(1-cyanocyclopropyl)-2-[(4-fluorophenyl)(4'-piperazin-1-yl-1,1'-biphenyl-4-yl)methoxy]-4-methylpentanamide;

N-(cyanomethyl)-4-methyl-2-[phenyl(4'-piperazin-1-yl-1,1'-biphenyl-4-yl)methoxy]pentanamide;

(2S)—N-(cyanomethyl)-2-[(4-fluorophenyl)(4'-piperazin-1-yl-1,1'-biphenyl-4-yl)methoxy]-4-methylpentanamide;

(2S)—N-(cyanomethyl)-4-methyl-2-{[(R)-phenyl(4'-piperazin-1-yl-1,1'-biphenyl-4-yl)methyl]oxy}pentanamide;

(2S)—N-(cyanomethyl)-4-methyl-2-[phenyl(4'-piperazin-1-yl-1,1'-biphenyl-4-yl)methoxy]pentanamide;

(2S)—N-(cyanomethyl)-4-methyl-2-{[(S)-phenyl(4'-piperazin-1-yl-1,1'-biphenyl-4-yl)methyl]oxy}pentanamide;

(2S)—N-(Cyanomethyl)-4-methyl-2-{[(R)-[4'-(methylthio)-1,1'-biphenyl-4-yl](phenyl)methyl]oxy}pentanamide;

(2S)—N-(cyanomethyl)-4-methyl-2-{[(R)-[4'-(methylsulfonyl)-1,1'-biphenyl-4-yl](phenyl)methyl]oxy}pentanamide;

(2S)—N-(Cyanomethyl)-4-methyl-2-{[(R)-(4'-morpholin-4-yl-1,1'-biphenyl-4-yl)(phenyl)methyl]oxy}pentanamide;

N-(cyanomethyl)-4-methyl-2-[2,2,2-trifluoro-1-(4'-piperazin-1-yl-1,1'-biphenyl-4-yl)ethoxy]pentanamide;

N-(cyanomethyl)-4-methyl-2-[phenyl(4'-piperazin-1-yl-1,1'-biphenyl-4-yl)methoxy]pentanamide;

(2S)—N-(cyanomethyl)-4-methyl-2-{[(R)-{4'-[4-(methylsulfonyl)piperazin-1-yl]-1,1'-biphenyl-4-yl}(phenyl)methyl]oxy}pentanamide;

(2S)—N-(cyanomethyl)-4-methyl-2-{[(R)-[4'-(4-methylpiperazin-1-yl)-1,1'-biphenyl-4-yl](phenyl)methyl]oxy}pentanamide;

N-(cyanomethyl)-4-methyl-2-(2,2,2-trifluoro-1-{4'-[4-(methylsulfonyl)piperazin-1-yl]-1,1'-biphenyl-4-yl}ethoxy)pentanamide;

(2S)—N-(cyanomethyl)-4-methyl-2-{[(R)-phenyl(4-pyridin-4-ylphenyl)methyl]oxy}pentanamide;

4-{4'-[(R)-[((1S)-1-{[(cyanomethyl)amino]carbonyl}-3-methylbutyl)oxy](phenyl)methyl]-1,1'-biphenyl-4-yl}-1,1-dimethylpiperazin-1-ium iodide;

(2S)—N-(cyanomethyl)-2-{[(R)-{4'-[4-(2-hydroxyethyl)piperazin-1-yl]-1,1'-biphenyl-4-yl}(phenyl)methyl]oxy}-4-methylpentanamide;

N-(cyanomethyl)-4-methyl-2-{2,2,2-trifluoro-1-[4'-(methylthio)-1,1'-biphenyl-4-yl]ethoxy}pentanamide;

N-(cyanomethyl)-4-methyl-2-{2,2,2-trifluoro-1-[4'-(methylsulfonyl)-1,1'-biphenyl-4-yl]ethoxy}pentanamide;

(2S)-2-{[(R)-[4-(1,1'-biphenyl-4-ylcarbonyl)phenyl](phenyl)methyl]oxy}- N-(eyanomethyl)-4-methylpentanamide;

(2S)—N-(cyanomethyl)-4-methyl-2-{phenyl[5-(4-piperazin-1-ylphenyl)pyridin-2-yl]methoxy}pentanamide;

(2S)—N-(cyanomethyl-4-methyl-2-[{5-[4-(methylthio)phenyl]pyridin-2-yl}(phenyl)methoxy]pentanamide;

(2S)—N-(cyanomethyl)-4-methyl-2-[{5-[4-(methylthio)phenyl]pyridin-2-yl}(phenyl)methoxy]pentanamide;

(2S)—N-(cyanomethyl-4-methyl-2-{[R or S)-{5-[4-(methylsulfonyl)phenyl]pyridin-2-yl}(phenyl)methyl]oxy}pentanamide;

(2S)—N-(cyanomethyl-4-methyl-2-{[(R or S)-{5-[4-methylsulfonyl)phenyl]pyridin-2-yl}(phenyl)methyl]oxy}pentanamide;

(2S)—N-(cyanomethyl-4-methyl-2-[{5-[4-(methylsulfonyl)phenyl]-1-oxidopyridin-2-yl}(phenyl)methoxy]pentanamide;

(2S)—N-(cyanomethyl)-4-methyl-2-{[(R)-[4-(6-methyl-1-oxidopyridin-3-yl)phenyl](phenyl)(phenyl)methyl]oxy}pentanamide;

(2S)—N-(cyanomethyl)-4-methyl-2-{[(R)-[4-(1-oxidopyridin-4-yl)phenyl](phenyl)methyl]oxy}pentanamide;

(2S)—N-(cyanomethyl)-2-{[(R)-{4-[1-(2-methoxyethyl)-1-oxidopiperidin-4-yl]phenyl}(phenyl)(phenyl)methyl]oxy-4-methylpentanamide;

(2S)—N-(cyanomethyl)-4-methyl-2-{[(R)-phenyl(4-pyridin-3-ylphenyl)methyl]oxy}pentanamide;

(2S)—N-(cyanomethyl)-4-methyl-2-{[(R)-[4-(1-oxidopyridin-3-yl)phenyl](phenyl)methyl]oxy}pentanamide;

(2S)—N-(cyanomethyl)-4-methyl-2-{[(R)-phenyl(4-quinolin-3-ylphenyl)methyl]oxy}pentanamide;

(2S)—N-(cyanomethyl)-4-methyl-2-{[(R)-[4-(1-methyl-1,2,3,4-tetrahydroquinolin-3-yl)phenyl](phenyl)methyl]oxy}pentanamide;

(2S)—N-(cyanomethyl)-4-methyl-2-{[(R)-[4-(1-oxidoquinolin-3-yl)phenyl](phenyl)methyl]oxy}pentanamide;

(2S)—N-(1-cyanocyclopropyl)-2-[(R)-[4'-(1-hydroxycyclopropyl)biphenyl-4-yl](phenyl)methoxy]-4-methylpentanamide;

(2S)—N-(1-cyanocyclopropyl)-4-methyl-2-{(R)-phenyl[4'-(2,2,2-trifluoro-1-hydroxyethyl)biphenyl-4-yl]methoxy}pentanamide;

(2S)-2-[(R)-[4'-(1-amino-2,2,2-trifluoroethyl)biphenyl-4-yl](phenyl)methoxy]-N-(1-cyanocyclopropyl)-4-methylpentanamide;

1-{4'-[(R)-[((1S)-1-{[(1-cyanocyclopropyl)amino]carbonyl }-3-methylbutyl)oxy](phenyl)methyl]biphenyl-4-yl}cyclopropanecarboxylic acid;

2-{4'-[(R)-[((1S)-1-{[(1-cyanocyclopropyl)amino]carbonyl}-3-methylbutyl)oxy](phenyl)methyl]biphenyl-4-yl}-2-hydroxypropanoic acid;

(2S)—N-(1-cyanocyclopropyl)-2-[(R)-[4'-(2-hydroxyethyl)biphenyl-4-yl](phenyl)methoxy]-4-methylpentanamide;

(2S)—N-(1-cyanocyclopropyl)-2-[(R)-{4'-[cyclopropyl(hydroxy)methyl]biphenyl-4-yl}(phenyl)methoxy]-4-methylpentanamide;

(2S)—N-(1-cyanocyclopropyl)-2-[(R)-[3'-(1-hydroxyethyl)biphenyl-4-yl](phenyl)methoxy]-4-methylpentanamide;

(2S)—N-(1-cyanocyclopropyl)-2-[(R)-[3'-(1-hydroxy-1-methylethyl)biphenyl-4-yl](phenyl)methoxy]-4-methylpentanamide;

(2S)—N-(1-cyanocyclopropyl)-2-[(R)-[3'-(1-cyanocyclopropyl)biphenyl-4-yl](phenyl)methoxy]-4-methylpentanamide;

(2S)—N-(1-cyanocyclopropyl)-2-[(R)-[4'-(1-cyanocyclopropyl)biphenyl-4-yl](phenyl)methoxy]-4-methylpentanamide;

(2S)-2-[(R)-[3',4'-bis(1-hydroxy-1-methylethyl)biphenyl-4-yl](phenyl)methoxy]-N-(1-cyanocyclopropyl)-4-methylpentanamide;

(2S)-2-[(R)-[3',4'-bis(1-hydroxycyclopropyl)biphenyl-4-yl](phenyl)methoxy]-N-(1-cyanocyclopropyl)-4-methylpentanamide;

or a pharmaceutically acceptable salt or stereoisomers thereof.

12. A pharmaceutical composition comprising a compound according to claim 1 and a pharmaceutically acceptable carrier.

13. A process for making a pharmaceutical composition comprising combining a compound according to claim 1 and a pharmaceutically acceptable carrier.

* * * * *